US010731225B2

(12) United States Patent
Broglie et al.

(10) Patent No.: US 10,731,225 B2
(45) Date of Patent: *Aug. 4, 2020

(54) METHODS FOR MAKING PLANTS RESISTANT TO FUNGAL PATHOGENS

(71) Applicant: E. I. DU PONT DE NEMOURS AND COMPANY, Wilmington, DE (US)

(72) Inventors: Karen E. Broglie, Landenberg, PA (US); Karlene H Butler, Newark, DE (US)

(73) Assignee: E.I. DU PONT DE NEMOURS AND COMPANY DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,805

(22) Filed: Dec. 14, 2018

(65) Prior Publication Data

US 2019/0177806 A1    Jun. 13, 2019

Related U.S. Application Data

(60) Continuation of application No. 15/492,199, filed on Apr. 20, 2017, now Pat. No. 10,202,655, which is a continuation of application No. 14/159,220, filed on Jan. 20, 2014, now Pat. No. 9,657,356, which is a division of application No. 13/272,057, filed on Oct. 12, 2011, now Pat. No. 8,633,349, which is a continuation of application No. 12/139,039, filed on Jun. 13, 2008, now Pat. No. 8,053,631.

(60) Provisional application No. 60/944,209, filed on Jun. 15, 2007.

(51) Int. Cl.
  *C12Q 1/68* (2018.01)
  *C12Q 1/6895* (2018.01)
  *C07K 14/415* (2006.01)
  *C12N 15/82* (2006.01)

(52) U.S. Cl.
  CPC .......... *C12Q 1/6895* (2013.01); *C07K 14/415* (2013.01); *C12N 15/8282* (2013.01)

(58) Field of Classification Search
  None
  See application file for complete search history.

(56) References Cited

U.S. PATENT DOCUMENTS 8,053,631 B2 * 11/2011 Broglie ................ C07K 14/415
                                                      800/279
10,202,655 B2 * 2/2019 Broglie ................ C07K 14/415

FOREIGN PATENT DOCUMENTS

WO   2006/107931 A2   10/2006

OTHER PUBLICATIONS

U.S. Appl. No. 13/270,722, filed Oct. 11, 2011, Pioneer Hi-Bred International, Inc.
International Search Report for International Application No. PCT/US2008/087954 completed Oct. 16, 2008.
Written Opinion for International Application No. PCT/US2008/087954.
Toman, J. et al, "Inheritance of Resistance to Anthracnose Stalk Rot of Corn", Phytopathology, St. Paul, MN, US. vol. 83, No. 9, 1993.
Weldekian, T. et al; "Inheritance of Anthracnose Stalk Rot Resistance in Maize," Maydica, vol. 38 (1993); pp. 189-192.
Database Geneseq [Online] Apr. 21, 2005 "Plant full lengthe insert polynucleotide seqid 31279" XP002498164 retrieved from EBI accession No. GSN: ADX60436, Database accession No. ADX60436.
Jung M Etal: "Generation-Means Analysis and Quantitative Trait Locus Mapping of Anthracnose Stalk Rot Genes in Maize", Theoretical and Applied Genetics, vol. 89, No. 4, pp. 413-418, 1994.
Ashikawa, et al., Rice Blast Resistance Gene Pikm, Published Article in Genetics (ahead of print), (2008) 10.1534/genetics.108. 095034.
Brueggeman, et al., The stem rust resistance gene Rpg5 encodes a protein with nucleotide-binding-site, leucine-rich, and protein kinase domains, PNAS, (2008), 105(39): 14970-14975.
Sharopova et al. Plant Mol Biol 45: 463-481 (2002).
Badu-Apraku et al., 1987, The American Phytopathological Society, vol. 77, No. 6: 957-959.
Badu-Apraku et al., 1987, Plant Breeding, 98:194-199.
Polacco et al., 2003, Maize Genetics Cooperation Newsletter, vol. 77, "VI. A consensus genetic map, Inter-mated B73 x Mo 17 (IBM) Neighbors 5718 Loci" 141-184.
Salvi et al., 2003, Tuberosa, Phillips et Gale (eds.), Proceedings of the International Congress "In the Wake of the Double-Helix: From the Green Revolution to the Gene Revolution", 327-345.
Leister, 2004, Trends in Genetics, vol. 20, No. 3:116-122.
Young et al., 1989, Theor. Appl. Genet., vol. 77:353-359.
Zeven et al., 1983, Euphytica, vol. 32:319-327.
Opposition Against Patent EP 1 874 935, Aug. 1, 2014.
CPVO Variety data Sheet of PH705.
CPVO Variety data Sheet of PH5W4.
CPVO Variety data Sheet of PH87P.
CPVO Variety data Sheet of PH51K.
Response to Opposition Against Patent EP 1 874 935, May 22, 2015.
Flaque et al , "Linkage Mapping of 1454 New Maize Candidate Gene Loci", Genetics, vol. 170: 1957-1966 (2005).

(Continued)

*Primary Examiner* — Medina A Ibrahim

(57) ABSTRACT

This invention relates to polynucleotide sequences encoding genes that can confer resistance to the plant pathogen *Colletotrichum*, which causes anthracnose stalk rot, leaf blight and top dieback in corn and other cereals. It further relates to plants and seeds of plants carrying chimeric genes comprising said polynucleotide sequences, which enhance or confer resistance to the plant pathogen *Colletotrichum*, and processes of making said plants and seeds. The invention further presents sequences that can be used as molecular markers that in turn can be used to identify the region of interest in corn lines resulting from new crosses and to quickly and efficiently introgress the genes from corn lines carrying said genes into other corn lines that do not carry said genes, in order to make them resistant to *Colletotrichum* and resistant to stalk rot.

4 Claims, 48 Drawing Sheets

Specification includes a Sequence Listing.

(56) References Cited

OTHER PUBLICATIONS

Cone et al, "Genetic, Physical, and Informatics Resources for Maize on the Road to an Integrated Map", vol. 130: 1598-1605 (2002).
Williams, et al, The genetic structure of recombinant inbred mice: high-resolution consensus maps for complex trait analysis, vol. 2(11): 0046.1-0046.18.
Declaration of Petra J. Wolters, Ph.D. filed in Response to Opposition Against Patent EP 1 874 935, May 22, 2015.
Summons to attend oral proceedings pursuant to Rule 115(1) EPC for Patent EP 1 874 935, Aug. 10, 2015.
Lee et al., Expanding the genetic map of maize with the intermated B73 x Mo17 (IBM) Population, Plant Molecular Biology, vol. 48: 453-461 (2002).
Gardiner et al., Development of a Core RFLP Map in Maize Using an Immortalized F2 Population, Genetics, vol. 134:914-930 (1993).
Chao et al., RFLP mapping of partially sequenced leaf cDNA clones in maize, Theor Appl Genet, vol. 88 :717-721 (1994).
Coe et al, MaizeGDB Map Record p. 97584 (1995).
Davis et al, MaizeGDB Map Record p. 129755 (1996).
Springer et al, Maize Inbreds Exhibit High Levels of Copy Number Variation (CNV) and Presence/Absence Variation (PAV) in Genome Content, PLOS Genetics, vol. 5 : e1000734 (1999).
Slides that may be presented during the oral proceedings submitted on Mar. 11, 2016.
Declaration of Jean-Pierre Martinant.
Response to the Summons to Oral Proceedings dated Aug. 10, 2015.
Minutes of Oral Proceeding held on Apr. 11, 2016.
Interlocutory Decision in Opposition Proceedings Jun. 8, 2016.
Notice of Grounds for Appeal regarding Opposition to patent EP 187935; document dated Oct. 18, 2016.
Letter Dated Aug. 18, 2016 notifying Appeal against interlocutory decision of Opposition Division regarding patent EP 187935.

\* cited by examiner

Figure 2a

```
              1                                                           60
SEQ ID NO: 3  MEAALLS----GFIKTILPRLFSLV-QGRYKLHKGLKSDIKSLEKELHMIAVTID--EQIS
SEQ ID NO: 17 METAVLS----AVLRTLGPKLYAFLRDGHDLLRRDLERDVHYIRNELAMIAAAIE--EHDR
SEQ ID NO: 15 MEGAIFSVAEGTVRSLLSKLSSLLSQE-SWFVRGVHGDIQYIKDELESMNAFLRYLTVLE
SEQ ID NO: 14 MEGAVFSLTEGAVRSLLCKLGCLLTED-TWLVQGVHGEIQYIKDELECMNAFLRNLTISQ
SEQ ID NO: 16 MEGAIVSLTEGAVRGLLRKLAGVLAQE-SSPAQRVHGEVQYIKDELESMNAFLRSVSTSP
SEQ ID NO: 18 MD------IVTGAISNLIPKLGELLTEE-FKLHKGVKKNIEDLGKELESMNAAL--IKIGE 61                                                          120
SEQ ID NO: 3  LGRKDQGAVLSLSIDELHELAHQIEDSIDRFLYHVTREQQ---------ASFFRRTVRSPK
SEQ ID NO: 17 RPPPAAGDVRSAWIRGVRDLACDMEDCVDRFVH----------------RATGHGLA
SEQ ID NO: 15 D-----HDTQVRIWMKQVREIAYDAEDCIDQFTHHLGESSGI-GFLYRLIYILGKLC----
SEQ ID NO: 14 I-----HDDQVRIWMKQVREIAYDSEDCIDEFIHNLGESSEM-GFFGGLISMLRKLA----
SEQ ID NO: 16 EDAAGHDDQVRVWMKQVREIAYDAEDCIDVFVRGRSHPAAAAGDEGRLVASLRRFVRLLA
SEQ ID NO: 18 VPREQLDSQDKLWADEVRELSYVIEDVVDKFLVQV-DGIQFDDNNNKFKGFMKRTTELLK 121                                                         180
SEQ ID NO: 3  TLLS-----RQRLAAEVQFLKKIPEEAHQREKRYRVFAGLSSSTRHTESSS---CSSVSDP
SEQ ID NO: 17 SMGA-----RAKFAAVIQELRRKSEELSRLRASYAAAAGEPSCWVATGSSALTLPASSSEA
SEQ ID NO: 15 --------CRHRIAMQLQELKARAQDVSERRSRYEVM--LPKTTLQGAGPRLTRHASRHLD
SEQ ID NO: 14 --------CRHRIALQLQELKARAQDVGDRRSRYGVE--LAKATHEEAHPRLTRHASLHID
SEQ ID NO: 16 GALGVGGGDRSVAAQLRELKARARDAGERRTRYGVS--LAAAAVRGGG---GSSSSGRLD
SEQ ID NO: 18 KV-----KHKHGIAHAIKDIQEQLQKVADRRDRNKVF---VPHPTRTIA----------ID 181                                                         240
SEQ ID NO: 3  HTL-------KADVVGIDGPRDELVQQLTEEA--EGLTKQLKVISIVGIHGSGKTVLAREV
SEQ ID NO: 17 HTL-------ASDIVGMDGPRDEILE-LIGET--QG----QLKVISIVGFGGLGKTLLARQI
SEQ ID NO: 15 PQLHALFTEEAQLVGLDEPRDKLVRWVMEAD------PCRRVLAIVGFGGLGKTTLARMV
SEQ ID NO: 14 PQLHALFAEEAQLVGIDEPRNELVSWLMEED------LRLRVLAIVGFGGLGKTTLARMV
SEQ ID NO: 16 PRLHALFTEEAQLVGIDGPREELVGWVMEEE------PRLRVLAVVGFGGLGKTTLARMV
SEQ ID NO: 18 PCLRALYAEATELVGIYGKRDQDLMRLLSMEGDDASNKRLKKVSIVGFGGLGKTTLARAV 241                                                         300
SEQ ID NO: 3  YESD-V---GRQFS--LRAWVSATDRGPREVLMEILRNF-------GRPVVDSSS-------
SEQ ID NO: 17 YESDAV---AAQFH--PRIWVRAAGKNAEDVLMDILQQL-------GMPVHHCHA-------
SEQ ID NO: 15 CENPMVKGA-DFHCCP-LFIVSQTFNIRTLFQYMIRELIQRPNKAMAV----AGGKHGHT
SEQ ID NO: 14 CGSPVVKSA-DFQCCP-LFIISQTFNIRALFQHMVRELIQEPHKAMAI-----AGCKHGLI
SEQ ID NO: 16 CGSPRVKGAADFQCSPPLVVVSQTFSITALFQHLLRELIQRPRKAMAAVAAAGGGGGDLV
SEQ ID NO: 18 YE--KIKG---DFDC-RAFVPVGQNPHMKKVLRDILIDL-GNPHSDLAML-----------

301                                                         360
SEQ ID NO: 3  --------------IDQLTVDL------RKHLGEK--------RYFIVIDGM-QTDQW-STIET
SEQ ID NO: 17 --------------SNLVVNL------RNCLESK--------RFFVVIDDM-QREYWNSSFRN
SEQ ID NO: 15 MDGNMDGMERWEVAVLAEKV------RQYLLDK---------YIVIFDDIWTISAWES-IRC
SEQ ID NO: 14 TDDYLEGMERWEVAALTKNL------RRYFQDK--------RYIVILDDIWTVSAWES-IRC
SEQ ID NO: 16 AYDALQGMERWETAALASKAEGIPARQKFVHICGTITLYRYIVILDDIWSSSAWES-IKC
SEQ ID NO: 18 -------------DANQLIKKL------REFLENK--------RYLVIIDDIWDEKLWEG-INF
```

Figure 2b

```
                    361                                                        420
SEQ ID NO: 3    AFPENNVVSSRVIVTTTIRSVANSCSSS-NGYVHKMKRLSDEHSEQLFIKK------ACPT
SEQ ID NO: 17   AFPSDTGLSSIVIVTTAIQSIANACSSR-NSHVYVMRTLNEEHSRQLFLKE------ASWK
SEQ ID NO: 15   ALPDNKK-GSRVIITTRNEDVANTCCSGPQDQVYKMQRLSDAASRELFFKRIFG-SADIS
SEQ ID NO: 14   ALPDNLK-GSRIIVTTRNADVANTCCSRPQDRIYNIQRLSETTSRELFFKKIFGFADDKS
SEQ ID NO: 16   AFPDNKK-GSRIIVTTRNEDVANTCCCRPQDRIYKIQRLSDAASRELFFKRIFGMADAGA
SEQ ID NO: 18   AFSNRNNLGSRLITTTRIVSVSNSCCSSHGDSVYQMEPLSVDDSRILFWKRIF----PDEN 421                                                        480
SEQ ID NO: 3    KYSGYTRPESKEVLKKCDGQPLALVTMGQFLRKNGWPTGPNC-ENVCRDLRRHLEQDDTL
SEQ ID NO: 17   DYP-----PGSEAILKKCDGLPLALVTTAQFLQSRCQQQPLGC-AKLCDNLGKHLVTEDTL
SEQ ID NO: 15   SNE-ELDEVSNSILKKCGGLPLAIVSIGSLVASKTN-RTKEEWQKICDNLGSELETNPTL
SEQ ID NO: 14   PTD-EFEEVSNSVLKKCGGLPLAIVNIGSLLASKTN--RTKEEWQKVCNNLGSELENNPTL
SEQ ID NO: 16   PDDDELKQVSDSILKKCGGLPLAIVSIGSLLASKPN-RSKEEWQKVCDNLGSELESNPTL
SEQ ID NO: 18   GCLNEFEQVSRDILKKCGGVPLAIITIASALAGDQKMKPKCEWDILLQSLGSGLTEDNSL 481                                                        540
SEQ ID NO: 3    ERMRRVLIHSLSSLPSHVPKACLLYFGMFPCDHPIKRKSLMRRWLAEGFVQTQPSSS----
SEQ ID NO: 17   ARMKRVLVHHYSSLPGHVIKACLLYLGIFPSGHPVRRKTLIRRWSAEGFVGADHHRSSLD
SEQ ID NO: 15   EVAKQVLTLSYNDLPYHL-KACFLYLSIFPENYVIRRGPLVRRWIAEGFVNQ-RHGLSME
SEQ ID NO: 14   EGVKQVLTLSYNDLPYHL-KACFLYLSIFPENYVIKRGPLVRRWIAEGFVSQ-RHGQSME
SEQ ID NO: 16   EGTKQVLTLSYNDLPYHL-KACFLYLSIFPENHVIKRGPLVRMWIAEGFVTQ-RHGLSME
SEQ ID NO: 18   EEMRRILSFSYSNLPSHL-KTCLLYLCIYPEDSKIHRDELIWKWVAEGFVHHENQGNSLY 541                                                        600
SEQ ID NO: 3    -----ENFNTLIDRNIIEPIGICNDDQVKTCKTYGMMHEFILLMSTSHDFITLLCNNKVE-
SEQ ID NO: 17   --VAIDSFEELVNRSIIQPVDVSSNTEVKTCQTHGMMLEFILHKSICDNFITFLYGQARL-
SEQ ID NO: 15   EVAESYFDEFVARSIVQPVKIDWSGKVRTCRVHDMMLEVIISKSLEENFASFLCDNGHPL
SEQ ID NO: 14   QLAESYFDEFVARSIVQPVRTDWTGKVRSCRVHDLMLDVIVSRSIEENFASFLCDNGSTL
SEQ ID NO: 16   QVGERYFDEFVSRSMVHLVRIDWSGKVRSCKVHDIMLEVIVSKSLEENFASFFCDNGTEL
SEQ ID NO: 18   LLGLNYFNQLINRSMIQPI--YGFNDEVYVCRVHDMVLDLICNLSREAKFVNLLDGSGNSM 601                                                        660
SEQ ID NO: 3    --HKYVRRLSLHHHS-ATSGSF-SVID-LSLVRSLMVFGEAGKTILSFRKYELLRVLDLE
SEQ ID NO: 17   --PDKIRCVSIQQNS-GSKTRVDSDID-LSLVRSLTIFGKAHKSFLNFSRYKLLRVLDLE
SEQ ID NO: 15   VCHDKIRRLSIHNS-HNSVQRTRVSV---SHVRSFTMSASVEEVPMFFPQMRLLRVLDLQ
SEQ ID NO: 14   ASHDKIRRLSIHSS--YNSSQKTSANV---SHARSFTMSASVEEVPFFFPQLRLLRVLDLQ
SEQ ID NO: 16   VSHDKIRRLSIRSSSYSSAQRTSNSV---AHVRTFRMSPSIDNIPFFFPQLRLLRVLDMQ
SEQ ID NO: 18   SSQGNCRRLSLQKRNEDHQAKPITDIKSMSRVRSITIFPPAIEVMPSLSRFDVLRVLDL- 661                                                        720
SEQ ID NO: 3    QCT-DLEDD------HLKDICNLFLMKYLSL-GETIRSLPKEIEKLKLLETLDLRRTK-VK
SEQ ID NO: 17   ECD-ELEDE------HLKKICKRLLLKYLSL-GRGITVLPKEIAKLKFLETLDLRRTV-IK
SEQ ID NO: 15   GSSC-LNNST------LNYICKFYQLKYLTLRKTNIGKLPRLIGNLKYLETLDIRATR--IK
SEQ ID NO: 14   GCSC-LSNET------LHCMCRFFQLKYLSLRNTNVSKLPHLLGNLKHLETLDIRATL-IK
SEQ ID NO: 16   GSRC-MSNKN------LDCICRFFQLKYLSLRNTSVSILPRLIGNLNHLETLDIRETL-IK
SEQ ID NO: 18   -SRCNLGENSSLQLNLKDVGHLTHLRYLGLEGTNISKLPAEIGKLQFLEVLDLGNNHNLK
```

Figure 2c

```
              721                                                            780
SEQ ID NO: 3  TLPIEVLLLPCLLHLFGKFQFSDKIKITSD----------MQKFFLTGQSNLETLSGFITD
SEQ ID NO: 17 FLPIQVLELPCLIHLFGVFKIQDADQQMRK----------L-KSFLTEKSKLETLAGFVTD
SEQ ID NO: 15 RLPASASNLSCLKHLLVGHKVQLTRTTSVKCFRPDSGLEMTAGVVKNMMALQSLAHIVVK
SEQ ID NO: 14 KLPASAGNLSCLKHLFAGHKVQLTRTASVKFLRQSSGLEVATGVVKNMVALQSLVHIVVK
SEQ ID NO: 16 KLPSSAANLTCLKHLLAGHKEQLTRTSSVKFLRPSSGLKMSHGVIRNMAKLQSLVHVEIK
SEQ ID NO: 18 ELPSTVCNFRRLIYL-----------------NLF--GCPVVPPVGVLQNLTSIEVLRGILVS 781                                                            840
SEQ ID NO: 3  GSQGLPQMMNYM-NLRKLKIWFERSKRS--TNFTD----LVNAVQKFIHDDKESNDPRSL
SEQ ID NO: 17 RCQTFPQLMKHMTNLAKVKIWCENTADA--SSSSNSDVHLSEAIQEFIQRGTDVNDVRSL
SEQ ID NO: 15 ERPAVLSEIGQLQKLQKLNVLFRGVEEN-WNAFLQSLVKLTGSLRSLSIHILDEKE-HSS
SEQ ID NO: 14 DKSPVLREIGLLQNLTKLNVLLRGVEEN-WNAFLESLSKLPGPLRSLSIHTLDEKE-HSL
SEQ ID NO: 16 EHPSVFQEIALLQNLRKLSVLFYGIEVN-WKPFLELLNMLSGSVRSLSIDIFDAQG-N-I
SEQ ID NO: 18 VNI-IAQELGNLERLRVLDICFRDGSLDLYKDFVKSLCNLH-HIESLRIEC--NSR-ETS 841                                                            900
SEQ ID NO: 3  SLHFDDGTENILN-SLKAPCYLRSLKLKGNLL--ELPQFV-----ISMRGLREICLSST-KL
SEQ ID NO: 17 SLDVGECSQEFLNFSLGDSCYLSSLKLKGNKICRLPPFV-----TSLAVLTDLCLSSSDRL
SEQ ID NO: 15 SLEYLALIAE---SPPLFIRNF---SLK----GKLQRLPPWI-----PSLRNVSRITFRDT-GL
SEQ ID NO: 14 SLDNLAFV-E---SPPLFITKF---SLA----GELERLPPWI-----PSLRNVSRFALRRT-EL
SEQ ID NO: 16 SISSLEMLSSLVSPPIFITSF---SLT----GKLGSLPPWV-----ASLRSVSRLTLRRS-QL
SEQ ID NO: 18 SFELVDLLGERWVPPVHFREFVSSMP-----SQLSALRGWIKRDPSHLSNLSELILSSVKDV 901                                                            960
SEQ ID NO: 3  TSGLLATLANLKGLQHLKLI------ADVLEDFIIEGQAFLGLLHLCFVLERATL-------P
SEQ ID NO: 17 SSDVLAALSNVRALRYLKLI------ARHLDRFVIERGDLQSLRRLHIVVVSMTTMSKQQP
SEQ ID NO: 15 HAEAIGVLGDLPNLLCLK-LYQRSYADD---HIFFAHGNFLKLR-----MLVIDNMENIRNV
SEQ ID NO: 14 HADAIGVLGDLPNLLCLK-LYHKSYADN--CIVFCHGKFVKLK-----LLIIDNLERIEKM
SEQ ID NO: 16 RADAIHVLGGLQNLLCLK-LYHKSYADD---RLVFPQGGFARVK-----LLIDDNLVNLEKL
SEQ ID NO: 18 QQDDVEIIGGL---LCLRRLFIITSTDQTQRLLVIRADGFRCT----VDFRLDCGSATQI 961                                                            1020
SEQ ID NO: 3  IIEGGALPYLISLKLICKDLVG---LGDIKINRLK--CLKEVSLDHRVASETREIWEKAA
SEQ ID NO: 17 EIQEGALPNLESFHLLCKDLDGPCGHGGIRIDSLGLGCLREIVLDDGVRETAKEQWKDAA
SEQ ID NO: 15 HFEKGSVPNLE-------------------------WLTIAFLQEP--KDGITG-----------
SEQ ID NO: 14 QFDAGSVTNLE--------------------------RLTLSFLREP---KYGISG----------
SEQ ID NO: 16 HFNEGSMPNLE--------------------------RLTLSFLREP--KDGISG-----------
SEQ ID NO: 18 LFEPGALPRAVRV-----------------------WFSLGVRVTK--EDGNRG-----------

1021                                                           1080
SEQ ID NO: 3  EKHPNRPKVLLVNSSDESEIKAVDCSVASRPAVSEANGTSPMSEVD--VREDDIQMI-----
SEQ ID NO: 17 RRHPKRPKVVFVGAGDVVDRRRVGAAAAAAPAAGESNSAMAPAAVASVVAAGDVKRPARE
SEQ ID NO: 15 ---------LE------NLLKLKEIE----------------------FFGDIILSMVTKV
SEQ ID NO: 14 ---------LE------NLPKLKEIE----------------------FFGDIILSVVTKV
SEQ ID NO: 16 ---------LN------NLLKLKEVE----------------------FFGNIVSSVVSKV
SEQ ID NO: 18 ---------FDLGLQGNLFSLREFVS---------------------VYMYCGGARVGEAKEA 1081                                                           1128
SEQ ID NO: 3  ---LNQGLSAAAEKQMNCAVQPSSKAELNSDFNNISFPEVALGLTEL.
SEQ ID NO: 17 ESDISAALASLPAK-MARLLGAASIHQSSGTQGELSCGGNGASQRHFS
SEQ ID NO: 15 ASCMK-----AHPNR---PRVIGDKWNNVT-------------------EYA
SEQ ID NO: 14 ASCVK-----AHPNH---PRVIGDKWNIVT-------------------EYA
SEQ ID NO: 16 VSCVK-----DHPNH---PRVVGDKWNIVT-------------------VYN
SEQ ID NO: 18 EAAVR
```

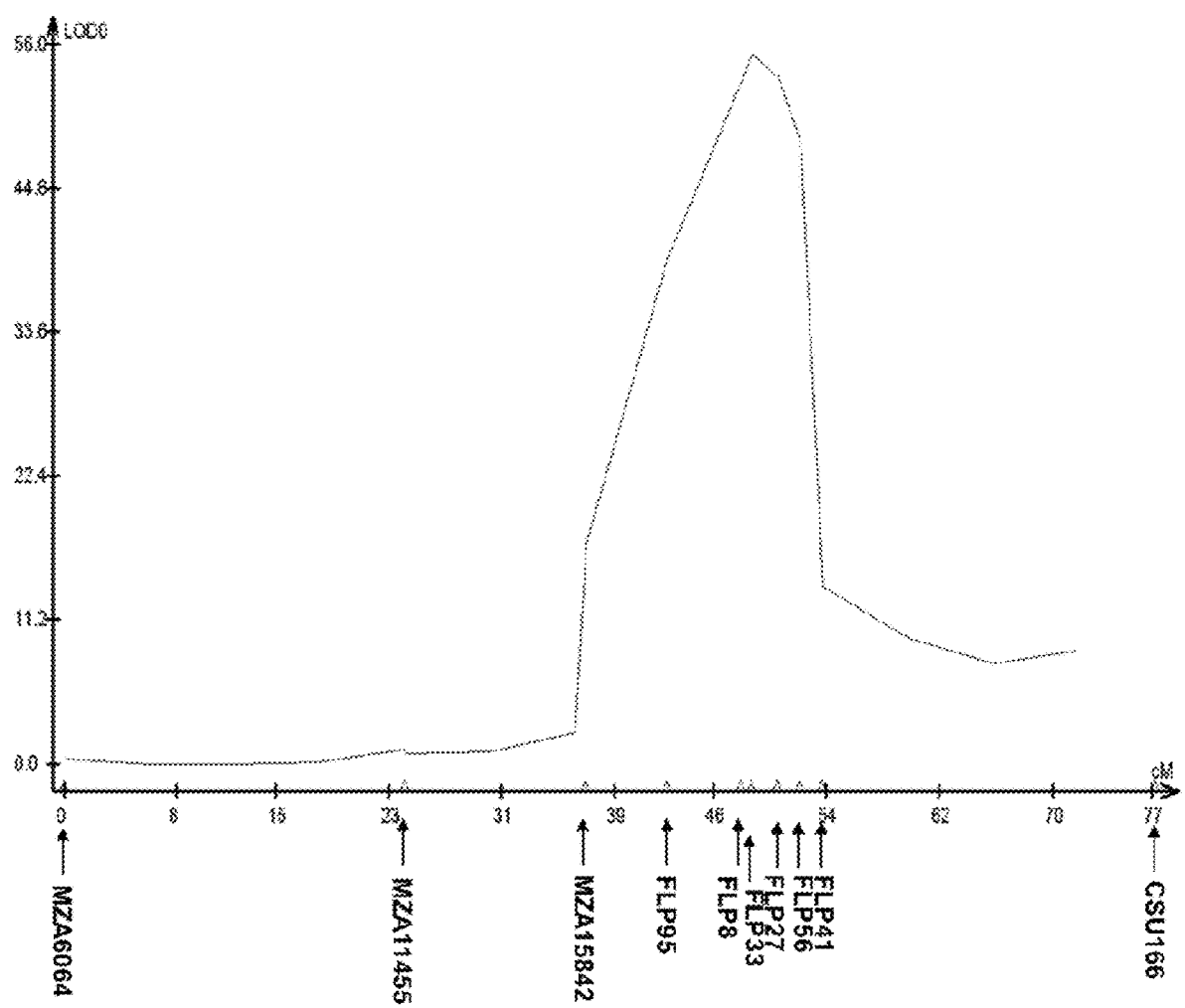

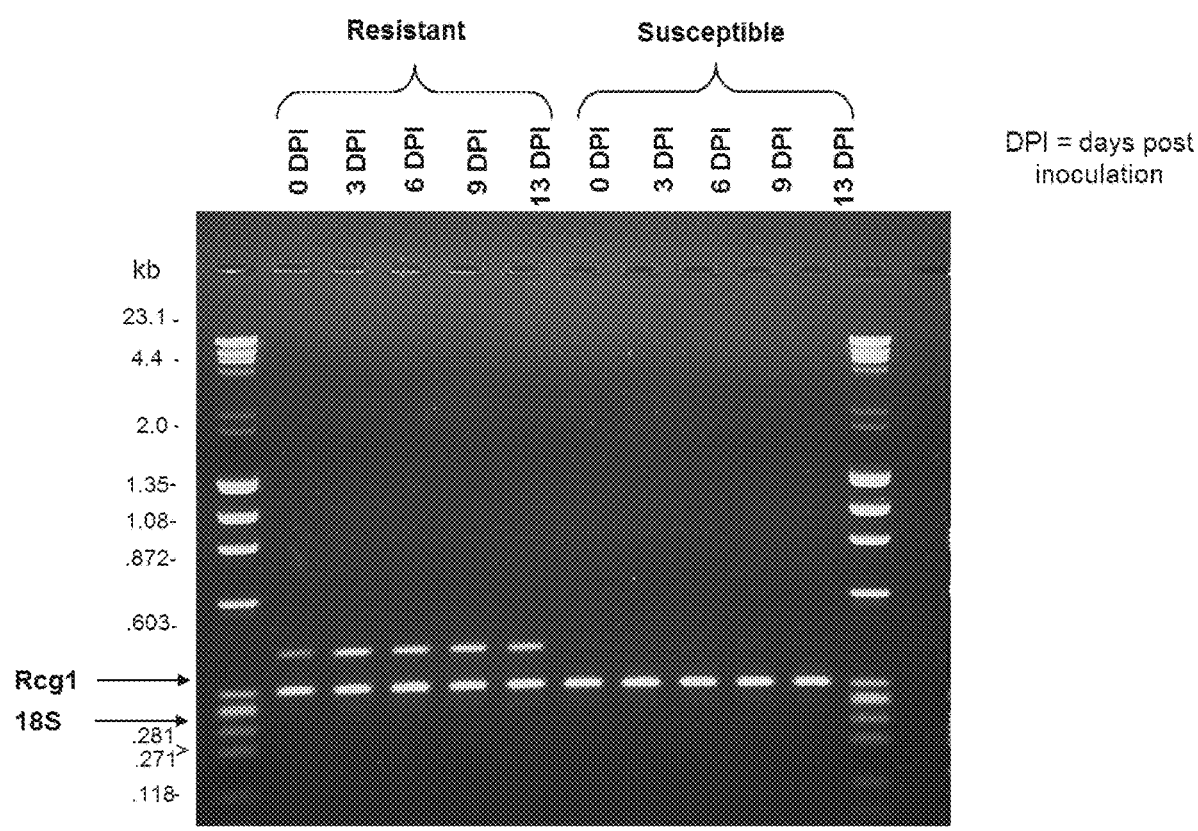

Rcg1 Insertion Site Mo17 and B73

50,330 bp of Rcg1 Non-colinear Region set forth in SEQ ID NO: 137

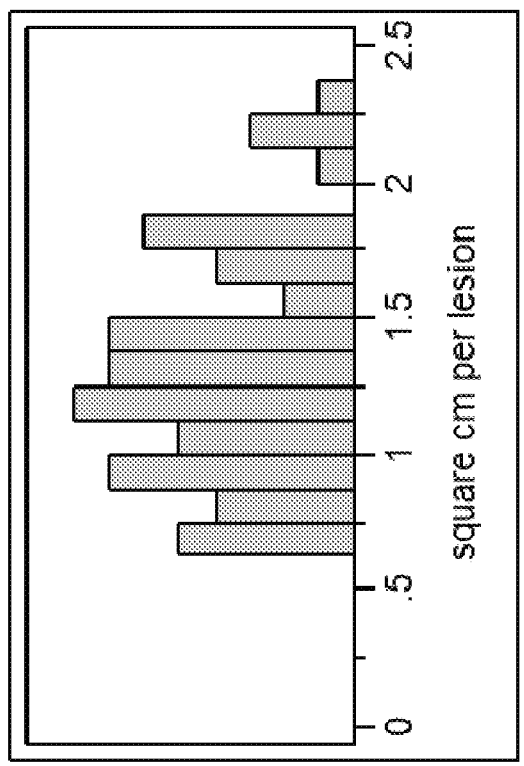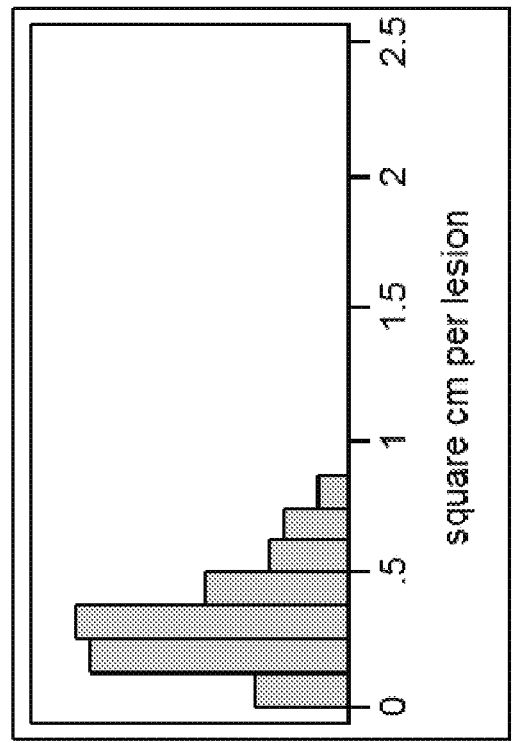
Figure 10

```
Alignment Report of 'Rcg1b vs NB-LRRs_ClustalW.meg' - ClustalW (Slow/Accurate, Gonnet) : Thursday, June 07,
2007 10:43 AM 10        20        30        40        50        60        70        80
                   +---------+---------+---------+---------+---------+---------+---------+---------+
SEQ ID NO: 246     ------------------MEAAVSSSTGAMGPLLRKLELL--LAP-ESRLRKRVKDGIGLLKEDLE-EVSFPLVDLSM---LETPS        61
SEQ ID NO: 250     ------------------------MEGSMFNLPGRLDRLLRRH-GSMLPKGAEEEIPLIKQDLEEIISVLHGHCSKPKLEDHA        58
SEQ ID NO: 251     ---------------MEAPPLAAPICASQGAMGSLLGKMEELLVAPDGSRLPKGVKDRMLLGGDLG-VVAAYLADLSE--LEDPP        68
SEQ ID NO: 247     -----------------------MDAPVSFSLGAMGPLLRKLDSLPVAP-EIRLPEPLKDGIELLKEDLE-EIGAALVEQSM---VDSPS        62
SEQ ID NO: 248     ---------------MEAPPLAAPICASQGAMGSLLGKMEELLVAPDGSRLPKGVKDRMLLGGDLG-VVAAYLADLSE--LEDPP        68
SEQ ID NO: 249     MYGVWFASGRNMEMMEAPVSASQGAMRSLPRKLESLLSGP-NQGLRPEEKKKLRFLQADLQGLIDSYLFEPSE--VESPA        77

90       100       110       120       130       140       150       160
                   +---------+---------+---------+---------+---------+---------+---------+---------+
SEQ ID NO: 246     PRAKCWMEEARELSYHVEDFVDELMLMLTDAG-------ANIRAVNRHRVGRVKIALLTAPPRRSGSTRVTKIAELRALVWQA      137
SEQ ID NO: 250     MVVRCWMKEVRELSYDIEDCIDQYEHAATATRSHTGPNICRRKFNQRHGKMIPWVPWKLKQR-LWMANKIREFSLRTQEA      137
SEQ ID NO: 251     PTAKRWMREVRELSYDIEDYIDEFCAAPRPGR----RANTMARFVCRIGRVKVARLPKRLKRH-QQMGKMVSQFRIYVEEA      144
SEQ ID NO: 247     HRARYWMDEVRDLSYHIEDCIDTMFSMRCGGDD---GKPRSVRRHKVGRVKVDGFSKTQKP---CTRLARIAELRALVREA      137
SEQ ID NO: 248     PTAKRWMREVRELSYDIEDYIDEFCAAPRPGR----RANTMARFVCRIGRVKVARLPKRLKRH-QQMGKMVSQFRIYVEEA      144
SEQ ID NO: 249     STASFWMKDVRDLSYDIDDFIYELGHVAVS------GARIGAAQIQKVPGVKISRFPDKLKRR-QWISDEISGFRTRVKEA      151

170       180       190       200       210       220       230       240
                   +---------+---------+---------+---------+---------+---------+---------+---------+
SEQ ID NO: 246     TERFERYQ-LE-----------D---Y-------------------------------------------------------      149
SEQ ID NO: 250     LQRHTMYNNLGGITIASTTGGDVCSATPWHPTQFREHTDNVCSVGIDADGMEAALNDLNKLKNLLASIPTASLVQFREHA      217
SEQ ID NO: 251     IERHGRYG-LD----------CCDHRR---------------------------------------R-------------      161
SEQ ID NO: 247     SERHERYQ-LG----------DGRAS------------------------------------------------------      152
SEQ ID NO: 248     IERHGRYG-LD----------CCDHRR---------------------------------------R-------------      161
SEQ ID NO: 249     IQRHKTY--LG----------GCRWRP-----------------------------------------------------      166
```

Figure 31b

```
SEQ ID NO: 246                                                          ----CSSPSDMNLITQHRRAPALYGDEANLVGIEASRIKLIEMLTGEAEQQPKVVFIV  203
SEQ ID NO: 250 NKVRHIHPDVEAILNKLKNIPTGITTSTTRGDVSSTSSRQPTRFMESAGLVGINAAVNKLENLLDVCGEEKLKVVSIV  297
SEQ ID NO: 251 -----------------------YVSFGPMLPSRPYGEEDAQ-------LVIDGRVSEFIERLANDEDQKLKVVSVV  208
SEQ ID NO: 247 -----------------SSSSSSHRVFTAHGQVPAPCR-----NLVGMDEPKTKLTNMLTDEAELHMKVVCIL       203
SEQ ID NO: 248 -----------------------YVSFGPMLPSRPYGEEDAQ-------LVIDGRVSEFIERLANDEDQKLKVSVV  208
SEQ ID NO: 249 -----------------SSSSSQHSAPSPCGRAAIR-------LVGMDSPVEQLCGWLANDGQPEHKVASIV       214

SEQ ID NO: 246 GPVGVGKTTLAKEIFGELRGKFELRAFVHASRKLDMRRLLGGILSQVQPHHQLPSVAGTVQILIDSIQEQLRDKRFFIVI  283
SEQ ID NO: 250 GVGGVGKTTLANKLYCKLQRQFECWAFVQTSQKTDMRLLINILSQVQPHQSPDNWK---VHSLISSIRTHLQDKRYLIII  375
SEQ ID NO: 251 GSSGIGKTTLAKLLYNRIGGQFDCRAFVRISRKPDMKRVFREMFFQLQRKQPPDDYK---ELALIDSIREYLQDRRYLIII  286
SEQ ID NO: 247 GSAGIGKTTLAEQVYRKLRWQFDCHAFVRASRKPDMRRLLGAILSQVQLRIRISDTS-TVQSLIDNLWEYLQKKRYFIVI  282
SEQ ID NO: 248 GSSGIGKTTLAKLLYNRIGGQFDCRAFVRISRKPDMKRVFREMFFQLQRKQPPDDYK---ELALIDSIREYLQDRRYLIII  286
SEQ ID NO: 249 GTSGVGKTTLARQVYHKLGGQFECRAFVQASPKQDMKMLLTSILSQVRRHHLPDSFD---VHKLLFEIEAHLQDKTYIIVI  292

SEQ ID NO: 246 DGLWEETAWDIVRDAFPEGNNYSRIVATTENMNVALKCCSYMTYNILKMKPLGIKDSAYLFFNRVFGSDQQCPDELKEVS  363
SEQ ID NO: 250 DGLWATSTWDVIKCALPDGNSSSRILTTTEIEDLALQSCSYDLKFIFKMKPFGEGDSRKLFFSIVFGSHSKCPPEVSETL  455
SEQ ID NO: 251 DDLWAASVWDLINQAFPEVILSSRIVIITQVEDLALTCCCYDTEYIFEMKPMDDEHSTTLFLQRFFGFVSDCPQQFKEVS  366
SEQ ID NO: 247 DELYETATWDIITSAFPEDNNCSRIMTTAGIEGVALECCSYHSVNIFKMIPLGLDDSAKLFFNRVFGSEQQCPYELNEVS  362
SEQ ID NO: 248 DDLWAASVWDLINQAFPEVILSSRIVIITQVEDLALTCCCYDTEYIFEMKPMDDEHSTTLFLQRFFGFVSDCPQQFKEVS  366
SEQ ID NO: 249 DNLQASSTWDIINHALPKENCCSRILTTTEVDAIAQTCCADTSKYIFKKESLSEDESRELFLGTVFGHEAGCPQVLKEVS  372
```

Figure 31c

```
                       490       500       510       520       530       540       550       560
                 ----------+---------+---------+---------+---------+---------+---------+---------+
SEQ ID NO: 246   YGIIRKCCGLPLSIIHVAGLLASIDYS---GLWYHVHDRLYSILNRSHTVEEIQKKILDLSYNSLPHCLKTCLLYFNMYPE      441
SEQ ID NO: 250   YDIVRKCGGLPLAIVTVASLLASLLEK--QEQLDYINKSLGYGLMANPTLEG--MKQLLNICYNNLPQHLKVCMLYLSMYQE      533
SEQ ID NO: 251   NKIVQICGGLPLATISLASLLASLLASQPVILMDLCLYIRNSLSSAFRTNSSIEG--TRQVLNLSYNNLPHYLKTCLLYLNMYPE    445
SEQ ID NO: 247   YRITAKCGGLPLAVIIAGLLASLPCK--TELWYNIDGCLCSSVTTDIDLDEILKEIISLGYDNLPHYLKTCLLYLSLYSE         441
SEQ ID NO: 248   NKIVQICGGLPLATISLASLLASQPVILMDLCLYIRNSLSSAFRTNSSIEG--TRQVLNLSYNNLPHYLKTCLLYLNMYPE        445
SEQ ID NO: 249   NEIIKRSGGLPLAIIILASLLVGQPASSIEHWNHIKNSLSSDSSTNTSLEG--IKQVLNLGYEYLPHYLKACMLYLCMYEE        451

570       580       590       600       610       620       630       640
                 ----------+---------+---------+---------+---------+---------+---------+---------+
SEQ ID NO: 246   GYIMWKVHLVKQWIAEGFINPAEGKDREEIAEGYFEELVSRGMVQPMKIDYNGEVLSCTVHHTIFDLINYNSKEEEFIAG         521
SEQ ID NO: 250   DHIWKDDLVSQWIAEGFICATEGHDKEEISRAYFDELVGRKIIQPVHIDDSGEVLSCVVHHMVLNFVTYKSIEENFIIA         613
SEQ ID NO: 251   GYKICKDDVVEKWVAEGFIDQIEGRDLEKVAGSYFIDLIDRRFLQPSRLNYNNEVSTCTIHDEVRDLIAYKSVEENFVLV        525
SEQ ID NO: 247   GFIWTADLLKQWISEGFIAVIDGEDIEEVAESYFYNLVNRGMIQSVKTKYNNQVL-CTVHHTVFDLIIHKSKEEKFISA         520
SEQ ID NO: 248   GYKICKDDVVEKWVAEGFIDQIEGRDLEKVAGSYFDELIDRRFLQPSRLNYNNEVSTCTIHDEVRDLIAYKSVEENFVLV        525
SEQ ID NO: 249   DCIIWKDDLVKQWIAEGFIHAMDGNGGKEVARSYFDELVNRGMIQPMDINCNDEILSFSVHTMVLHFIRYKSVEENFSIA        531

650       660       670       680       690       700       710       720
                 ----------+---------+---------+---------+---------+---------+---------+---------+
SEQ ID NO: 246   IDYSQPITGLATKARRLSFRFSSAKYAKQ---PTRITTSQLRSLGFFGFSKCMPPIVEFKHLRVLVLDFWGSHDG--------      593
SEQ ID NO: 250   IDHSQATIRFADKVRRLSIHFSNVEDATP--PTSMRLSQVRTVAFFGVLKYMPFVMEFRLIKVLVLHILGDEDS--------     686
SEQ ID NO: 251   LDFYRKDVELSDKVRRLSVHFGDIKYAKI--PTNIRTSEVRSLTFFGLCKCMPSLTEFKLLRVLNLQLSGHVGD--------     597
SEQ ID NO: 247   IDYSQTMPGNSLEARRLSFHFSNTRYATE--VAGITLSQVRSFAFLGLLKCMPSIMEFKLLRVLIEFWGDNHG--------      592
SEQ ID NO: 248   LDFYRKDVELSDKVRRLSVHFGDIKYAKI--PTNIRTSEVRSLTFFGLCKCMPSLTEFKLLRVLNLQLSGHVGD--------     597
SEQ ID NO: 249   LDHSQTTIRLADKVRRLALHFGNVEHATPPMPASMRLSQVRSLAFSGLLKCMPSFVEFRFIQVLILKLWADPDNRSDNFI       611
```

Figure 31d

```
                         730       740       750       760       770       780       790       800
                    ----+---------+---------+---------+---------+---------+---------+---------+
SEQ ID NO: 246      ------------------------------HMSLNLSRIYILFQLRYLKISG-DIMVELPAKMQGLHYLETLEIDARLSAVPLDIVH  649
SEQ ID NO: 250      G----------------------------------IFDLTKISELVRLRYLKVTS-NVTVKLPTQMQGLPYLETLKIDGTISEVPTDIY-  740
SEQ ID NO: 251      -----------------------------------ELLDLSGISELFQLRYLKIAC-DIRTELPSQMRGLKYLETLQMDTLLTAVPWDIIF  652
SEQ ID NO: 247      -----------------------------------CMSFNVARICRLFQLRYLKISS-QIIIELPAQIRGLKYLETLEIDARVTAIPSDIIH  648
SEQ ID NO: 248      -----------------------------------ELLDLSGISELFQLRYLKIAC-DIRTELPSQMRGLKYLETLQMDTLLTAVPWDIIF  652
SEQ ID NO: 249      GSDDLSGNITEPDDLSDNLTEHDDLSLNLSEISELFRLRYFHLDACHMSVELPTQMKRLKDLVACEIDANVTAVPSDIVD  691
                    ----+---------+---------+---------+---------+---------+---------+---------+
                         810       820       830       840       850       860       870       880

SEQ ID NO: 246      LPSLLHLSLRAATKLPDGIGHIKSLSTLLYFDLRCNSEDNIRSLGQLTNLRHLHLTCSTVLSSDHLKRKLIPLAFSLGKL  729
SEQ ID NO: 250      LPRLLHLTLPAKTNLPSGIVHMTSLRTIGYFDLSCNSAENLWSLGELSNLRDLQLTYSEIHS-DNLKDNMKYLGSILGKL  819
SEQ ID NO: 251      LPCLLHLHLRFDMNLIDLMGHMTPPSELG--SSSSNSSPSGGIISNLNNVRDIHLTFCALPS-KHLERNMEILGSLLGRL  729
SEQ ID NO: 247      LRSLLHLYFQDGIVLPDGIGCIRSLRTLKYFDLGSNSEENIRSLGQLTNLRDLHLTCSAPKSNQQAKRNLVILASYTGKL  728
SEQ ID NO: 248      LPCLLHLHLRFDMNLIDLMGHMTPPSELG--SSSSNSSPSGGIISNLNNVRDIHLTFCALPS-KHLERNMEILGSLLGRL  729
SEQ ID NO: 249      LPGLFFLSIPSEARLPTGIGRMTSLCTLGIIDLSNNSTENIMCLGELTNLQDLRLTCSTLQA-DNLEKNLECLGLIIRKL  770
                    ----+---------+---------+---------+---------+---------+---------+---------+
                         890       900       910       920       930       940       950       960

SEQ ID NO: 246      GNLKSLTLTPDALR------------SGISSPSIFLQKLELLPPICFFSRLPACFGELHKLRILKIVVKELQ  797
SEQ ID NO: 250      RNLTSITLSPPGSS---CPDTLHIDRTRINVDGWSSVSSPPALLQRFELLPCVCIFSNLPNWIGQLGNLCILKIGIREVT  896
SEQ ID NO: 251      GNLKNLTLVSSSSQ--KKIAASGASEVTILWDNLA------PPPLLQRFEWLLHSCIFYRVPKWIGELGNLCILKIAVRELV  803
SEQ ID NO: 247      GNLKSVKFSPGDSG---MDISFLFYGIGISVD-RSRTASSLPFSVRTLELPSICIFARLPDWIGQLRKLHTINLAVRELI  804
SEQ ID NO: 248      GNLKNLTLVSSSSQ--KKIAASGASEVTILWDNLA------PPPLLQRFEWLLHSCIFYRVPKWIGELGNLCILKIAVRELV  803
SEQ ID NO: 249      SNLKCVTLVPVVSSHVKTQDDASSSRMTISWDGFTTVSLSPALLQRLELSRRCFILSSLPEWTKDLTNLGILKMAVSKVS  850
```

Figure 31e

```
                         970        980        990       1000       1010       1020       1030       1040
                ----------+----------+----------+----------+----------+----------+----------+----------+
SEQ ID NO: 246  GNDINNIAGLPSLVIFSLYVRTALTGTVIFSTMSFPALKYFRFTCGVTCLAFQEGAMHRLQRLKLCFNAHGGKNHSRVID   877
SEQ ID NO: 250  SNSIDVLGVLPKLTVLSLYVHTKPAERIVFDNAGFSILKYFEFICSVAWMKFEMGAMPSLRKLKLGFDVHIADQHDIIPV   976
SEQ ID NO: 251  KNSVDILRGLIPALMALSLNVHRASVENIFFDKVGFSVLKFYKYNCSVPWLKFEAGAMPNLRKLKLGFSA-LGDLYGTAPI   882
SEQ ID NO: 247  ENDIDSLAGLPDLIVLSMHIMKAPMERIVFNRKAFPVLKYFKFICGTLRMAFQAGAMANLHRLKLGFNAHKGEKYDNILV   884
SEQ ID NO: 248  KNSVDIIRGLPALMALSLNVHRASVENIFFDKVGFSVLKFYKYNCSVPWLKFEAGAMPNLRKLKLGFSA-LGDLYGTAPI   882
SEQ ID NO: 249  SEDVVILKGLPSLTALSLFVWTAPTRRIIFDNEGFLVLKYFKFVCVAPCLSFLDGAMPKVHNLKLGFNANRMEQYSLVAA   930

1050       1060       1070       1080       1090       1100       1110       1120
                ----------+----------+----------+----------+----------+----------+----------+----------+
SEQ ID NO: 246  GIEYLLNLQEVSGQIGVLPGGDESNMRVVKLSFEDTIRKHPRCLR-FNLQLVDFIEEEYPPLVKLHQRQQDEYEIEEN--   954
SEQ ID NO: 250  GIEHLSGLEEISAKIRVACTAHDHCRRFAESALTNAFMMHPGRPS-VNIRCVDWTFHDKDNDCVGTREEECRTPMKQEHF   1055
SEQ ID NO: 251  RIGHLLGLKEISVKIHGAS------VDAESALTSAVSNHPSNPR-INVQLVDKIFYGDRVTKEKDHGSE----------   944
SEQ ID NO: 247  GIEHLLNLKKIAVRIGGAAEAKESDRMAAEAALKEAIRKHLMFLDDLDIARVECVKEEYKCIKKKHKIKIEDSISEKNG-   963
SEQ ID NO: 248  RIGHLLGLKEISVKIHGAS------VDAESALTSAVSNHPSNPR-INVQLVDKIFYGDRVTKEKDHGSE----------   944
SEQ ID NO: 249  GFEHLIGLKKISIKIGGAG-ADECDRRSAQLVLTDAISKHPNTSI-ISVQWVNSKFCGEQDVNAGE---------------   994

1130       1140       1150       1160       1170       1180       1190       1200
                ----------+----------+----------+----------+----------+----------+----------+----------+
SEQ ID NO: 246  ---DSADGNTKHTDGRYGFNRFIFSNSSLVDLEADFQAQSRSTSNDLPIPYNKQLDWRKAVNHIRYKRLSRSCLTFLVSN   1031
SEQ ID NO: 250  VKEDLSEKSAVLQNEHDEEAHKFVDRRYYPIMDAAEIRRCP---------WSVNEEQEQPVLIYDARTKISQSSSMHS   1124
SEQ ID NO: 251  EEQNAIMSANFDEYHQTQDKES----SDANKQVGSI----------VPLPREQEHGILEHDEYAPKDPDKYKQS       1004
SEQ ID NO: 247  DSKKQHSVEKKAVWGKTMKNIADSGVFPEDYTMSREQR-VAEGFVVGIEKCRAEDAAERIIRNVPVDYDGLGQVSTS   1039
SEQ ID NO: 248  EEQNAIMSANFDEYHQTQDKES----SDANKQVGSI----------VPLPREQEHGILEHDEYAPKDPDKYKQS       1004
SEQ ID NO: 249  ------SSSYQQDTGNLLFPSHLTLCPFNSVCC                                              1021
```

Figure 31f

```
                            1210       1220       1230       1240       1250       1260       1270       1280
                        ----+----|----+----|----+----|----+----|----+----|----+----|----+----|----+----|
SEQ ID NO: 246  KLLGVEQSFALWEERNELLGVHEHGDTHHISGIDEYNEVEDGVVAVEGEPKELRIGEALEGLTETSCLSMTTLEGFTGTS  1111
SEQ ID NO: 250  EFWAAVQRLTGPAATPAKTKRH--------------------------------LHLTTSPE---LEDGFLPVRSLV--  1166
SEQ ID NO: 251  DIRSVSSMYPWHLKFLGALSIHGGTRLATAPRKAEDAYISYAM-------------KGNMQDSVH---MPDSSCYLSMLV--  1068
SEQ ID NO: 247  KIQDHLPELAPRAVQNEKFGSSN--DLSIMIQINKYARLPS---------------YEWRD--T----DISKLNFRLLR--  1095
SEQ ID NO: 248  DIRYVHSI                                                                          1012
SEQ ID NO: 249                                                                                    1021

1290       1300       1310       1320       1330       1340       1350       1360
                        ----+----|----+----|----+----|----+----|----+----|----+----|----+----|----+----|
SEQ ID NO: 246  SLSMASDDDTSNTTMEEMFISPDRQLKRKIKSWMRGAFLGSGSLGMVYEAISQEGVFFAVKEVSLLDQGSKAQQSILALE  1191
SEQ ID NO: 250  -FPSAPDPRCN-------------------------------------------MKKKKMRAGPGGGRAVRSNWAPK    1199
SEQ ID NO: 251  -LPMALDMKSHLYESFEVTLARANTW------------------LYASQASGVPIKLMSVQSDDLLTKISRVGDATSATVNSGLLPD  1136
SEQ ID NO: 247  -APMLLEAVTARCHLLDLIL------------------------IG-S--------------NNITVLDLG---RPTITKLP  1134
SEQ ID NO: 248                                                                                    1012
SEQ ID NO: 249                                                                                    1021

1370       1380       1390       1400       1410       1420       1430       1440
                        ----+----|----+----|----+----|----+----|----+----|----+----|----+----|----+----|
SEQ ID NO: 246  KKIELLSQLQHENIVHYYGTEKGESKLYIFVELVTQGSLSSLYKKYKLQESQVCWYTSQILNGLVYLHKQNVVHGDIRCA  1271
SEQ ID NO: 250  S                                                                                 1200
SEQ ID NO: 251  LSNATLEDYQG---------YNTEVVKAARLWYSSIGGE----MPLEITPKVGDTKLGFAISRTEEGFIYISSVLQDDNDSETP  1207
SEQ ID NO: 247  ASIECLPNLR------YLRLQG---TQLKSLSEVIVK----MPTIRGLDIKNT----KTEELPQGILRMKKLSHLSMGEKQK  1199
SEQ ID NO: 248                                                                                    1012
SEQ ID NO: 249                                                                                    1021
```

Figure 31g

```
                      1450       1460       1470       1480       1490       1500       1510       1520
                 ----+----|----+----|----+----|----+----|----+----|----+----|----+----|----+----|
SEQ ID NO: 246  NILVHANESPKLADFGLAKEMSNILTLRSCERNVYWMAPEFINPKKTFGPAADIWSLGCVVLEMLTRQIPYPNVKWTKAL   1351
SEQ ID NO: 250  --------------------------------------------------------------------------------   1200
SEQ ID NO: 251  STRSGMHNLFNRAREAS---------------------------------------------------------------   1224
SEQ ID NO: 247  --------------------------------------------------------------------------------   1220
SEQ ID NO: 248  NIQVFMEKMQTLAET------------------------VQDSD--------------------D---------------   1012
SEQ ID NO: 249  --------------------------------------------------------------------------------   1021

1530       1540       1550       1560       1570       1580       1590       1600
                 ----+----|----+----|----+----|----+----|----+----|----+----|----+----|----+----|
SEQ ID NO: 246  YMIGKGEQPPIPNYLSEEAQDFICQCVRVDPETRPSATQLLEHPFVNRQSNLLSSLRVDDRLDQMPIGAIRKNVKKTVSH   1431
SEQ ID NO: 250  --------------------------------------------------------------------------------   1200
SEQ ID NO: 251  -----------K--------------------------LLVISRVSNEKVLPWMISSSGAIRCFDTLSISQKLSLSRYP-   1267
SEQ ID NO: 247  --------------------LSDETEGIADDEGEFSTRANASTPKVDEDEVDRRANNFIARFR------K---QI-----   1270
SEQ ID NO: 248  ------------------------------------------------------------------------L-------   1012
SEQ ID NO: 249  ----------------------------------------------------------------------TIRN------   1021

1610       1620       1630       1640       1650
                 ----+----|----+----|----+----|----+----|----+----|
SEQ ID NO: 246  CWFATQLLSPLFVNGLIGTMPLKFSRIEKLPLLFIILEQCHFWGTFLCLSLHAH   1485
SEQ ID NO: 250  -----------------------------------------------------   1200
SEQ ID NO: 251  CSFQLHLLMW------EKPIHPAERSIHRPKMPFFF                    1297
SEQ ID NO: 247  SGFAKKESS----IDERLWIRDLDECQLSKRGGRF                     1301
SEQ ID NO: 248  -----------------------------------------------------   1012
SEQ ID NO: 249  -----------------------------------------------------   1021
```

Figure 32a

```
Alignment Report of 'Rcglb vs PKs ClustalW.meg'  -  ClustalW (Slow/Accurate, Gonnet) : Thursday, June 07, 2007  11:00 AM 10        20        30        40        50        60        70        80
                   +---------+---------+---------+---------+---------+---------+---------+---------+
SEQ ID NO: 256  LTFLVSNKLLGVEQSFALWEERNELLGVHEHGDTHHISGIDEYNEVEDGVVAVEGEPKELRIGEALEGLTETSCLSMTTL  1104
SEQ ID NO: 252  ----------------------------------------DAGEEEDDAAAVLT--LEELRLGETSEE-----------  280
SEQ ID NO: 253  -------------------------------------------EEEEFADEGVAGVDGELKELRIGETFEG--------  343
SEQ ID NO: 254  -------------------------------------------------EEEGKEEEAEAEEMG--ARFIQLGDTADE--  301

90       100       110       120       130       140       150       160
                   +---------+---------+---------+---------+---------+---------+---------+---------+
SEQ ID NO: 256  EGFTGTSSLSMASDDDTSNTTMEEMFIS--PDRQLKRKIKSWMRGAFLGSSGSLGMVYEAISQEGVFFAVKEVSLLDQGSKA  1183
SEQ ID NO: 252  --FTGTSSLSTTNDDETSSTTTESMFYISPNGRFRRKIRSWNRGMLLGSSGSFGTVFEGISDEGVFFAVKEVCLCDQGSNA-  358
SEQ ID NO: 253  ---FTGTSSLSTTNDDDASSTTTEAMFIISPNGKFKRKIKSWMRGALLGSSGSFGMVYEGISDEGAFFAVKEVSLLDQGSNA  421
SEQ ID NO: 254  -----TCSFT-TNEGDSSSTVSNTSPIY-PDG--GAIITSWQKGQLLGRGSFGSVYEGISGDGDFFAVKEVSLLDQGSQA-  372

170       180       190       200       210       220       230       240
                   +---------+---------+---------+---------+---------+---------+---------+---------+
SEQ ID NO: 256  QQSILALEKKIELLSQLQHENIVHYYGTEKGESKLYIFVELVTQGSLSSLYKKYKLQESQVCWYTSQILNGLVYLHKQNV  1263
SEQ ID NO: 252  QQCIFQLEQEIALLSQFEHENIVQYYGTDBKEDSKLYIFLELVTQGSLASLYQKYRLRDTHVSAYTRQILNGLTYLHERNI  438
SEQ ID NO: 253  QQSILALEQEIALLSQFEHENIVQYYGTDKEESKLYIFIELVTQGSLSSLYQKYKLRDSQVSAYTRQILNGLVYLHERNV  501
SEQ ID NO: 254  QECIQQLEGEIKLLSQLQHQNIVRYRGTAKDGSNLYIFLELVTQGSLLKLYQRYQLRDSVVSLYTRQILDGLKYLHDKGF  452

250       260       270       280       290       300       310       320
                   +---------+---------+---------+---------+---------+---------+---------+---------+
SEQ ID NO: 256  VHGDIRCANILVHANESPKLADFGLAKEMSNILTLRSCERNVYWMAPEFINPKKT---FGPAADIWSLGCVVLEMLTRQIP  1341
SEQ ID NO: 252  VHRDIKCANILVHANGSVKLADFGLAKEITKFNVLKSCKGTVYWMAPEVVNPKTT---YGPEADIWSLGCTVLEMLTRQLP  516
SEQ ID NO: 253  VHRDIKCANILVHANGSVKLADFGLAKEMSKINMLRSCKGSVYWMAPEVVNPKKT---YGPQADIWSLGCTVLEMLTRNIP  579
SEQ ID NO: 254  IHRDIKCANILVDANGAVKLADFGLAK--VSKFNDIKSCCKGTPFWMAPEVINRKDSDGYGSPADIWSLGCTVLEMCTGQIP  531
```

Figure 32b

```
                 330        340        350        360        370        380        390        400
                  +---------+---------+---------+---------+---------+---------+---------+---------+
SEQ ID NO: 256 YPNVKWTKALYMIGKGEQPPIPNYLSEEAQDFICQCVRVDPETRPSATQLLEHPFVNRQSNLLSSLRVDDRLDQMPIGAI  1421
SEQ ID NO: 252 YPGLEWTQALYRIGKGEPPAIPNCLSRDARDFISQCVKPNPQDRPSAAKLLEHPFVNRSMRTSS-RSNSSVRGI        595
SEQ ID NO: 253 YPNVEWTNAFFMIGKGERPQIPSYLSKDAQFISQCVQVDPEQRPSASQLMSHPFVNR----P--LRAS--FESASPPAI  651
SEQ ID NO: 254 YSDLEPVQALFRIGRGTLPEVPDTLSLDARLFILKCLKVNPEERPTAAELLNHPFVRRP---LPSVGSGG--SGSASPLL  606
                  +---------+---------+---------+---------+---------+---------+---------+---------+

SEQ ID NO: 256 RKNVKKT  1428
SEQ ID NO: 252 NG       597
SEQ ID NO: 253 SSY      654
SEQ ID NO: 254 RR
```

METHODS FOR MAKING PLANTS RESISTANT TO FUNGAL PATHOGENS

CROSS REFERENCE TO RELATED APPLICATIONS

This application is continuation of U.S. application Ser. No. 15/492,199 filed on Apr. 20, 2017, which a continuation of U.S. application Ser. No. 14/159,220 filed on Jan. 20, 2014 now granted as U.S. Pat. No. 9,657,356, which is a divisional of Ser. No. 13/272,057 filed on Oct. 12, 2011 now granted as U.S. Pat. No. 8,633,349, which is a continuation of Ser. No. 12/139,039 filed Jun. 13, 2008 now granted as U.S. Pat. No. 8,053,631, and also claims priority to and benefit of U.S. Provisional Application No. 60/944,209, filed on Jun. 15, 2007, which is herein incorporated by reference in its entirety.

FIELD OF THE INVENTION

This invention relates to compositions and methods useful in creating or enhancing pathogen-resistance in plants. Additionally, the invention relates to plants that have been genetically transformed with the compositions of the invention.

BACKGROUND OF THE INVENTION

*Colletotrichum graminicola* (Ces.) (Cg), more commonly known as anthracnose, is the causative agent of anthracnose leaf blight, anthracnose stalk rot (ASR) and top dieback that affects *Zea mays* (L.), also known as maize or corn. It is the only known common stalk rot that also causes a leaf blight (Bergstrom, et al., (1999), *Plant Disease*, 83:596-608, White, D. G. (1998), *Compendium of Corn Diseases*, pp. 1-78). It has been known to occur in the United States since 1855 and has been reported in the Americas, Europe, Africa, Asia, and Australia (McGee, D. C. (1988), *Maize Diseases: A Reference Source for Seed Technologists*, APS Press, St. Paul, Minn.; White, (1998) supra; White, et al., (1979) *Proc. Annu. Corn Sorghum Res Conf* ($34^{th}$) 1-15). In the United States alone, over 37.5 million acres are infested annually with average yield losses of 6.6% nationwide (See FIG. 1). The yield losses are due both to low kernel weight in infected plants and "lodging," that is, the falling over of the plants due to weakness in the stalks caused by the infection (Dodd, J., (1980), *Plant Disease*, 64:533-537). Lodged plants are more difficult to harvest and are susceptible to other diseases. After infection, typically the upper portion of the stalk dies first while the lower stalk is still green. Externally, infection can be recognized by blotchy black patches on the outer rind of the stalk, while internally the pith tissue is discolored or black in appearance. Inoculation occurs in a number of ways. Roots may grow through stalk debris and become infected. This will become an increasing problem as "no till" methods of agriculture are more widely adopted due to their environmental benefits. The fungus may also infect the stalks through insect damage and other wounds (White (1998) supra). Stalk infection may be preceded by leaf infection causing leaf blight and providing inoculum for stalk infection. There is controversy in the technical literature as to the number of different varieties or races of Cg present in nature. The pathogen is transmitted by wind or contaminated seed lots. Spores remain viable for up to 2 years (McGee (1988) supra; Nicholson, et al., (1980), *Phytopathology*, 70:255-261; Warren, H. L. (1977), *Phytopathology*, 67:160-162; Warren, et al., (1975), *Phytopathology*, 65:620-623).

Farmers may combat infection by corn fungal diseases such as anthracnose through the use of fungicides, but these have environmental side effects, and require monitoring of fields and diagnostic techniques to determine which fungus is causing the infection so that the correct fungicide can be used. Particularly with large field crops such as corn, this is difficult. The use of corn lines that carry genetic or transgenic sources of resistance is more practical if the genes responsible for resistance can be incorporated into elite, high yielding germplasm without reducing yield. Genetic sources of resistance to Cg have been described. There have been several maize lines identified that carry some level of resistance to Cg (White, et al. (1979) supra). These included A556, MP305, H21, SP288, CI88A, and FR16. A reciprocal translocation testcross analysis using A556 indicated that genes controlling resistance to ASR lie on the long arms of chromosomes 1, 4, and 8 as well as both arms of chromosome 6 (Carson, M. L. (1981), *Sources of inheritance of resistance to anthracnose stalk rot of corn*. Ph.D. Thesis, University of Illinois, Urbana-Champaign). Introgression of resistance derived from such lines is complex. Another inbred, LB31, was reported to carry a single dominant gene controlling resistance to ASR but appears to be unstable, especially in the presence of European corn borer infestation (Badu-Apraku et al., (1987) *Phytopathology* 77: 957-959). The line MP305 was found to carry two dominant genes for resistance, one with a major effect and one with a minor effect (Carson (1981) supra). MP305 has been made available by the University of Mississippi through the National Plant Germplasm System (GRIN ID: NSL 250298) operated by the United States Department of Agriculture. See Compilation of North American Maize Breeding Germplasm, J. T. Gerdes et al., Crop Science Society of America, 1993. Seed of MP305 can be obtained through W. Paul Williams, Supervisory Research Geneticist USDA-ARS, Corn Host Plant Resistance Research Unit, Box 9555, 340 Dorman Hall, Miss. State, Miss. 39762.

It has been reported that there are two genetically separable (meaning they behaved as separate genetic loci) genes linked on the long arm of chromosome 4 that confer resistance to Cg (Toman, et al., (1993), *Phytopathology*, 83:981-986; Cowen, N et al. (1991) Maize Genetics Conference Abstracts 33). A significant resistance quantitative trait locus (QTL) on chromosome 4 has also been reported (Jung, et al., (1994), *Theoretical and Applied Genetics*, 89:413-418). Jung et al. (supra) reported that UMC15 could be used to select for the QTL on chromosome 4 in MP305, and suggested that the QTL is on a 12 cM region of chromosome 4 between UMC15 and UMC66. In fact, as discussed in more detail below, the region between UMC15 and UMC66 as reported on the IBM2 neighbors 4 genetic map is approximately 129 cM, and selection for the QTL in the manner suggested by Jung et al. (1994, supra) would at best select a large chromosomal interval with considerable linkage drag and negative phenotypic effect, and at worst, a double recombination could occur between the two markers resulting in a false positive selection for the Rcg1 locus. The region carrying the genes responsible for the phenotype conferred by the QTL on chromosome 4 will be referred to herein as the Rcg1 locus or the MP305 resistance locus; it has elsewhere been referred to as the ASR locus.

Much work has been done on the mechanisms of disease resistance in plants in general. Some mechanisms of resistance are non-pathogen specific in nature, or so-called "non-host resistance." These may be based on cell wall structure or similar protective mechanisms. However, while plants lack an immune system with circulating antibodies and the other attributes of a mammalian immune system, they do have other mechanisms to specifically protect against pathogens. The most important and best studied of these are the plant disease resistance genes, or "R" genes. One of very many reviews of this resistance mechanism and the R genes can be found in Bekhadir et al., (2004), *Current Opinion in Plant Biology* 7:391-399. There are 5 recognized classes of R genes: intracellular proteins with a nucleotide-binding site (NBS) and a leucine-rich repeat (LRR); transmembrane proteins with an extracellular LRR domain (TM-LRR); transmembrane and extracellular LRR with a cytoplasmic kinase domain (TM-CK-LRR); membrane signal anchored protein with a coiled-coil cytoplasmic domain (MSAP-CC); and membrane associated kinases with an N-terminal myristylation site (MAK-N) (See, for example: Cohn, et al., (2001), *Immunology*, 13:55-62; Dangl, et al. (2001), *Nature*, 411:826-833).

Broglie et al. (U.S. patent application Ser. No. 11/397, 153) described a novel R gene related to the NBS-LRR type designated Rcg1 found within the Rcg1 locus previously described by Jung et al. (supra). They described markers of use in breeding with this locus, chromosomal intervals which can endow corn plants with resistance, and transgenic plants containing the Rcg1 gene. The present invention improves on the work of Broglie et al. by providing a second NBS-LRR gene, different from the Rcg1 gene and designated Rcg1b, that is required in combination with Rcg1 for resistance to Cg. The Rcg1b gene is physically (200-300 kb) and genetically (less than 1 centimorgan) tightly linked to Rcg1 and represents a second component of the Rcg1 locus. The present invention provides sequences for Rcg1b, chimeric constructs combining Rcg1 and Rcg1b, and methods and markers for breeding with the Rcg1 and Rcg1b genes together (the Rcg1 locus).

SUMMARY OF THE INVENTION

Embodiments of this invention are based on the fine mapping, cloning and characterization of the genes responsible for the resistance phenotype from the line MP305, the introgression of a truncated chromosomal interval with the MP305 resistance locus (Rcg1 locus) into other lines with little or no linkage drag, the demonstration of the use of those genes as transgenes and the use of molecular markers to move the genes into elite lines using breeding techniques.

Embodiments include an isolated polynucleotide comprising a nucleotide sequence encoding the Rcg1b polypeptide, which in conjunction with the Rcg1 polypeptide, confers resistance to *Colletotrichum*, wherein the Rcg1 polypeptide has an amino acid sequence of at least 50%, at least 75%, at least 80%, at least 85%, at least 90%, and at least 95% identity, when compared to SEQ ID NO:3 or the peptide encoded by the Rcg1 sequence deposited with the Agricultural Research Service (ARS) Culture Collection on Feb. 22, 2006 as Patent Deposit No. NRRL B-30895, and further wherein the Rcg1b polypeptide has an amino acid sequence of at least 50%, at least 75%, at least 80%, at least 85%, at least 90%, and at least 95% identity, when compared to SEQ ID NO:246 or the peptide encoded by the Rcg1 b sequence deposited with the Agricultural Research Service (ARS) Culture Collection on Jun. 26, 2007 as Patent Deposit No. NRRL B-50050 based on the Needleman-Wunsch alignment algorithm, or a complement of the nucleotide sequence, wherein the complement and the nucleotide sequence consist of the same number of nucleotides and are 100% complementary. Embodiments also include an isolated polynucleotide comprising a nucleotide sequence encoding a polypeptide capable, in conjunction with the Rcg1 polypeptide, of conferring resistance to *Colletotrichum*, wherein the polypeptide has an amino acid sequence of at least 50%, at least 75%, at least 80%, at least 85%, at least 90%, and at least 95% identity, when compared to SEQ ID NO: 246.

Additional embodiments of the present invention include a vector comprising the polynucleotide that encodes a polypeptide of an embodiment of the present invention, such as SEQ ID NO: 3, SEQ ID NO: 246, or the polynucleotide sequence of the plasmid deposited as Patent Deposit No. NRRL B-30895, or the polynucleotide sequence of the plasmid deposited as Patent Deposit No. NRRL-B-50050, and a recombinant DNA construct comprising the polynucleotide of an embodiment of the present invention operably linked to at least one regulatory sequence. Additional embodiments of the present invention include vectors comprising polynucleotides that encode both SEQ ID NO: 3 and SEQ ID NO: 246. A plant cell, as well as a plant, each comprising a recombinant DNA construct of an embodiment of the present invention, and a seed comprising a recombinant DNA construct of the embodiments are also embodied by the present invention.

The methods embodied by the present invention include 1) a method for transforming a host cell, including a plant cell, comprising transforming the host cell with the polynucleotide of an embodiment of the invention, 2) a method for producing a plant comprising transforming a plant cell with the recombinant DNA construct of an embodiment of the present invention and regenerating a plant from the transformed plant cell, and 3) methods of conferring or enhancing resistance to *Colletotrichum* and/or stalk rot, comprising transforming a plant with the recombinant DNA construct of an embodiment of the present invention, thereby conferring and/or enhancing resistance to *Colletotrichum* or stalk rot.

Additional embodiments include methods of determining the presence or absence of the polynucleotide of an embodiment of the present invention, or the Rcg1 locus, in a corn plant, comprising at least one of (a) isolating nucleic acid molecules from the corn plant and determining if an Rcg1 gene is present or absent, and determining if an Rcg1b gene is present or absent, by amplifying sequences homologous to the polynucleotide, (b) isolating nucleic acid molecules from the corn plant and performing a Southern hybridization, (c) isolating proteins from the corn plant and performing a western blot using antibodies to the Rcg1 protein and/or the Rcg1b protein, (d) isolating proteins from the corn plant and performing an ELISA assay using antibodies to the Rcg1 protein and/or the Rcg1b protein, (e) demonstrating the presence of m RNA sequences derived from the Rcg1 and/or Rcg1b m RNA transcript and unique to Rcg1 and/or Rcg1b, or (f) demonstrating the presence of newly conferred or enhanced resistance to *Colletotrichum* infection through a phenotypic assay, thereby determining the presence of the polynucleotides or the Rcg1 locus in the corn plant.

Methods of altering the level of expression of a protein capable of conferring resistance to *Colletotrichum* or stalk rot in a plant or plant cell comprising (a) transforming a plant cell with the recombinant DNA construct of an embodiment of the present invention and (b) growing the transformed plant cell under conditions that are suitable for expression of the recombinant DNA construct wherein expression of the recombinant DNA construct results in production of altered levels of a protein capable of conferring resistance to *Colletotrichum* or stalk rot in the transformed host are also embodied by the present invention.

An additional method embodied by the present invention is a method of conferring or enhancing resistance to *Colletotrichum* and/or stalk rot in a corn plant, comprising (a) crossing a first corn plant lacking the Rcg1 locus with a second corn plant containing the Rcg1 locus to produce a segregating population, (b) screening the segregating population for a member containing the Rcg1 locus with a first nucleic acid, not including UMC15a or UMC66, capable of hybridizing with a second nucleic acid linked to or located within the Rcg1 locus, and (c) selecting the member for further crossing and selection.

Methods of enhancing resistance to *Colletotrichum* and/or stalk rot, or introgressing *Colletotrichum* and/or stalk rot resistance into a corn plant, comprising performing marker assisted selection of the corn plant with a nucleic acid marker, wherein the nucleic acid marker specifically hybridizes with a nucleic acid molecule having a first nucleic acid sequence that is linked to a second nucleic acid sequence that is located on the Rcg1 locus of MP305 and selecting the corn plant based on the marker assisted selection are also embodiments of the present invention. Specific FLP, MZA and Rcg1-specific SNP markers disclosed herein are further aspects of the invention.

Another embodiment of the invention is a process of identifying a corn plant that displays newly conferred or enhanced resistance to *Colletotrichum* infection by detecting alleles of at least one marker on or within the Rcg1b gene, and optionally by detecting a second marker on or within the Rcg1 gene.

Further embodiments include processes for identifying corn plants that display newly conferred or enhanced resistance to *Colletotrichum* by detecting alleles of at least 2 markers in the corn plant, wherein at least one of the markers is on or within the chromosomal interval below UMC2041 and above the Rcg1b gene, and at least one of the markers is on or within the interval below the Rcg1 gene and above UMC2200. Similar embodiments encompassed by this process include at least one of the markers being on or within the chromosomal interval below UMC1086 and above the Rcg1b gene, on or within the chromosomal interval below UMC2285 and above the Rcg1b gene, and at least one of the markers is on or within the interval below the Rcg1 gene and above UMC2200, on or within the interval below the Rcg1 gene and above UMC2187, or on or within the interval below the Rcg1 gene and above UMC15a.

Further embodiments include processes for identifying corn plants that display newly conferred or enhanced resistance to *Colletotrichum* by detecting alleles of at least 2 markers in the corn plant, wherein at least one of the markers on or within the chromosomal interval below UMC2041 and above the Rcg1b gene is selected from the markers listed in Table 16, and at least one of the markers on or within the interval below the Rcg1 gene and above UMC2200 is also selected from the markers listed in Table 16. Embodiments include processes for identifying corn plants that display newly conferred or enhanced resistance to *Colletotrichum* by selecting for at least four markers or at least six, wherein at least two or three of the markers are on or within the chromosomal interval below UMC2041 and above the Rcg1b gene, and at least two or three of the markers are on or within the interval below the Rcg1 gene and above UMC2200. Additional embodiments include this same process when the two or three markers on or within the chromosomal interval below UMC2041 and above the Rcg1b gene, as well as the two or three markers on or within the interval below the Rcg1 gene and above UMC2200, are selected from those listed in Table 16. Another embodiment of this process includes detecting allele 7 at MZA1112, detecting allele 2 at MZA2591, or detecting allele 8 at MZA3434. Corn plants and seeds produced by the embodied processes are also embodiments of the invention, including those corn plants which do not comprise the same alleles as MP305 at or above UMC2041, or at or below UMC2200 at the loci shown in Table 16.

Other embodiments include processes for identifying corn plants that display newly conferred or enhanced resistance to *Colletotrichum* by detecting alleles of at least 2 markers in the corn plant, wherein at least one of the markers is on or within the chromosomal interval below UMC2041 and above the Rcg1b gene, and at least one of the markers is on or within the interval below the Rcg1 gene and above UMC2200, and where the process detects the presence or absence of at least one marker located within the Rcg1 gene or the Rcg1b gene. A further such embodiment includes a modification of this process in which four markers are selected for, in which two of the markers are within the chromosomal interval below UMC2285 and above the Rcg1b gene, and at least two of the markers are within the interval below the Rcg1 gene and above UMC15a. A further embodiment of this process includes the Rcg1 gene and the Rcg1b gene having been introgressed from a donor corn plant, including MP305 or DE811ASR(BC5), into a recipient corn plant to produce an introgressed corn plant. This process also includes the instance when the introgressed corn plant is selected for a recombination event below the Rcg1 gene and above UMC15a, so that the introgressed corn plant retains a first MP305 derived chromosomal interval below the Rcg1 gene and above UMC15a, and does not retain a second MP305 derived chromosomal interval at and below UMC15a. Corn plants and seeds produced by these processes are also embodiments of the invention. Introgressed corn plants embodied by the invention include those that are Rcg1 locus conversions of PH705, PH5W4, PH51K or PH87P, or progeny thereof.

A further embodiment of the invention is a process of identifying a corn plant that displays enhanced resistance to *Colletotrichum* infection, by detecting in the corn plant the presence or absence of at least one marker at the Rcg1 locus, and selecting the corn plant in which the at least one marker is present. Embodiments include when at least one marker is on or within SEQ ID NOs: 137, 255, 256, 257, 258, or 266 and also when at least one marker is on or within the Rcg1 or Rcg1b coding sequence, or located on or within the polynucleotide set forth in SEQ ID NO: 1 or SEQ ID NO: 245.

Introgressed corn plants embodied by the invention include those that are Rcg1 locus conversions of PH705, PH5W4, PH51K or PH87P, or progeny thereof. Such embodiments include corn seed comprising a first MP305 derived chromosomal interval defined by BNLG2162 and UMC1051, and not comprising a second MP305 derived chromosomal interval above UMC2041 or below UMC1051, and when the corn seed comprises at least one of the Rcg1 and the Rcg1b genes and, when grown, produces a corn plant that exhibits resistance to *Colletotrichum* infection. Seed of the embodiments also includes corn seed comprising a first MP305 derived chromosomal interval between, but not including, UMC2285 and UMC15a, and not comprising a second MP305 derived chromosomal interval at or above UMC2285 or at or below UMC15a, and furthermore such corn seed which comprises the Rcg1 and the Rcg1b genes and, when grown, produces a corn plant that exhibits resistance to *Colletotrichum* infection. Corn plants and plant cells produced from this seed are also included in the embodiments of the invention.

Progeny seed that is an Rcg1 locus conversion of PH705, PH5W4, PH51K or PH87P, or a progeny thereof is also embodied in the invention, as are progeny seed that comprise at least two or more of allele 7 at MZA11123, allele 2 at MZA2591, or allele 8 at MZA3434. Further embodiments include progeny seed which comprise a cytosine nucleotide at MZA2591.32, a thymine nucleotide at MZA2591.35, and a cytosine nucleotide at MZA3434.17.

Embodiments also include genetic markers on or within SEQ ID NOs: 140 through 146 for MZA3434, MZA2591, MZA11123, MZA15842, MZA1851, MZA8761 and MZA11455, respectively. Other embodiments include genetic markers located on or in the Rcg1 locus or the Rcg1 gene or the Rcg1b gene, including those located on SEQ ID NO: 137 or on any of SEQ ID NOs: 255, 256, 257, 258 and 266. Embodied markers also include those located on SEQ ID NO: 1 or SEQ ID NO: 245.

BRIEF DESCRIPTION OF THE DRAWINGS

FIGS. 2a-2c show an alignment of a polypeptide sequence of the embodiments (SEQ ID NO: 3) comparing it to other known NBS-LRR polypeptides.

FIG. 3 is a graph produced by Windows QTL Cartographer software showing a statistical analysis of the chance (Y axis) that the locus responsible for the Cg resistance phenotype is located at a particular position along the chromosome (X axis) as defined by FLP markers.

FIG. 4 is an electrophoresis gel blot of aliquots of RT-PCR reactions which reveals the presence of a 260 bp band present in the samples derived from both infected and uninfected resistant plants but absent from susceptible samples. RT-PCR fragments were obtained from 12.5 ng total RNA from DE811 and DE811ASR stalk tissue. cDNA obtained by reverse transcription was amplified using Rcg1 specific primers and 18S rRNA primers as an internal standard.

FIG. 9(a) shows the alignment of the non-colinear region from DE811ASR (BC5) relative to B73 and Mo17. The BAC sizes in FIG. 9(a) are estimates. FIG. 9(b) shows a portion of the non-colinear region as set forth in SEQ ID NO: 137 on which Rcg1 resides, including the repetitive regions therein, as well as the Rcg1 exons 1 and 2.

FIG. 10 show distributions of average leaf lesion size in different individual plants at 15 days after inoculation with Cg in the a) DE811ASR(BC5) and b) DE811 lines, respectively.

Figure 11:
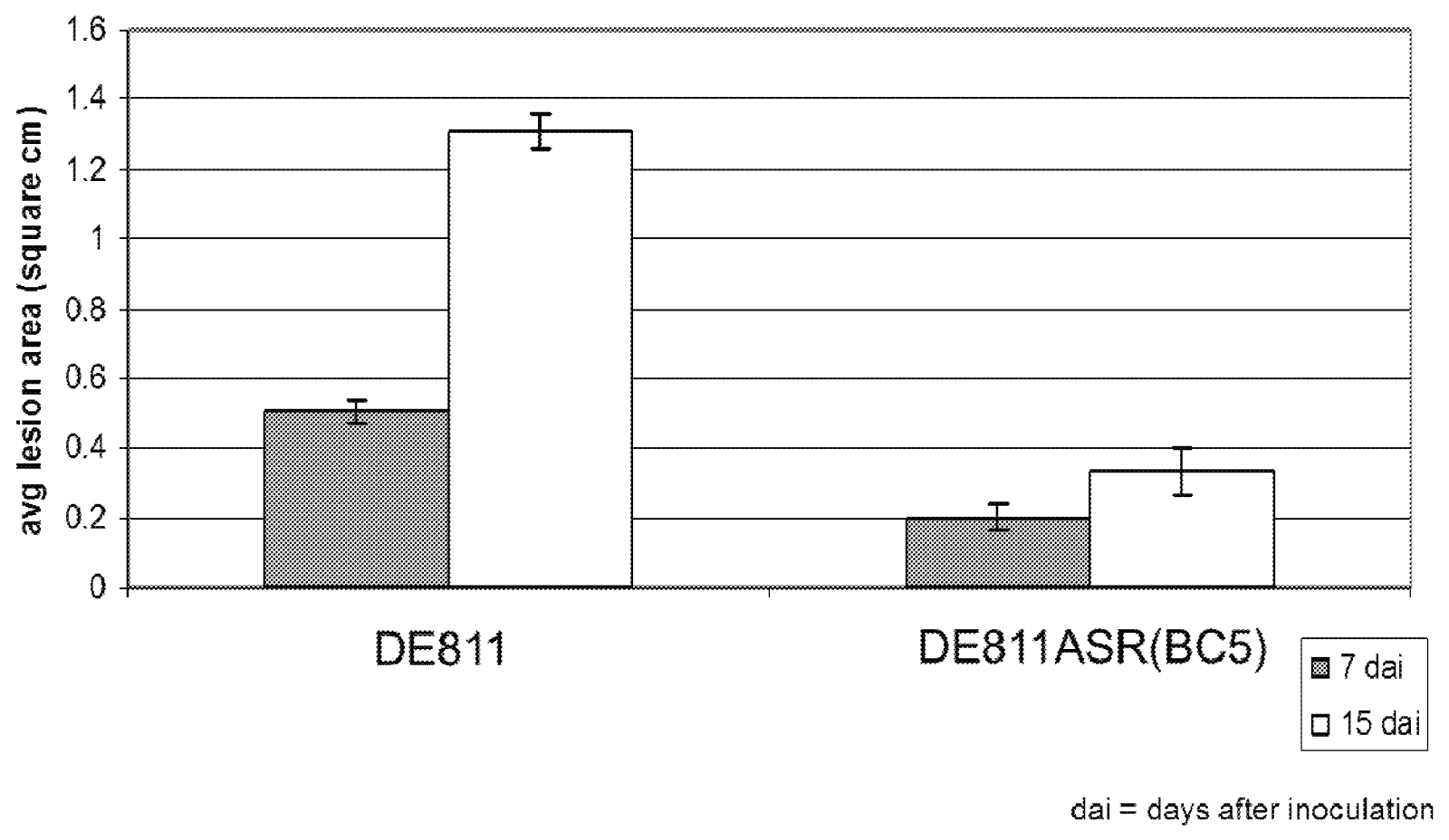

FIG. 11 shows a comparison of average leaf lesion size on plants of DE811 and DE811ASR(BC5) infected with Cg at 7 and 15 days after inoculation.

FIG. 21 shows a contig on the B73 physical map that is homologous to the region into which the Rcg1 non-colinear region containing DE811ASR (BC5) is inserted, which demonstrates that many B73 derived bacterial artificial chromosomes (BACs) are available in the region of interest from which sequence information can be obtained.

FIGS. 31a through 31g provide an alignment of the Rcg1b peptide (SEQ ID NO: 246) of the embodiments with several NBS-LRR proteins from barley and rice (SEQ ID NOs: 247-251), showing regions of homology.

FIGS. 32a and 32b provide an alignment of amino acids 1036-1399 of SEQ ID NO: 246, which are separately set forth as SEQ ID NO: 256, with several putative protein kinases (SEQ ID NOs: 252-254) identified in a BLAST® P homology search.

DETAILED DESCRIPTION OF THE INVENTION

Figure 1:
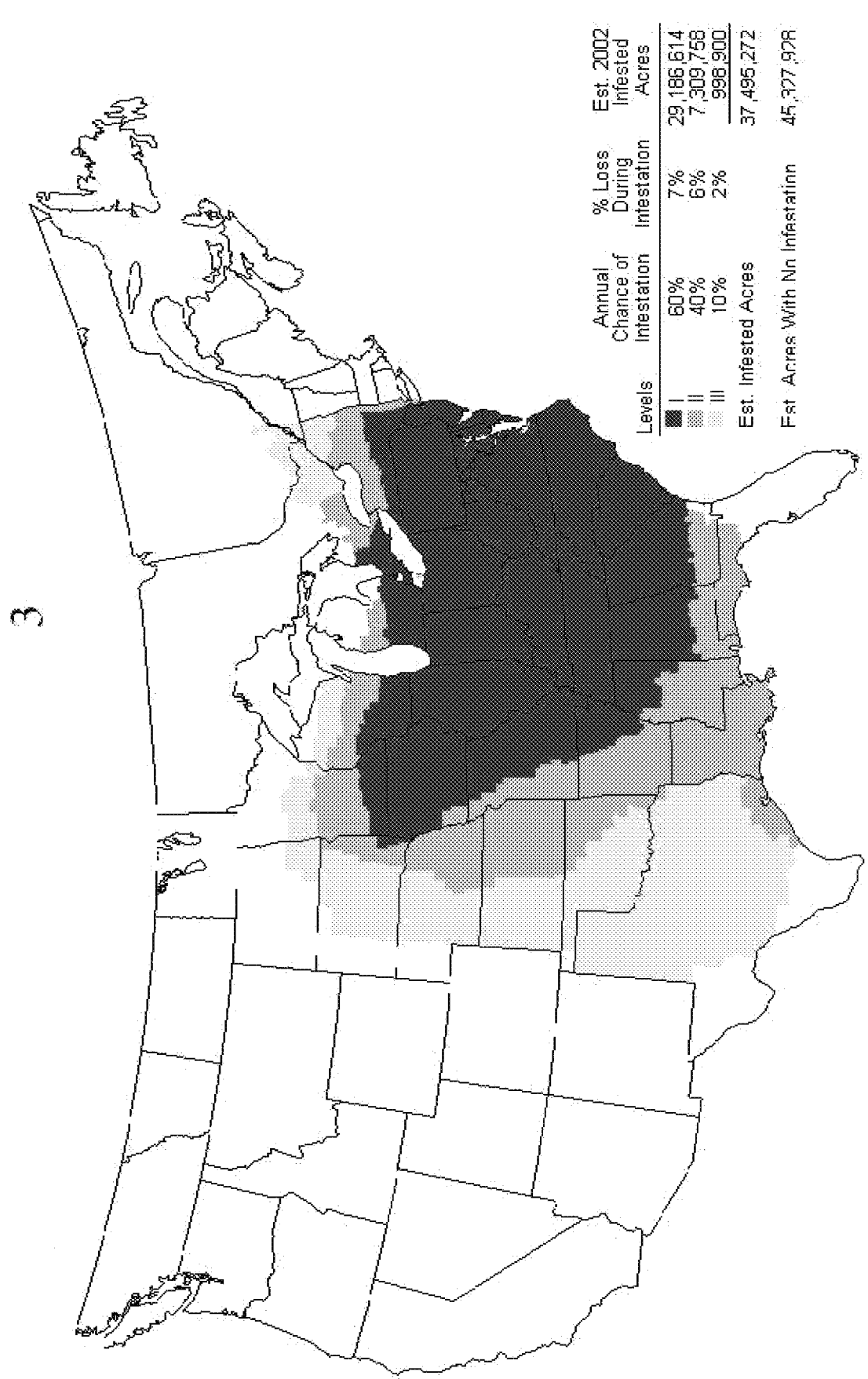
FIG. 1 is a map of the United States showing the severity of anthracnose stalk rot infestation by county for 2002.

Embodiments of the present invention provide compositions and methods (or processes) directed to inducing pathogen resistance, particularly fungal resistance, in plants. The compositions are novel nucleotide and amino acid sequences that confer or enhance resistance to plant fungal pathogens. Specifically, certain embodiments provide polypeptides having the amino acid sequences set forth in SEQ ID NO: 3 and SEQ ID NO: 246, and variants and fragments thereof. Isolated nucleic acid molecules, and variants and fragments thereof, comprising nucleotide sequences that encode the amino acid sequences shown in SEQ ID NO: 3 and SEQ ID NO: 246 are further provided.

Nucleotide sequences that encode the polypeptide of SEQ ID NO: 3 are set forth in SEQ ID NOs: 1 and 4. Nucleotide sequences that encode the polypeptide of SEQ ID NO: 246 are set forth in SEQ ID NOs: 255-258, as well as 246 and 266. The genomic sequence of the Rcg1b gene and its flanking regions is provided in SEQ ID NOs: 255-258, or in SEQ ID NO: 266, which are discussed in more detail in Example 9. The cDNA sequence that encodes the polypeptide of SEQ ID NO: 246 is set forth in SEQ ID NO: 245. Plants, plant cells, seeds, and microorganisms comprising a nucleotide sequence that encodes a polypeptide of the embodiments are also disclosed herein.

A deposit of the Rcg1 nucleic acid molecule was made on Feb. 22, 2006 with the Agricultural Research Service (ARS) Culture Collection, housed in the Microbial Genomics and Bioprocessing Research Unit of the National Center for Agricultural Utilization Research (NCAUR), under the Budapest Treaty provisions. The deposit was given the following accession number: NRRL B-30895. The address of NCAUR is 1815 N. University Street, Peoria, Ill., 61604. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112. The deposit will irrevocably and without restriction or condition be available to the public upon issuance of a patent. However, it should be understood that the availability of a deposit does not constitute a license to practice the subject invention in derogation of patent rights granted by government action.

A sample of 2500 seeds of DE811ASR (BC5) were deposited in the American Type Culture Collection (ATCC), 10801 University Blvd., Manassas, Va. 20110-2209, USA on Mar. 13, 2006 and assigned Deposit No. PTO-7434. Access to this deposit will be available during the pendency of the application to the Commissioner of Patents and Trademarks, persons determined by the Commissioner to be entitled thereto upon request, and corresponding officials in foreign patent offices in which this patent application is filed. This deposit will be maintained under the terms of the Budapest Treaty on the International Recognition of the Deposit of Microorganisms for the Purposes of Patent Procedure. The deposit will irrevocably and without restriction or condition be available to the public upon issuance of a patent. However, it should be understood that the availability of the deposit does not constitute a license to practice the subject invention or methods in derogation of patent rights.

A deposit of the Rcg1b nucleic acid molecule was made on Jun. 26, 2007 with the Agricultural Research Service (ARS) Culture Collection, housed in the Microbial Genomics and Bioprocessing Research Unit of the National Center for Agricultural Utilization Research (NCAUR), under the Budapest Treaty provisions. The deposit was given the following accession number: NRRL B-50050. The address of NCAUR is 1815 N. University Street, Peoria, Ill., 61604. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112. The deposit will irrevocably and without restriction or condition be available to the public upon issuance of a patent. However, it should be understood that the availability of a deposit does not constitute a license to practice the subject invention in derogation of patent rights granted by government action.

The two full length polypeptides of the embodiments (SEQ ID NOs: 3 and 246) share varying degrees of homology with known polypeptides of the NBS-LRR family. In particular, Rcg1 (SEQ ID NO: 3) shares homology with NBS-LRR proteins isolated from *Oryza sativa* (Accession Nos. NP_910480 (SEQ ID NO: 14), NP_910482 (SEQ ID NO: 16), NP_921091 (SEQ ID NO: 17) and NP_910483 (SEQ ID NO: 15)) and *Hordeum vulgare* (Accession No. AAG37354 (SEQ ID NO: 18); Zhou et al., (2001) Plant Cell 13:337-350). FIG. 2 provides an alignment of the amino acid sequence set forth in SEQ ID NO: 3 with the *O. sativa* and *H. vulgare* proteins (SEQ ID NOs: 14-18). Amino acid alignments using the GAP program to compare SEQ ID NO: 3 to the various rice and barley sequences identified above indicated that SEQ ID NO:3 shares approximately 42.3% sequence similarity with the *O. sativa* protein NP_910480 (SEQ ID NO: 14), 41.7% sequence similarity with the *O. sativa* protein NP_910482 (SEQ ID NO: 16), 56.9% similarity with the *O. sativa* protein NP_921091 (SEQ ID NO: 17) and 42.1% sequence similarity with the *O. sativa* protein NP_910483 (SEQ ID NO: 15). Furthermore, SEQ ID NO: 3 shares approximately 42.8% sequence similarity with the *H. vulgare* protein AAG37354 (SEQ ID NO: 18).

Similar analysis was conducted for the Rcg1b peptide (SEQ ID NO: 246), which was found to share homology with NBS-LRR proteins isolated from *Oryza sativa* (Accession Nos. ABA95308 (SEQ ID NO: 250), ABG66042 (SEQ ID NO: 251), ABA92208 (SEQ ID NO: 247) and ABG66044 (SEQ ID NO: 248)) and *Hordeum vulgare* (Accession No. AAM22820 (SEQ ID NO: 249)). FIG. 31*a* through 31*g* provides an alignment of the amino acid sequence set forth in SEQ ID NO: 246 with the *O. sativa* and *H. vulgare* proteins with the accession numbers provided above (SEQ ID NOs: 247-251). Amino acid alignments using the ClustalW pair-wise alignments (Gap opening penalty=10, Gap extension penalty=0.1) indicate that SEQ ID NO: 246 shares approximately 37.1% sequence identity with the *O. sativa* protein ABA92208 (SEQ ID NO: 247), 28.2% sequence identity with the *O. sativa* protein ABG66044 (SEQ ID NO: 248), 26.6% identity with the *O. sativa* protein ABA95308 (SEQ ID NO: 250) and 31.1% sequence similarity with the *O. sativa* protein ABG66042 (SEQ ID NO: 251). Furthermore, SEQ ID NO: 3 shares approximately 25.6% sequence similarity with the *H. vulgare* protein AAM22820 (SEQ ID NO: 249).

The NBS-LRR group of R-genes is the largest class of R-genes discovered to date. In *Arabidopsis thaliana*, over 150 are predicted to be present in the genome (Meyers, et al., (2003), *Plant Cell,* 15:809-834; Monosi, et al., (2004), *Theoretical and Applied Genetics,* 109:1434-1447), while in rice, approximately 500 NBS-LRR genes have been predicted (Monosi, (2004) supra). The NBS-LRR class of R genes is comprised of two subclasses. Class 1 NBS-LRR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) *Genome Research,* 12:1871-1884; Monosi, (2004) supra; Pan, et al., (2000), *Journal of Molecular Evolution,* 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), *Current Biology: CB,* 8:R226-R227). The LRR region appears to be the region that interacts with the pathogen AVR products (Michelmore, et al., (1998), *Genome Res.,* 8:1113-1130; Meyers, (2003) supra). This LRR region in comparison with the NBS domain is under a much greater selection pressure to diversify (Michelmore, (1998) supra; Meyers, (2003) supra; Palomino, et al., (2002), *Genome Research,* 12:1305-1315). LRR domains are found in other contexts as well; these 20-29-residue motifs are present in tandem arrays in a number of proteins with diverse functions, such as hormone—receptor interactions, enzyme inhibition, cell adhesion and cellular trafficking. A number of recent studies revealed the involvement of LRR proteins in early mammalian development, neural development, cell polarization, regulation of gene expression and apoptosis signaling.

The gene of the embodiments is clearly related to the NBS-LRR of the class 2 family, but does not completely fit the classical mold. The amino end has homology to so-called nucleotide binding sites (NBS). There is a leucine rich region as well, located, as expected, downstream of the NBS. However, unlike previously studied NBS-LRR proteins, the leucine rich region lacks the systematic repetitive nature found in more classical LRR domains, much less consistently following the typical Lxx repeat pattern and in particular having no instances of the consensus sequences described by Wang et al. ((1999) *Plant J.* 19:55-64; see especially, FIG. 5) or Bryan et al. ((2000), Plant Cell 12:2033-2045; see especially, FIG. 3). Rcg1b, in addition to the NBS and LRR domains, contains a protein kinase domain.

As the LRR region is the receptor portion of an NBS-LRR, when a new LRR such as those of this disclosure are found, the range of its activity, that is, the range of pathogens to which it will respond, is not immediately obvious from the sequence. The genes of the embodiments were isolated on the basis of the Cg resistance phenotype, and therefore the novel LRR responds to Cg. However, it is not excluded that they respond to other pathogens not tested in the work done heretofore.

The nucleic acids and polypeptides of the embodiments find use in methods for conferring or enhancing fungal resistance to a plant. Accordingly, the compositions and methods disclosed herein are useful in protecting plants from fungal pathogens. "Pathogen resistance," "fungal resistance," and "disease resistance" are intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from pathogen attack.

Hence, the methods of the embodiments can be utilized to protect plants from disease, particularly those diseases that are caused by plant fungal pathogens. As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the invention also will enhance or improve fungal plant pathogen resistance, such that the resistance of the plant to a fungal pathogen or pathogens will increase. The term "enhance" refers to improve, increase, amplify, multiply, elevate, raise, and the like. Herein, plants of the invention are described as being resistant to infection by Cg or having 'enhanced resistance' to infection by Cg as a result of the Rcg1 locus of the invention. Accordingly, they typically exhibit increased resistance to the disease when compared to equivalent plants that are susceptible to infection by Cg because they lack the Rcg1 locus. For example, using the scoring system described in Example 11 (also see FIG. 20), they typically exhibit a one point, two point or three point or more decrease in the infection score, or even a reduction of the score to 1 or 0, when compared to equivalent plants that are susceptible to infection by Cg because they lack the Rcg1 locus.

In particular aspects, methods for conferring or enhancing fungal resistance in a plant comprise introducing into a plant at least one expression cassette, wherein the expression cassette comprises a nucleotide sequence encoding the antifungal polypeptides of the embodiments each operably linked to a promoter that drives expression in the plant. The plant expresses the two polypeptides, thereby conferring fungal resistance upon the plant, or improving the plant's inherent level of resistance. In particular embodiments, the gene confers resistance to the fungal pathogen, Cg. The skilled artisan could, if desired, create two separate transgenic plants each expressing one of the two polypeptides and then cross the two plants, selecting for plants that express both polypeptides.

Expression of an antifungal polypeptide of the embodiments may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The embodiments of the invention encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have the ability to confer fungal resistance upon a plant. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments (for example, 980 amino acids for the peptide encoded by SEQ ID NO:1). Fragments of a nucleotide sequence that are useful as hybridization probes or PCR primers generally need not encode a biologically active portion of a protein.

As used herein, "full-length sequence," in reference to a specified polynucleotide, means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an antipathogenic polypeptide can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein (for example, 4212 nucleotides for SEQ ID NO: 1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NOs: 3 or 246 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant fungal pathogen resistance as described herein. Such variants may result, for example, from genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res.

Found., Washington, D.C.), herein incorporated by reference. Conservative substitutions, such as exchanging one amino acid with another having similar properties, may be optimal.

Thus, the genes and polynucleotides of the embodiments include both naturally occurring sequences as well as mutant forms. Likewise, the proteins of the embodiments encompass both naturally occurring proteins as well as variations and modified forms thereof. Such variants will continue to possess the desired ability to confer or enhance plant fungal pathogen resistance. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the ability of the plant to resist fungal pathogenic attack.

Variant polynucleotides and proteins also encompass sequences and proteins derived from mutagenic or recombinogenic procedures, including and not limited to procedures such as DNA shuffling. One of skill in the art could envision modifications that would alter the range of pathogens to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant fungal pathogen resistance. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances fungal plant pathogen resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.*

215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the website at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the embodiments can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., *Cloning Vectors: A Laboratory Manual*, 1985, supp. 1987; Weissbach and Weissbach, *Methods for Plant Molecular Biology*, Academic Press, 1989; and Flevin et al., *Plant Molecular Biology Manual*, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the embodiments. Screening to obtain lines displaying the desired expression level and pattern of the polynucleotides or of the Rcg1 locus may be accomplished by amplification, Southern analysis of DNA, northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, expression cassettes comprising a promoter operably linked to a heterologous nucleotide sequence of the embodiments are further provided. The expression cassettes of the embodiments find use in generating transformed plants, plant cells, and microorganisms and in practicing the methods for inducing plant fungal pathogen resistance disclosed herein. The expression cassette will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (Pinll) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoters of the polynucleotide sequences of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol.*

Biol. 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

It may sometimes be beneficial to express the genes from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, and are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the polypeptides of the embodiments within a particular plant tissue. For example, a tissue-preferred promoter may be used to express a polypeptide in a plant tissue where disease resistance is particularly important, such as, for example, the roots, the stalk or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, and are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of a polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2): 343-350). The TR1' gene, fused to nptll (neomycin phosphotransferase II) showed similar characteristics. Additional root-preferred promoters include the VfENOD-GRP3 gene promoter (Kuster et al. (1995) Plant Mol. Biol. 29(4):759-772); and rolB promoter (Capana et al. (1994) Plant Mol. Biol. 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, and are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, and are not limited to, bean β-phaseolin, napin, β-conglycinin, soybean lectin, cruciferin, and the like. For monocots, seed-specific promoters include, and are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP™ from Evrogen, see, Bolte et al. (2004) J. Cell Science 117:943-54). For additional selectable markers, see generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al (1987) Cell 49:603-612; Figge et al. (1988) Cell 52:713-722; Deuschle et al (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the embodiments.

The genes of the embodiments can be expressed as a transgene in order to make plants resistant to Cg. Using the different promoters described elsewhere in this disclosure, this will allow their expression in a modulated form in different circumstances. For example, one might desire higher levels of expression in stalks to enhance resistance to Cg-caused stalk rot. In environments where Cg-caused leaf blight is more of a problem, lines with higher expression levels in leaves could be used. However, one can also insert the entire genes, both native promoter and coding sequence, as a transgene. Finally, using the genes of the embodiments as transgenes will allow quick combination with other traits, such as insect or herbicide resistance.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing a line containing Rcg1 and Rcg1b (as transgenes or as an introgressed locus), with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

As shown in the Examples, the Rcg1 locus contains two components, Rcg1 and Rcg1b, which when expressed together provide the phenotype of the present invention. The skilled artisan will recognize that if the genes are to be used transgenically, this could be done on a single chimeric construct inserted into a plant cell to make a transgenic plant, but it could also be done by inserting the two genes as separate chimeric constructs into separate plant cells to make two transgenic plant lines. These could then be crossed and progeny lines carrying both genes selected using the methods described herein to obtain lines resistant to the pathogen. If one were to find a line in nature which expressed only one or the other gene, one could use a chimeric construct containing only the missing gene to make a transgenic line expressing both genes.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al., 1987, *Meth. Enzymol.* 143:277) and particle-accelerated or "gene gun" transformation technology (Klein et al., 1987, *Nature (London)* 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563, 055 and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, an expression cassette of the embodiments, stably incorporated into their genome.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant calli, plant clumps, and plant seeds. A plant cell is a cell of a plant, either taken directly from a seed or plant, or derived through culture from a cell taken from a plant. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance fungal plant pathogen resistance or protect from fungal pathogen attack in plants, especially corn (*Zea mays*). It will protect different parts of the plant from attack by pathogens, including and not limited to stalks, ears, leaves, roots and tassels. Other plant species may also be of interest in practicing the embodiments of the invention, including, and not limited to, other monocot crop plants.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

The embodiments of the present invention may be effective against a variety of plant pathogens, particularly fungal pathogens, such as, for example, *Colletotrichum*, including Cg. The embodiments of the present invention may also be effective against maize stalk rot, including anthracnose stalk rot, wherein the causative agent is *Colletotrichum*. Other plant pathogenic fungi and oomycetes (many of the latter of which have been historically been considered fungi although modern taxonomists have now classified them separately) include, and are not limited to, the following: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Microsphaera diffusa, Fusarium semitectum, Phialophora*

*gregata, Glomerella glycines, Phakopsora pachyrhizi, Pythium aphanidermatum, Pythium ultimum, Pythium debaryanum, Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Aphanomyces euteiches, Stemphylium herbarum, Stemphylium alfalfae, Colletotrichum trifolii, Leptosphaerulina briosiana, Uromyces striatus, Sclerotinia trifoliorum, Stagnospora meliloti, Stemphylium botryosum, Leptotrochila medicaginis;* Wheat: *Urocystis agropyri, Alternaria alternata, Cladosporium herbarum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici*-repentis, *Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana, Claviceps purpurea, Tilletia tritici, Tilletia laevis, Ustilago tritici, Tilletia indica, Rhizoctonia solani, Pythium arrhenomannes, Pythium gramicola, Pythium aphanidermatum;* Sunflower: *Plasmophora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Trichoderma viride, Claviceps sorghi, Erwinia chrysanthemi* pv. *zea, Erwinia carotovora, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium;* Sorghum: *Exserohilum turcicum, Colletotrichum graminicola (Glomerella graminicola), Cercospora sorghi, Gloeocercospora sorghi, Ascochyta sorghina, Puccinia purpurea, Macrophomina phaseolina, Perconia circinata, Fusarium moniliforme, Alternaria altemata, Bipolaris sorghicola, Helminthosporium sorghicola, Curvularia lunata, Phoma insidiosa, Ramulispora sorghi, Ramulispora sorghicola, Phyllachara sacchari, Sporisorium reilianum (Sphacelotheca reiliana), Sphacelotheca cruenta, Sporisorium sorghi,* *Claviceps sorghi, Rhizoctonia solani, Acremonium strictum, Sclerophthona macrospora, Peronosclerospora sorghi, Peronosclerospora philippinensis, Sclerospora graminicola, Fusarium oxysporum, Pythium arrhenomanes, Pythium graminicola,* etc.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

The term "allele" refers to one of two or more different nucleotide sequences that occur at a specific locus. A first allele is found on one chromosome, while a second allele occurs at the same position on the homologue of that chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., resistance to Cg infection. A favorable allele of a marker is a marker allele that segregates with the favorable phenotype. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) of an allele within a population, or a population of lines. One can estimate the allele frequency within a population by averaging the allele frequencies of a sample of individuals from that population.

An allele "positively" correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). A special case of a heterozygous situation is where one chromosome has an allele of a gene and the other chromosome lacks that gene, locus or region completely—in other words, has a deletion relative to the first chromosome. This situation is referred to as "hemizygous." In this situation the allele on the chromosome lacking the gene, locus or region may also be referred to as the "null allele." The term "homogeneity" indicates that members of a group have the same genotype at one or more specific loci. In contrast, the term "heterogeneity" is used to indicate that individuals within the group differ in genotype at one or more specific loci.

The embodiments provide not only a gene and its functional variants for use in transgenic applications, but sequences and processes that allow the Rcg1 and Rcg1b resistance genes to be moved between corn lines using marker assisted breeding. The embodiments also relate to plants produced by these processes that retain a truncated chromosomal interval comprising the Rcg1 and Rcg1b resistance genes.

A genetic map is a graphical representation of a genome (or a portion of a genome such as a single chromosome) where the distances between landmarks on a chromosome are measured by the recombination frequencies between the landmarks. Recombinations between genetic landmarks can be detected using a variety of molecular genetic markers (also called molecular markers) that are described in more detail herein.

For markers to be useful at detecting recombinations, they need to detect differences, or polymorphisms, within the population being monitored. For molecular markers, this means differences at the DNA level due to polynucleotide sequence differences (eg SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs). ESTs are generally well conserved within a species, while other regions of DNA (typically non-coding) tend to accumulate polymorphism, and therefore, can be more variable between individuals of the same species. A large number of corn molecular markers are known in the art, and are published or available from various sources, such as the Maize GDB internet resource and the Arizona Genomics Institute internet resource run by the University of Arizona.

Molecular markers can be used in a variety of plant breeding applications (eg see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in the plants development, e.g. kernel characteristics. Since DNA marker assays are less laborious, and take up less physical space, than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination can not occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, as in the case of the Rcg1 locus being introgressed from MP305, an exotic source, into elite inbreds, these flanking regions carry additional genes that may code for agronomically undesirable traits. This "linkage drag" may also result in reduced yield or other negative agronomic characteristics even after multiple cycles of backcrossing into the elite corn line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, a series of flanking markers surrounding the gene can be utilized to select for recombinations in different population sizes. For example, in smaller population sizes recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors 4 map [online], [retrieved on 2006 Mar. 21]. Retrieved from the Internet<URL: http://www.maizegdb.org/cgi-bin/displaymaprecord.cgi?id=871214>.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The three types of markers described in this disclosure can be used in marker assisted selection protocols; simple sequence repeat (SSR, also known as microsatellite) markers, single nucleotide polymorphism (SNP) markers and fragment length polymorphic (FLP) markers. SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics*, 88:1-6). Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet* 44:388-396). SSRs are highly suited to mapping and MAS as they are multi-allelic, codominant, reproducible and amenable to high throughput automation (Rafalski et al. (1996) Generating and using DNA markers in plants. In: *Nonmammalian genomic analysis: a practical guide*. Academic press. pp 75-135).

For example, an SSR marker profile of MP305 is provided in Example 5 herein. This marker profile was generated by gel electrophoresis of the amplification products generated by the primer pairs for these markers. Scoring of marker genotype is based on the size of the amplified fragment, which in this case was measured by the base pair weight of the fragment. While variation in the primer used or in laboratory procedures can affect the reported base pair weight, relative values will remain constant regardless of the specific primer or laboratory used. Thus, when comparing lines, the SSR profiles being compared should be obtained from the same lab, so that the same primers and equipment is used. For this reason, when comparing plants or lines vis a vis specific markers, it is preferable to state that such plants or lines have the same (or different) alleles at specified loci (e.g. one can say that if a plant does not comprise the MP305 derived chromosomal interval at or below UMC15a, it will not comprise the same alleles as MP305 at all of the loci at or below UMC15a listed on Table 5b in Example 5). An SSR service for corn is available to the public on a contractual basis by DNA Landmarks in Saint-Jean-sur-Richelieu, Quebec, Canada.

Various types of FLP markers can be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). Plant Mol Biol 48, 539-547; Rafalski (2002b), supra). The term "indel" refers to an insertion or deletion, wherein one line may be referred to as having an insertion relative to a second line, or the second line may be referred to as having a deletion relative to the first line. The MZA markers disclosed herein are examples of amplified FLP markers that have been selected because they are in close proximity to the Rcg1 and Rcg1b genes.

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp. 475-492; Shi (2001) Clin Chem 47, pp. 164-172; Kwok (2000) Pharmacogenomics 1, pp. 95-100; Bhattramakki and Rafalski (2001) Discovery and application of single nucleotide polymorphism markers in plants. In: R. J. Henry, Ed, Plant Genotyping: The DNA Fingerprinting of Plants, CABI Publishing, Wallingford. A wide range of commercially available technologies utilize these and other methods to interrogate SNPs including MASS-CODE™ (Qiagen), INVADER™ (Third Wave Technologies, Madison, Wis.), SNAPSHOT® (Applied Biosystems), TAQMAN® (Applied Biosystems) and BEADARRAYS™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), supra). Haplotypes can be more informative than single SNPs and can be more descriptive of any particular genotype. For example, a single SNP may be allele 'T' for MP305, but the allele 'T' might also occur in the maize breeding population being utilized for recurrent parents. In this case, a haplotype, e.g. a series of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

As described herein, many of the primers listed in Tables 1 and 2 can readily be used as FLP markers to select for the Rcg1 locus. These primers can also be used to convert these markers to SNP or other structurally similar or functionally equivalent markers (SSRs, CAPs, indels, etc), in the same regions. One very productive approach for SNP conversion is described by Rafalski (2002a) Current opinion in plant biology 5 (2): 94-100 and also Rafalski (2002b) Plant Science 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs as described above, other types of molecular markers are also widely used, including but not limited to expressed sequence tags (ESTs) and SSR markers derived from EST sequences, and randomly amplified polymorphic DNA (RAPD). As used herein, the term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al., 1995, Nucleic Acids Res. 23:4407-4414), Single Nucleotide Polymorphism (SNP) (Brookes, 1999, Gene 234:177-186), Sequence Characterized Amplified Region (SCAR) (Paran and Michelmore, 1993, Theor. Appl. Genet. 85:985-993), Sequence Tagged Site (STS) (Onozaki et al., 2004, Euphytica 138:255-262), Single Stranded Conformation Polymorphism (SSCP) (Orita et al., 1989, Proc Natl Acad Sci USA 86:2766-2770), Inter-Simple Sequence Repeat (ISSR) (Blair et al., 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet. 98:704-711), an RNA cleavage product (such as a Lynx tag) and the like.

More generically, the term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-colinear region described herein. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g. SNP technology is used in the examples provided herein.

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers.

For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

Figure 9A:
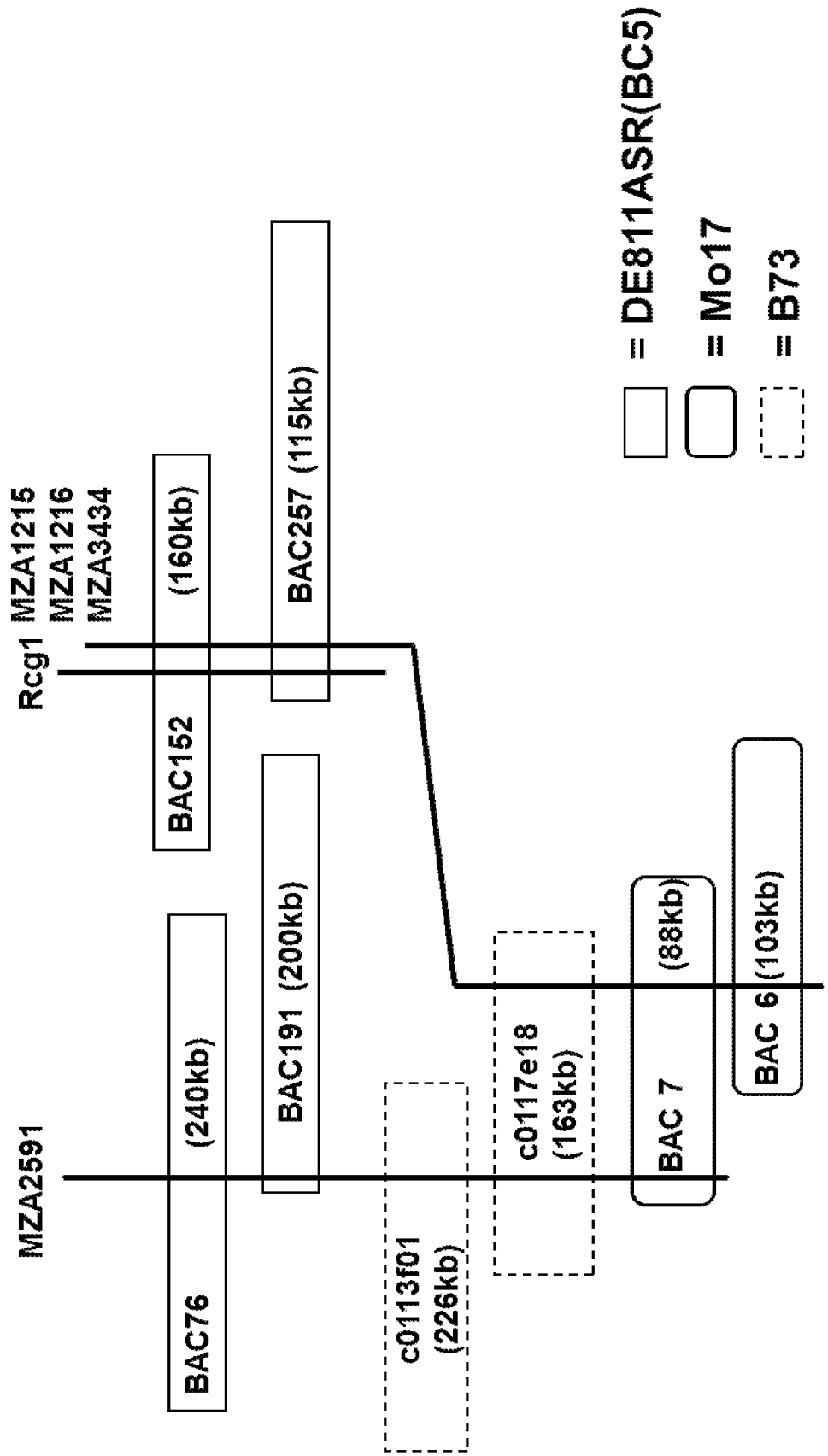
FIGS. 9a and 9b.

As noted in Example 2, by using common sequences from the region flanking the Rcg1 locus that hybridized to BACs in the Mo17 and the B73 BAC libraries, the BACs from both libraries were lined up with BACs from the DE811ASR (BC5) homologous region flanking the Rcg1 locus in a tiling path as shown in FIG. 9(a). The public B73 BACs, c0113f01 and c0117e18 were identified as directly north and south, respectively, of the Rcg1 locus.

With this information, an extended non-contiguous tiling path of B73 BACs between genetic markers UMC2285 and UMC15a, UMC2285 and UMC2187, UMC1086 and UMC2200, or UMC2041 and UMC2200, can be created by aligning genetic markers within this region with the physical map of the B73 BAC. Alignment information of the genetic and physical maps of B73 is obtained from the maize genome database of the Arizona Genomics Institute on the world wide web, accessed by entering the following web address prefixed by "www.": genome.arizona.edu/fpc/maize/#webagcol. In the WebChrom view, one can select the genetic markers in the vicinity of the Rcg1 and Rcg1b genes and get a link to the physical contig where these genetic markers are located. By aligning the physical map in such way with the genetic map one can find a plethora of B73 BACs in the region between the chromosomal intervals defined by genetic markers UMC2285 and UMC15a, UMC2285 and UMC2187, UMC1086 and UMC2200, or UMC2041 and UMC2200. The BACs can be used by one of ordinary skill in the art to develop new markers for introgression of the Rcg1 locus into maize germplasm. In particular, such genetic markers would be useful for tracking the Rcg1 locus in any lines into which the Rcg1 locus or Rcg1 and Rcg1b genes have been introgressed, and for selecting for recurrent parent genome in a backcrossing program.

Figure 21:
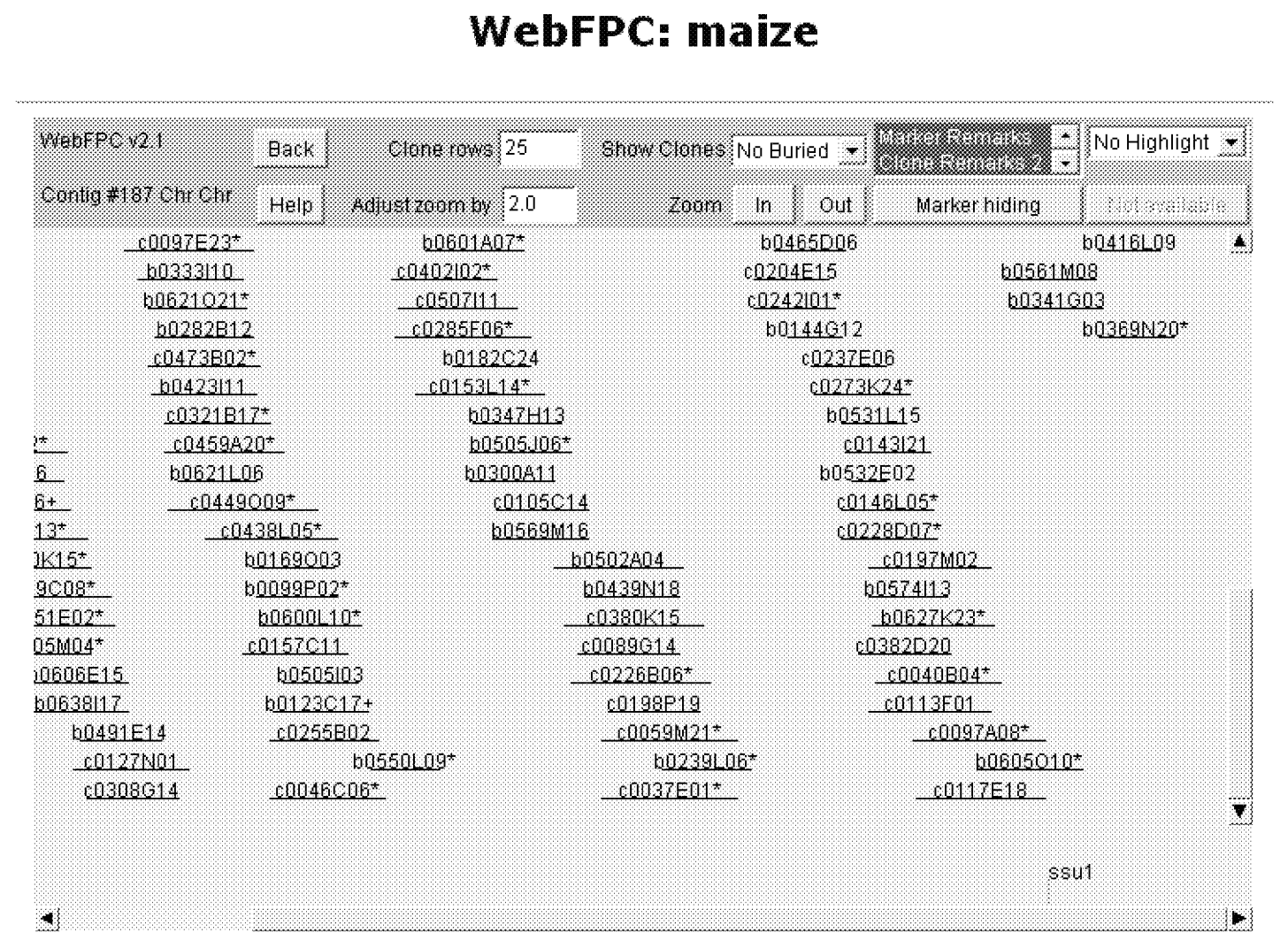

For example, in order to design polymorphic markers that will be useful for introgression and selection of the Rcg1 and Rcg1b genes, or the Rcg1 locus in other maize germplasm, sequence information of the region surrounding the Rcg1 locus can be used. There are many B73 derived bacterial artificial chromosomes (BACs) available in the region of interest from which sequence information can be obtained. An example of BACs in the region of interest is shown in FIG. 21, which shows a contig on the B73 physical map that is homologous to the Rcg1 and Rcg1b region in DE811ASR (BC5) [FIG. 21 retrieved 2006 Mar. 10]. Retrieved from the Internet <URL: http://www.genome.arizona.edu/cgi-bin//WebAGCoL/WebFPC/WebFPC_Direct_v2.1.cgi?name=maize&contig=187&marker=ssu1>. Sequence information is obtained either through information that is already publicly available (e.g. BAC end-sequence, sequence of Expressed Sequence Tags (ESTs) that hybridize to BACs in this region, overgo probes that often relate to these ESTs, etc.) or by obtaining new sequence by directly sequencing BAC clones in this region. From this sequence one can determine which regions are most unique using several different methods known to one of ordinary skill in the art. For example, by using gene prediction software or by comparing the sequence using BLAST® against all available maize sequence, one can select for non-repetitive sequence. Low copy sequence can be used to develop a wide array of nucleic acid based markers. These markers are used to screen the plant material in which the Rcg1 locus is present and the plant material in which the Rcg1 locus is absent. If a marker outside of the Rcg1 locus is desired, then the markers are used to screen the plant material in which the Rcg1 locus is present and the plant material in which the Rcg1 locus is absent to determine if the marker is polymorphic in such germplasm. Polymorphic markers are then used for marker assisted introgression and selection of the Rcg1 region and optimally also recurrent parent genome selection, in other maize germplasm. Thus, with the location of the Rcg1 locus identified and its association with resistance to *Colletotrichum* established, one of ordinary skill in the art can utilize any number of existing markers, or readily develop new markers, that can be used introgress or identify the presence or absence of the Rcg1 locus in germplasm, and to select for recurrent parent genome in a backcrossing program.

On a genetic map, linkage of one molecular marker to a gene or another molecular marker is measured as a recombination frequency. In general, the closer two loci (e.g., two SSR markers) are on the genetic map, the closer they lie to each other on the physical map. A relative genetic distance (determined by crossing over frequencies, measured in centimorgans; cM) can be proportional to the physical distance (measured in base pairs, e.g., kilobase pairs [kb] or megabasepairs [Mbp]) that two linked loci are separated from each other on a chromosome. A lack of precise proportionality between cM and physical distance can result from variation in recombination frequencies for different chromosomal regions, e.g., some chromosomal regions are recombination "hot spots," while others regions do not show any recombination, or only demonstrate rare recombination events. Some of the introgression data and mapping information suggest that the region around the Rcg1 locus is one that does have a high amount of recombination.

In general, the closer one marker is to another marker, whether measured in terms of recombination or physical distance, the more strongly they are linked. The closer a molecular marker is to a gene that encodes a polypeptide that imparts a particular phenotype (disease resistance), whether measured in terms of recombination or physical distance, the better that marker serves to tag the desired phenotypic trait. If possible, the best marker is one within the gene itself, since it will always remain linked with the gene causing the desired phenotype.

Genetic mapping variability can also be observed between different populations of the same crop species, including maize. In spite of this variability in the genetic map that may occur between populations, genetic map and marker information derived from one population generally remains useful across multiple populations in identification of plants with desired traits, counter-selection of plants with undesirable traits and in guiding MAS.

To locate equivalent markers across genetic maps, a mapping population may be used to confirm whether any such equivalent marker is within the region described herein and therefore useful for selection of the Rcg1 locus. Using this method, the equivalent marker, along with the markers listed herein, are mapped on such mapping population. Any equivalent marker that falls within the same region can be used to select for Rcg1. Mapping populations known in the art and that may be used for this purpose include, but are not limited to, the IBM populations and T218×GT119 IF2 population described in Sharopova, N. et al. (2002) Plant Mol Biol 48(5):463-481 and Lee, M. et al. (1999): Tools for high resolution genetic mapping in maize—status report. Proc. Plant Animal Genome VII, Jan. 17-21, 1999, San Diego, USA, P. 146; the UMC 98 population, described in Davis, G. L. et al. (1999) *Genetics* 152(3):1137-72 and in Davis, M. D. et al., (1998) The 1998 UMC Maize Genetic Map: ESTs, Sequenced Core Markers, and Nonmaize Probes as a Foundation for Gene Discovery, *Maize Genetics Conference Abstracts* 40.

As used herein, "introgression" or "introgressing" shall refer to moving a gene or locus from one line to another by: (1) crossing individuals of each line to create a population; and (2) selecting individuals carrying the desired gene or locus. Selection may be done phenotypically or using markers (marker assisted selection). The individuals so selected are again crossed (i.e., backcrossed) with the desired target line; there may be two, three, four, five, six or more, or even ten or more backcrosses. After each cross, the selection process is repeated. For example, the gene of the embodiments, or the locus containing it, may be introgressed into a recurrent parent that is not resistant or only partially resistant, meaning that it is sensitive or susceptible or partially so, to Cg. The recurrent parent line with the introgressed gene or locus then has enhanced or newly conferred resistance to Cg. This line into which the Rcg1 locus has been introgressed is referred to herein as an Rcg1 locus conversion.

The process of introgressing is often referred to as "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires (Les Colloques, Vol. 72, pp. 45-56 and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

In the case of the Rcg1 locus, where the sequences of the genes responsible for its phenotypic effect and very nearby regions are available, DNA markers based on the genes themselves or closely linked sequences can be developed for direct selection of the donor genes in the recurrent parent background. While any polymorphic DNA sequence from the chromosomal region carrying the gene could be used, the sequences provided in the embodiments allow the use of DNA markers within or close to the genes, minimizing false positive selection for the genes. Flanking markers limit the size of the donor genome fragments introduced into the recipient background, thus minimizing so called "linkage drag," meaning the introduction of undesirable sequences from the donor line that could impact plant performance in otherwise elite germplasm. The embodiments provide multiple examples of DNA markers that could be so used, and the person skilled in the art will be able to use the genomic sequences provided to create even more markers. An example is to use markers that hybridize (in the case of RFLP assays) or anneal (in the case of PCR assays) specifically (exclusively) to sequences closely linked, including within, the locus. In principle, sequences that also hybridize or anneal elsewhere in the genome could be used if several such markers are used in combination. When PCR reactions are used, in practice the length of the primers used in the amplification reaction should be at least about 15 nucleotides, but depending on the sequences and hybridization conditions, any length that provides specific annealing can be used, such as about 16, about 17, about 18, about 19, about 20, about 21, about 22, about 23, about 24, about 25, about 26, about 27, about 28 or longer. For PCR reactions the term "anneal" is commonly used, and as used herein it shall be understood to have the same meaning as "hybridize."

Thus, by using the markers and processes described herein, one may produce a plant comprising a truncated chromosomal interval comprising the Rcg1 locus and/or the Rcg1 and Rcg1b genes. The term "chromosomal interval" or "chromosomal segment" refers to a contiguous linear span of genomic DNA that resides in planta on a single chromosome, usually defined with reference to two markers defining the end points of the chromosomal interval. The specified interval may include the markers at the end points (e.g. one or more markers on or within the chromosomal interval defined by marker A and marker B) or may exclude the markers at the end points of the interval (e.g. one or more markers within the chromosomal interval defined by marker A and marker B). A truncated chromosomal interval refers to a chromosomal interval that has been reduced in size by selecting for one or more recombination events that have reduced the size of the chromosomal interval. A "recombination event" refers to the occurrence of recombination between homologous chromosomes, and refers to a specific chromosomal location where such a recombination has occurred (e.g. a recombination of a chromosomal interval internal to the end points of the chromosome will have a recombination event at each end of the chromosomal interval). The truncated chromosomal interval may be defined with reference to one or both new markers at the end points of the segment. The length of two chromosomal segments may be measured by either centimorgans or base pairs. The genetic elements or genes located on a single chromosomal interval are physically linked. The size of a chromosomal interval is not particularly limited, but in the context of the embodiments of the present invention, generally the genetic elements located within a single chromosomal interval are also genetically linked.

By using the processes of the embodiments, it is possible to select for a plant that comprises a truncated chromosomal interval comprising the Rcg1 and Rcg1b genes. Specifically, with respect to the invention described in more detail in the examples below, the chromosomal interval may be reduced to a length of 12 cM or less, 10 cM or less, 8 cM or less, 6 cM or less, 4 cM or less, 3 cM or less, 2.5 cM or less, 2 cM or less, 1.5 cM or less, 1 cM or less, 0.75 cM or less, in each case as measured with respect to the map distances as shown on the IBM2 Neighbors 4 genetic map as in effect on Mar. 21, 2006. As measured in base pairs, the chromosomal interval may be reduced to a length of 15 mbp or less, 10 mbp or less, 5 mbp or less, 3 mbp or less, 1 mpb or less, 500 kbp or less. One of ordinary skill in the art would understand that it is undesirable to cause a break in the chromosomal region so proximal to the Rcg1 or Rcg1b coding sequences (e.g. within 5 kbp or less, within 4 kbp or less, 3 kbp or less, 2 kbp or less, 1 kbp or less), such that the promoter and other upstream regulatory elements would be unlinked from the coding sequence.

The term "locus" generally refers to a genetically defined region of a chromosome carrying a gene or, possibly, two or more genes so closely linked that genetically they behave as a single locus responsible for a phenotype. When used herein with respect to Rcg1, the "Rcg1 locus" shall refer to the defined region of the chromosome carrying the Rcg1 and Rcg1b genes including their associated regulatory sequences, plus the region surrounding the two genes that is non-colinear with B73, or any smaller portion thereof that retains the Rcg1 and Rcg1b genes and associated regulatory sequences. This locus has also been referred to elsewhere as the ASR locus, and will be referred to as the Rcg1 locus here.

A "gene" shall refer to a specific genetic coding region within a locus, including its associated regulatory sequences. The region encoding the Rcg1 primary transcript, referred to herein as the "Rcg1 coding sequence", will be used to define the position of the Rcg1 gene, and one of ordinary skill in the art would understand that the associated regulatory sequences will be within a distance of about 4 kb from the Rcg1 coding sequence, with the promoter located upstream. The region encoding the Rcg1b primary transcript, referred to herein as the "Rcg1b coding sequence", will be used to define the position of the Rcg1b gene, and one of ordinary skill in the art would understand that the associated regulatory sequences will be within a distance of about 4 kb (i.e. about 4 kb, about 3 kb, about 2 kb, about 1 kb, or about 0.5 kb) from the Rcg1b coding sequence, with the promoter located upstream. One embodiment of the present invention is the isolation of the Rcg1 and Rcg1b genes and the demonstration that they together are the genes responsible for the phenotype conferred by the presence of the locus.

As will be appreciated by the skilled artisan, the structure of the Rcg1 locus brings with it special considerations when using MAS to work with this locus. It comprises two genes (Rcg1 and Rcg1b) located within less than a centimorgan of each other that are each necessary for the phenotype conferred by the presence of the locus. Physically the two genes are approximately 200-300 kb apart. This means that the chances of recombination between the two genes, so that they are separated, is very low, meaning less than 1%, on a chromosome the size of chromosome 4 (approximately 250 megabases, or 250,000 kb). There are several reasons for this.

1. The physical distance represents about 0.1% (i.e., as a fraction 0.001) of the length of the chromosome. If recombination occurs randomly, the chance of a recombination event in this region is clearly low.
2. While recombination frequencies are not identical at different locations in the genome, the average physical distance per centimorgan (1% recombination—see Suzuki, Griffiths, Miller and Lewontin, (1986) An Introduction to Genetic Analysis, Third Edition, Freeman & Company, New York, page 84) is approximately 1,000 kb. 200-300 kb would thus represent less than 1 cM, or less than 1% recombination. The number of recombination events found in Example 1 in the general region flanking the locus is not unusually large.
3. As shown in Example 2, the locus is present on a chromosomal region from MP305 that is not present in DE811 and in fact in many other lines commonly used as breeding sources for commercial lines. This region is referred to herein as the noncolinear region. In such cases, there can be no recombination because there is no homologous region on the other chromosome. Consistent with this, in Example 1 recombination events were found only outside of the region introgressed from MP305. This specific reasoning will apply only to lines not containing a segment homologous to the MP305 region, but the skilled artisan will easily be able to determine this using the methods outlined in Example 11.

Taken together, this means that while in principle, to avoid any chance of separating the two genes, one should use markers outside the interval defined by the two genes, as a practical matter one could use markers within either gene, or in the interval between them, to follow and successfully introgress both genes. The statistical chance of losing one or the other gene is less than 1%, as described above, and even that risk can be avoided with the various assays for the presence of the individual genes (including but not limited to gene specific PCRs, RT-PCR, westerns, ELISAs and other methods previously mentioned). Therefore, embodiments of this invention include both methods to use MAS in a way that avoids any risk of losing either gene, by using markers flanking the interval defined by the genes, but also methods based on following only one or the other gene, or the region between them, combined with the appropriate assays to make sure that both genes are present.

It should further be noted that because the two genes are so tightly linked, previous workers would not have observed them as two genes. Thus these two genes do not represent the two genetically separable genes on the long arm of chromosome 4 that confer resistance to Cg previously reported (Toman, et al., (1993), *Phytopathology*, 83:981-986; Cowen, N et al. (1991) Maize Genetics Conference Abstracts 33). The two genes together on the Rcg1 locus of the present invention may represent one of the two genetically separable loci, which have previously been reported, but which have not previously been associated with a particular gene or finely mapped locus.

As used herein, "linked" or "linkage" (as distinguished from the term "operably linked") shall refer to the genetic or physical linkage of loci or genes. Loci or genes are considered genetically linked if the recombination frequency between them is less than about 50% as determined on a single meiosis map. They are progressively more linked if the recombination frequency is about 40%, about 30%, about 20%, about 10% or less, as determined on a single meiosis map. Two or more genes are physically linked (or syntenic) if they have been demonstrated to be on a single piece of DNA, such as a chromosome. Genetically linked genes will in practice be physically linked (or syntenic), but the exact physical distance (number of nucleotides) may not have been demonstrated yet. As used herein, the term "closely linked" refers to genetically linked markers within 15 cM or less, including without limitation 12 cM or less, 10 cM or less, 8 cM or less, 7 cM or less, 6 cM or less, 5 cM or less, 4 cM or less, 3 cM or less, 2 cM or less, 1 cM or less and 0.5 cM or less as determined on the IBM2 neighbors 4 genetic map publicly available on the Maize GDB website previously referenced in this disclosure. Distances 1 cM or less and 0.5 cM or less can also be considered very closely, or tightly, linked. A DNA sequence, such as a short oligonucleotide representing a sequence within a locus or one complementary to it, is also linked to that locus.

A "line" or "strain" is a group of individuals of identical parentage that are generally inbred to some degree and that are generally homozygous and homogeneous at most loci.

An "ancestral line" or "progenitor" is a parent line used as a source of genes, e.g., for the development of elite lines. "Progeny" are the descendents of the ancestral line, and may be separated from their ancestors by many generations of breeding. For example, many elite lines are the progeny of B73 or Mo17. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite variety" is an agronomically superior line or variety that has resulted from many cycles of breeding and selection for superior agronomic performance. An "elite inbred line" is an elite line that is an inbred, and that has been shown to be useful for producing sufficiently high yielding and agronomically fit hybrid varieties (an "elite hybrid variety"). Numerous elite lines and varieties are available and known to those of skill in the art of corn breeding. Similarly, "elite germplasm" is an agronomically superior germplasm, typically derived from and/or capable of giving rise to a plant with superior agronomic performance, such as an existing or newly developed elite line of corn.

In contrast, an "exotic corn line" or "exotic corn germplasm" is germplasm derived from corn not belonging to an available elite line, elite variety or elite germplasm. In the context of a cross between two corn plants, an exotic line or exotic germplasm is not closely related by descent to the elite line, elite variety or elite germplasm with which it is crossed. Most commonly, the exotic line or exotic germplasm is selected to introduce novel genetic elements (typically novel alleles) into a breeding program.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

With respect to map directions noted herein, instead of the terms 5' and 3', the terms "north" and "above" are used (e.g., a marker north of the Rcg1 locus refers to a marker above the Rcg1 locus, as determined with reference to the maps provided in a vertical orientation, such as FIGS. 7 and 8, and to the left of the Rcg1 locus, as determined with reference to maps provided in a horizontal orientation, such as FIG. 22). Likewise, the terms "south" and "below" are used (e.g. a marker south of the Rcg1 locus refers to a marker below the Rcg1 locus, as determined with reference to the vertically oriented maps provided herein, and to the right of the Rcg1 locus, as determined with reference to the horizontally oriented maps provided herein). More specifically, for example, above the Rcg1 coding sequence refers to the chromosome above, or north of the primary transcript in SEQ ID NO: 1 (at about FLP110F), and below the Rcg1 coding sequence refers to the chromosome below or south of the primary transcript in SEQ ID NO: 1 (at about FLPA1R). See FIG. 26. The term "proximal" and "distal" are relative terms meaning, respectively, nearer and farther from a specified location (e.g., the Rcg1b or Rcg1 genes) when used to compare two points on a map relative to the specified location.

A phenotypic assay is an assay in which, instead of using molecular markers to follow a trait or characteristic, the phenotype of the plant with respect to the trait or characteristic is checked. For any given trait or characteristic the skilled artisan will be able to develop or find in the literature numerous phenotypic assays. For example, two phenotypic assays for resistance to *Colletotrichum* graminicola are the leaf blight assays described in Example 12 and the stalk infection assay described in Example 14. Other phenotypic assays for resistance to *Colletotrichum* assays are possible.

The term "computer systems" refers generally to various automated systems used to perform some or all of the method steps described herein. The term "instructions" refers to computer code that instructs the computer system to perform some or all of the method steps. In addition to practicing some or all of the method steps, digital or analog systems, e.g., comprising a digital or analog computer, can also control a variety of other functions such as a user viewable display (e.g., to permit viewing of method results by a user) and/or control of output features (e.g., to assist in marker assisted selection or control of automated field equipment).

Certain of the methods described herein are optionally (and typically) implemented via a computer program or programs (e.g., that store and can be used to analyze molecular marker data). Thus, the embodiments provide digital systems, e.g., computers, computer readable media, and/or integrated systems comprising instructions (e.g., embodied in appropriate software) for performing the methods herein. The digital system will include information (data) corresponding to plant genotypes for a set of genetic markers, and optionally, phenotypic values and/or family relationships. The system can also aid a user in performing marker assisted selection for the Rcg1 locus according to the methods herein, or can control field equipment which automates selection, harvesting, and/or breeding schemes.

Standard desktop applications such as word processing software (e.g., MICROSOFT® WORD or COREL® WORDPERFECT®) and/or database software (e.g., spreadsheet software such as MICROSOFT® EXCEL®, COREL® QUATTRO PRO®, or database programs such as MICROSOFT® ACCESS™ or PARADOX®) can be adapted to the embodiments by inputting data which is loaded into the memory of a digital system, and performing an operation as noted herein on the data. For example, systems can include the foregoing software having the appropriate genotypic data, and optionally pedigree data, used in conjunction with a user interface (e.g., a GUI in a standard operating system such as a WINDOWS®, MACINTOSH® or LINUX® system) to perform any analysis noted herein, or simply to acquire data (e.g., in a spreadsheet) to be used in the methods herein. The computer can be, e.g., a PC (INTEL® x86 or PENTIUM® chip-compatible MS-DOS®, OS/2®, WINDOWS®, WINDOWS NT®, WINDOWS® 95, WINDOWS® 98, LINUX®, Apple®-compatible, MACINTOSH® compatible, POWER PC® compatible, or a UNIX® compatible (e.g., SUN™ work station) machine) or other commercially common computer which is known to one of skill. Software for performing association analysis and/or phenotypic value prediction can be constructed by one of skill using a standard programming language such as VISUAL BASIC®, FORTRAN®, Basic, JAVA®, or the like, according to the methods herein.

Any system controller or computer optionally includes a monitor, which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of genetic marker genotype, phenotypic value, or the like in the relevant computer system.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to an appropriate language for instructing the system to carry out any desired operation. For example, a digital system can instruct selection of plants comprising certain markers, or control field machinery for harvesting, selecting, crossing or preserving crops according to the relevant method herein.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

EXAMPLES

The embodiments of the invention are further defined in the following examples, in which all parts and percentages are by weight and degrees are Celsius, unless otherwise stated. It should be understood that these examples, while indicating embodiments of the invention, are given by way of illustration only. From the above discussion and these examples, one skilled in the art can ascertain the essential characteristics of the embodiments of this invention, and without departing from the spirit and scope thereof, can make various changes and modifications to adapt it to various usages and conditions. Thus, various modifications of the embodiments of the invention in addition to those shown and described herein will be apparent to those skilled in the art from the foregoing description. Such modifications are also intended to fall within the scope of the appended claims. The disclosure of each reference set forth herein is incorporated by reference in its entirety. Examples 5 and 15 are actual in part and prophetic in part. All other examples are actual.

Example 1

Fine Mapping of the Rcg1 Locus to a Specific Region of 4 L

In order to map and clone the gene responsible for the resistance of corn line MP305 to Cg, lines had previously been created which differed as little as possible from each other genetically with the exception of the presence of the locus responsible for the resistant phenotype. Such lines are called near isogenic lines. To this end, DE811 had been crossed to MP305 and the progeny had been backcrossed to the sensitive line DE811 three times, at each backcross selecting for resistance to Cg and otherwise for characteristics of DE811 (Weldekidan and Hawk, (1993), *Maydica,* 38:189-192). The resulting line was designated DE811ASR (BC3) (Weldekidan and Hawk, (1993) supra). This line was used as the starting point for the fine mapping of the Rcg1 locus. It was first necessary to know roughly where in the maize genome it was located. Using standard genetic methods, Jung et al. ((1994) supra) had previously localized the locus on the long arm of chromosome 4.

Since the Rcg1 locus had previously been mapped to the long arm of maize chromosome 4, using the information on markers near the locus obtained by Jung et al. (1994) supra, all available public and private simple sequence repeat (SSR) markers located in the region of the chromosome designated 4.06-4.08 were analyzed to determine if these markers were polymorphic between the two near isogenic lines DE811 and DE811ASR (BC5). The DE811ASR (BC5) line was derived from the DE811ASR (BC3) line described by Weldekidan and Hawk (1993), supra through two backcrosses to DE811 under selection for resistance to Cg, followed by 5 generations of selfing and selection to obtain the BC5 line. The BC5 line was backcrossed twice more to DE811 to create the BC7 segregating population used for fine mapping. In order to be able to conduct phenotypic evaluation on a family basis, BC7 individuals were selfed to create BC7S1 families.

From this analysis two SSR markers, PHI093 and UMC2041, were discovered to be polymorphic. Using the publicly available inter-mated (Coe et al. (2002) *Plant Physiol.* 128:9-12; Gardiner, et al., (2004), *Plant Physiol.*, 134:1317-1326; Yim et al., (2002) *Plant Physiol.* 130:1686-1696) B73×Mo17 (IBM) neighbors map (Lee et al. (2002) Plant Mol Biol 48:453-61; Sharopova et al., (2002) *Plant Mol Biol* 48:463-81), the sequences of three nearby Restriction Fragment Length Polymorphism (RFLP) markers, CD0365, CSU166 and CD0127, were used to create fragment length polymorphic markers (hereafter designated FLPs). FLPs are markers that can be assayed using gel electrophoresis or any similar high-resolution fragment separation method following a PCR reaction using primers of a defined sequence. All three markers were found to be polymorphic. The FLPs used in mapping the Rcg1 locus are summarized in Table 1. Any primers for the MZA FLPs shown on Table 1, which also have the same MZA markers names shown on Table 2, will amplify a region of the FLP internal to the internal sequence shown on Table 2. The annealing temperature for all the primers listed in Table 1 is 60° C.

In order to determine whether the presence of these three polymorphic FLPs and two polymorphic SSRs was associated with the resistant phenotype, indicating that the region carrying the Rcg1 locus was located on a chromosomal segment containing these three markers, a table was created in which the phenotypic status of 4784 individuals determined by field observation and the genotypic status relative to each of the five markers, determined by fragment size analysis, were entered. This data was submitted sequentially to the software programs Joinmap (Van Ooijen, et al., (2001), *Plant Research International, Wageningen, the Netherlands*) and Windows QTL Cartographer (Wang, et al., (2004), (online, version 2.0 retrieved on 2004 Jun. 14 and version 2.5 retrieved on 2005 Feb. 22); retrieved from the North Carolina State University Statistical Genetics and Bioinformatics website on the Internet <URL: http://statgen.ncsu.edu/qtlcart/WQTLCart.htm>. The former program determines the order of the markers along the chromosomal region. The latter determines if a particular allele of a marker (a particular form of the two polymorphic forms of the marker) is significantly associated with the presence of the phenotype. Markers for which the presence of one or the other allele is more significantly associated with the resistant phenotype are more likely to be closer to the gene responsible for the resistant phenotype. FIG. 3 depicts a graph produced by Windows QTL Cartographer showing a statistical analysis of the chance (Y axis) that the locus responsible for the Cg resistance phenotype is located at a particular position along the chromosome (X axis) as defined by FLP markers.

From the integrated physical and genetic map as described by Fengler, et al., ((2004) Plant and Animal Genome XII Abstract Book, Page 192 (Poster number P487), January 10-14, San Diego, Calif.) and Gardiner, (2004) supra, it was possible to identify two bacterial artificial chromosome (BAC) contigs, derived from a Mo17 BAC library, harboring the above mentioned genetic markers.

However, the two BAC contigs containing the markers flanking the region of interest contained a gap of unknown size. In order to identify further BACs to bridge this gap, a dense genetic map containing markers (Fengler, (2004) supra) with known positions on the physical map was used to find additional markers genetically linked to markers previously identified on the two BAC contigs. These additional markers in Table 2, were used to identify BAC contigs from a B73 BAC library which closed the physical gap between the previously found Mo17-derived BAC contigs (Coe et al. (2002) supra; Gardiner (2004) supra; Yim et al. (2002) supra. Four markers, MZA11455, MZA6064, MZA2591 and MZA15842, were used for mapping purposes. In Table 2, "E" stands for "external" and "I" stands for "internal," which respectively refer to the outer and inner primers used during nested PCR. The external set is used in the first round of PCR, after which the internal sequences are used for a second round of PCR on the products of the first round. This increases the specificity of the reaction. Upper case letters indicate portions of the primer based on vector sequences, which are later used to sequence the PCR product. They are not maize sequences. For the forward internal nested MZA primers, the upper case portion of the sequence is SEQ ID NO: 126, and for the reverse internal nested MZA primers, the upper case portion is SEQ ID NO: 127. The sequences shown in Table 2 for the internal forward MZA nested primers are therefore a combination of SEQ ID NO: 126 plus the SEQ ID NO: for each respective primer. Similarly, the sequences shown in Table 2 for the internal reverse MZA nested primers are a combination of SEQ ID NO: 127 plus the SEQ ID NO: for each respective primer. These combinations are indicated in the SEQ ID NO: column of Table 2. The annealing temperature for all the primers listed in Table 2 is 55° C. All markers set forth in Table 2 have shown polymorphism within a diverse panel of corn germplasm, including MP305 and the corn lines shown on Table 18.

The sequences of the ends of several of these BACs, as well as ESTs known to be located on these BACs, were used in order to identify new markers with which to further narrow the range in which the locus was located. The further markers used for this purpose are designated FLP8, FLP27, FLP33, FLP41, FLP56 and FLP95 in Table 1. In a manner similar to that described above, phenotype and genotypic correlations were made. It was determined that the locus was most likely located between FLP 8 and FLP 27 (See FIG. 3).

TABLE 1

Markers and primer pairs used in Examples 1, 4 and 5

| Used in Example | Name | Forward | SEQ ID NO: | Reverse | SEQ ID NO: |
|---|---|---|---|---|---|
| 1, 4 | FLP8 | CATGGAAGCCCCACAATAAC | 24 | ACATGGGTCCAAAGATCGAC | 23 |
| 1, 4 | FLP27 | AGCCCTATTTCCTGCTCCTG | 26 | GCATGCCCCATCTGGTATAG | 25 |
| 1, 4 | FLP33 | CTGTCGTTCGGTTTTGCTTC | 28 | GCATTCACATGTTCCTCACC | 27 |
| 1, 4 | FLP41 | TGTGTTCGCATCAAAGGTGT | 30 | CTGTAAGGCACCCGATGTTT | 29 |
| 1, 4 | FLP56 | GGTCTGGGAATGCTAAAGAGG | 32 | TGTCCAGGGTTACAGAAAACG | 31 |
| 1, 4 | FLP95 | ATTTCGACGGAGGGTTCTTC | 33 | GCAGCAGGAGGAGCTCATAG | 34 |
| 4 | FLP110 | ATGGAGGCTGCCCTGCTGAG | 35 | CGTATACCTCTCTGGCAAGGACGG | 36 |
| 4 | FLP111 | TTCCTGTTCGTCTGTATCTGATCCG | 37 | TTTGATTCCGGTCGAGTATAACCTG | 38 |
| 4 | FLP112 | GAAACTGCCTTCCCAGAAAACAATG | 39 | CAAGATCGGTGAAGTTGGTGCTTC | 40 |
| 4 | FLP113F | ATCACAGATGGGTCTCAAGGATTGC | 41 | | |
| 4 | FLPA1R | | | TTCCAAGCAATTCACAGCTC | 42 |
| 1, 5 | UMC1612 | AGGTCCAGGTTACAGAGCAAGAGA | 43 | GCTAGTAGGTGCATGGTGGTTTCT | 44 |
| 1, 4, 5 | UMC2041 | CTACACAAGCATAGAGGCCTGGAG | 45 | CAGTACGAGACGATGGAGGACAT | 46 |
| 1, 4 | CDO127 | TGCTGTTGTTACTCGGGTTG | 47 | CTCTGCCTCAGCACAAATTC | 48 |
| 1, 4, 5 | PHI093 | AGTGCGTCAGCTTCATCGCCTACAAG | 49 | AGGCCATGCATGCTTGCAACAATGGATACA | 50 |
| 1, 4 | CDO365 | CTTCCAGAGGCAAAGCGTAG | 51 | TGTCACCCATGATCCAGTTG | 52 |
| 1, 4, 5 | CSU166 | TATTGTGCACGTCACCTTGG | 53 | GGGCAGACTTACTGCTGGAG | 54 |
| 1, 4 | UMC2285 | ATCTGCCTCCTTTTCCTTGG | 55 | AAGTAGCTGGGCTTGGAGGG | 56 |
| 1, 4 | MZA11455 | ACGAAGCAATTTCACCTTCC | 57 | TGTGGAACTAACCCTCAGCATAG | 58 |
| 1 | MZA6064 | CGAGAACCGGAGAAGAAGG | 59 | TTGGGCTGCTGTATTTTGTG | 60 |
| 1, 4 | MZA15842 | GACGCAGCTGTGAAGTTGG | 61 | CACCGGAATACCTTGACCAC | 62 |
| 1, 5 | UMC1086 | CATGAAAGTTTTCCTGTGCAGATT | 63 | GGGCAACTTTAGAGGTCGATTTATT | 64 |
| 5 | UMC1466 | GATCCACTAGGGTTTCGGGGT | 65 | CGAATAGTGGTCTCGCGTCTATCT | 66 |
| 5 | UMC1418 | GAGCCAAGAGCCAGAGCAAAG | 67 | TCACACACACACTACACTCGCAAT | 68 |
| 5 | BNLG2162 | CACCGGCATTCGATATCTTT | 69 | GTCTGCTGCTAGTGGTGGTG | 70 |

TABLE 1-continued

Markers and primer pairs used in Examples 1, 4 and 5

| Used in Example | Name | Forward | SEQ ID NO: | Reverse | SEQ ID NO: |
|---|---|---|---|---|---|
| 5 | CSU166 | AAATATCGGCTTTGGTCACG | 71 | TCGTCCTTCCTCAATTCGAC | 72 |
| 5 | UMC1051 | AATGATCGAAATGCCATTATTTGT | 73 | CTGATCTGACTAAGGCCATCAAAC | 74 |
| 5 | UMC2187 | ACCCAACAAGTCTTAATCGGGTTT | 75 | GTCCACCCTACCTCTCAACAAACA | 76 |
| 5 | UMC1371 | CATGTGAATGGAAGTGTCCCTTT | 77 | GCATCCTTTTCGTTTCAAATATGC | 78 |
| 5 | UMC1856 | AGATCTGTTTTGCTTTGCTCTGCT | 79 | CATGCCTTTATTCTCACACAAACG | 80 |

TABLE 2

Nested MZA Primer Pairs Used in Example 1

| Name | Forward | SEQ ID NOs: | Reverse | SEQ ID NOs: |
|---|---|---|---|---|
| MZA1215 E | Agcccaattctgtagatccaa | 81 | Tgcatgcaccggatccttc | 82 |
| MZA1215 I | TGTAAAACGACGGCCAGTagcagcagacgatgcaaaga | 126 + 83 | GGAAACAGCTATGACCATGaggctggcggtggacttga | 127 + 84 |
| MZA1216 E | Ccggcctacggcaacaagaa | 85 | agggtacggtgacccgaag | 86 |
| MZA1216 I | TGTAAAACGACGGCCAGTttcgagacgctgtcgtacct | 126 + 87 | GGAAACAGCTATGACCATGacgacgcatggcactagcta | 127 + 88 |
| MZA3434 E | Tgtaccgcgagaactcca | 89 | ttgcattcacatgttcctcac | 90 |
| MZA3434 I | TGTAAAACGACGGCCAGTctactacgacggccgcta | 126 + 91 | GGAAACAGCTATGACCATGttgcagtagttttgtagcagg | 127 + 92 |
| MZA2591 E | Agtaaataacagcattgacctc | 93 | tccaacggcggtcactcc | 94 |
| MZA2591 I | TGTAAAACGACGGCCAGTctatataacagggccctggaa | 126 + 95 | GGAAACAGCTATGACCATGcacaaagcccacaagctaag | 127 + 96 |
| MZA11123 E | Accacaatctgaagcaagtag | 97 | cacagaaacatctggtgctg | 98 |
| MZA11123 I | TGTAAAACGACGGCCAGTaaagaccaagaaatgcagtcc | 126 + 99 | GGAAACAGCTATGACCATGagacatcacgtaacagtttcc | 127 + 100 |
| MZA15842 E | Ctcgattggcatacgcgata | 101 | ttccttctccacgcagttca | 102 |
| MZA15842 I | TGTAAAACGACGGCCAGTagaaggtatttgccatggctta | 126 + 103 | GGAAACAGCTATGACCATGgtttcacttgctgaaggcagtc | 127 + 104 |
| MZA11455 E | Gaccgatgaaggcaattgtga | 105 | accaaatagtcctagataatgg | 106 |
| MZA11455I I | TGTAAAACGACGGCCAGTttcaaccttctgactgacacat | 126 + 107 | GGAAACAGCTATGACCATGtaaacatagtcataaaaattac | 127 + 108 |
| MZA6064 E | Tcgaatgtatttttaatgcgg | 109 | atccacaatggcacttgggt | 110 |
| MZA6064 I | TGTAAAACGACGGCCAGTcagctattttgtcttcttcct | 126 + 111 | GGAAACAGCTATGACCATGggtcagattccaattcggac | 127 + 112 |
| MZA11394 E | Tcgtcctaacagcctgtgtt | 113 | gtccggatcaaatggatcgt | 114 |
| MZA11394 I | TGTAAAACGACGGCCAGTaacagcctgtgttgaataaggt | 126 + 115 | GGAAACAGCTATGACCATGcgtgttccgtcgagggagt | 127 + 116 |
| MZA8761 E | Ttctttgattctactcttgagc | 117 | cttcatggacgcctgagatt | 118 |
| MZA8761 I | TGTAAAACGACGGCCAGTtagagcttctgaactgatagc | 126 + 119 | GGAAACAGCTATGACCATGttggcatttagcttctctcca | 127 + 120 |

TABLE 2-continued

Nested MZA Primer Pairs Used in Example 1

| Name | Forward | SEQ ID NOs: | Reverse | SEQ ID NOs: |
|---|---|---|---|---|
| MZA1851 E | Atatattgcaccacttaaagcc | 121 | gggtgttatcacttgttctata | 122 |
| MZA1851 I | TGTAAAACGACGGCCAGT tggagtccttgaccatttgc | 126 + 123 | GGAAACAGCTATGACCATG tatatgcacttctagcgagtat | 127 + 124 |
| MZA16510 E | Aacaacaaggcgacggtgat | 127 | Tcatcttcgtcgtcctcatc | 130 |
| MZA16510 I | TGTAAAACGACGGCCAGT gatcatcctgccggagtt | 126 + 131 | GGAAACAGCTATGACCATG aaccgaaaacacaccctc | 127 + 132 |
| MZA1719 E | ccagcggtagattatatacag | 133 | cggtttggtctgatgaggc | 134 |
| MZA1719 I | TGTAAAACGACGGCCAGT ctcgggaaccttgttggga | 126 + 135 | GGAAACAGCTATGACCATG tgaaatccagaacctcctttg | 127 + 136 |

Example 2

Isolation of BAC Clones from the Resistant Lines and Identification of Candidate Genes in the Region of the Rcg1 Locus In order to isolate the gene responsible for the phenotype conferred by the Rcg1 locus, BACs containing the region between the FLP 8 and FLP 27 markers were isolated from a BAC library prepared from the resistant line DE811ASR (BC5). This library was prepared using standard techniques for the preparation of genomic DNA (Zhang et al. (1995) *Plant Journal* 7:175-184) followed by partial digestion with HindIII and ligation of size selected fragments into a modified form of the commercially available vector pCC1BAC™ (Epicentre, Madison, USA). After transformation into EPI300™ *E. coli* cells following the vendors instructions (Epicentre, Madison, USA), 125,184 recombinant clones were arrayed into 326 384-well microtiter dishes. These clones were then gridded onto nylon filters (HYBOND® N+, Amersham Biosciences, Piscataway, USA).

The library was probed with overlapping oligonucleotide probes (overgo probes; Ross et al. (1999) *Screening large-insert libraries by hybridization*, p. 5.6.1-5.6.52, In A. Boyl, ed. Current Protocols in Human Genetics. Wiley, New York) designed on the basis of sequences found in the BAC sequences shown in the previous example to be present between FLP8 and FLP27. BLAST™ search analyses were done to screen out repeated sequences and identify unique sequences for probe design. The position and interspacing of the probes along the contig was verified by PCR. For each probe two 24-mer oligos self-complementary over 8 bp were designed. Their annealing resulted in a 40 bp overgo, whose two 16 bp overhangs were filled in. The probes used in this way are presented in Table 4. Note that some of these probes were based on markers also used in Example 1 and Table 1, but the exact sequences are different as they were to be used as overgo probes rather than just PCR primers. Probes for hybridization were prepared as described (Ross et al. (1999) supra), and the filters prepared by the gridding of the BAC library were hybridized and washed as described by (Ross et al. (1999) supra). Phosphorimager analysis was used for detection of hybridization signals. Thereafter, the membranes were stripped of probes by placing them in a just-boiled solution of 0.1×SSC and 0.1% SDS and allowing them to cool to room temperature in the solution overnight.

BACs that gave a positive signal were isolated from the plates. Restriction mapping, PCR experiments with primers corresponding to the markers previously used and sequences obtained from the ends of each BAC were used to determine the order of the BACs covering the region of interest. Four BACs that spanned the entire region were selected for sequencing. These BACs were sequenced using standard shotgun sequencing techniques and the sequences assembled using the Phred/Phrap/Consed software package (Ewing et al. (1998) *Genome Research*, 8:175-185).

After assembly, the sequences thought to be in the region closest to the locus on the basis of the mapping data were annotated, meaning that possible gene-encoding regions and regions representing repetitive elements were deduced. Gene encoding (genic) regions were sought using the FGENESH™ software package (Softberry, Mount Kisco, N.Y., USA). FGENESH™ predicted a portion of a protein, that when compared using BLAST® (BLASTx/nr), displayed partial homology at the amino acid level to a portion of a rice protein that was annotated as encoding for a protein that confers disease resistance in rice. The portion of the maize sequence that displayed homology to this protein fell at the end of a contiguous stretch of BAC consensus sequence and appeared to be truncated. In order to obtain the full representation of the gene in the maize BAC, the rice amino acid sequence was used in a tBLASTn analysis against all other consensus sequences from the same maize BAC clone. This resulted in the identification of a consensus sequence representing the 3' end of the maize gene. However, the center portion of the gene was not represented in the sequences so obtained. PCR primers were designed based on the 5' and 3' regions of the putative gene and used in a PCR experiment with DNA from the original maize BAC as a template. The sequence of the resulting PCR product contained sequence bridging the 5' and 3' fragments previously isolated.

Figure 9B:
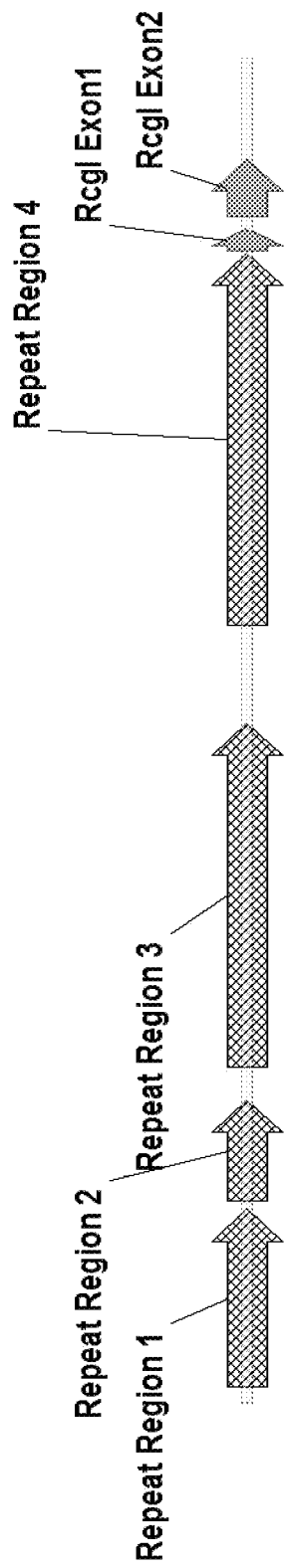
Figure 12:
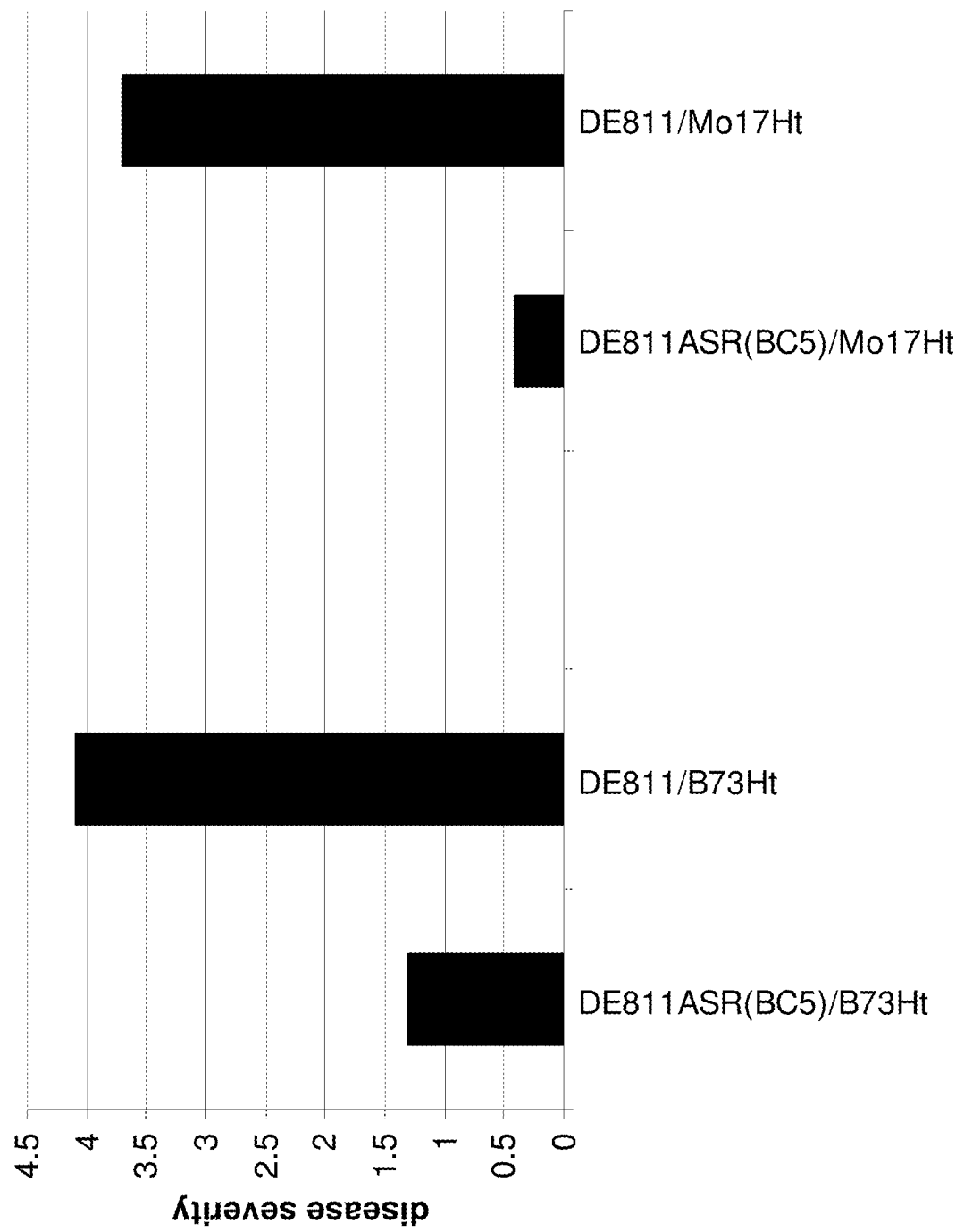
FIG. 12 shows the average severity of disease four to five weeks after inoculation with Cg in stalks of hybrids derived from crossing DE811ASR(BC5) and DE811 to the line indicated.
Figure 13:
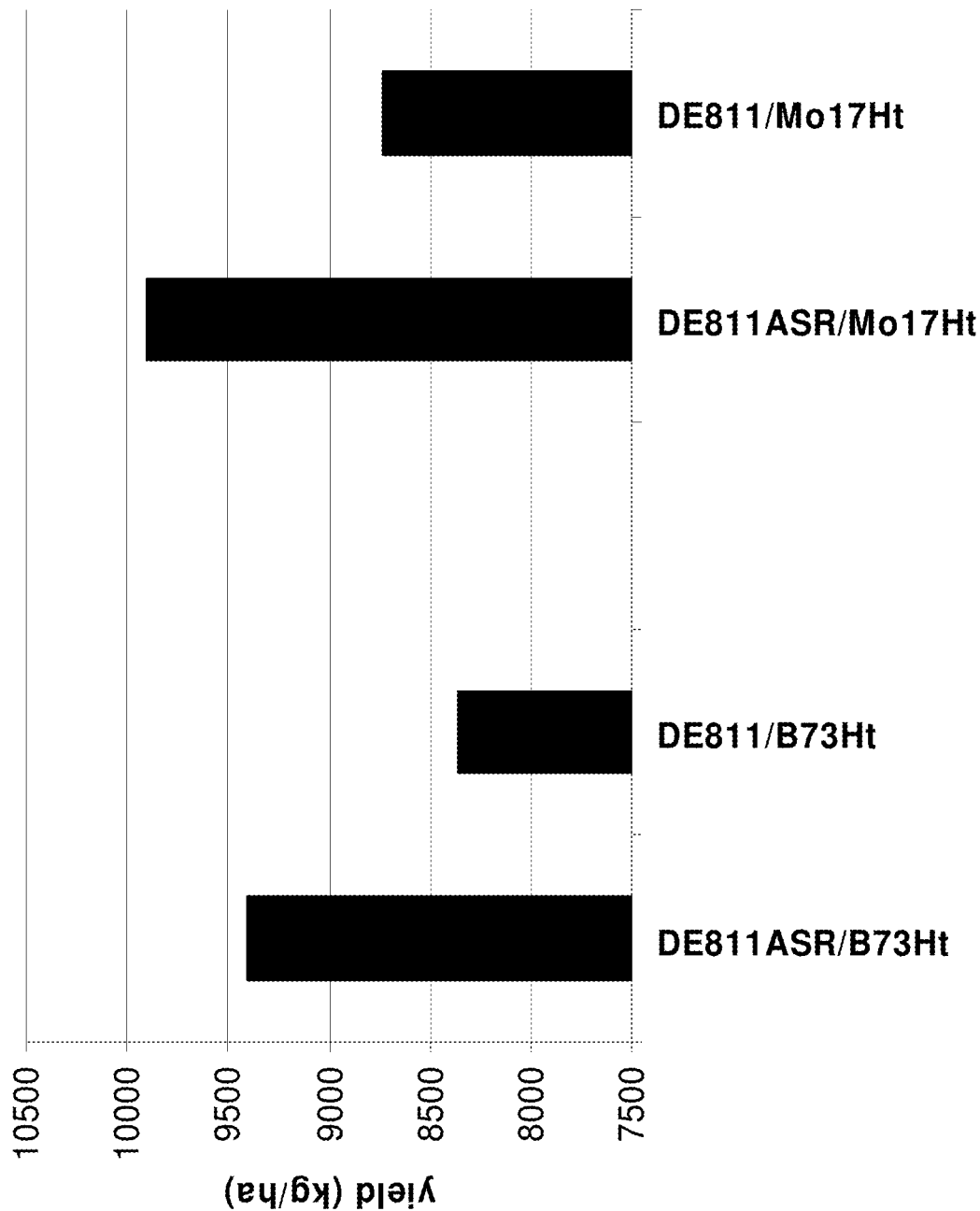
FIG. 13 shows the improvement in yield at maturity after inoculation with Cg in hybrids derived from crossing DE811ASR(BC5) to the line indicated when compared to the yield of hybrids derived from crossing DE811 to the line indicated.
Figure 14:
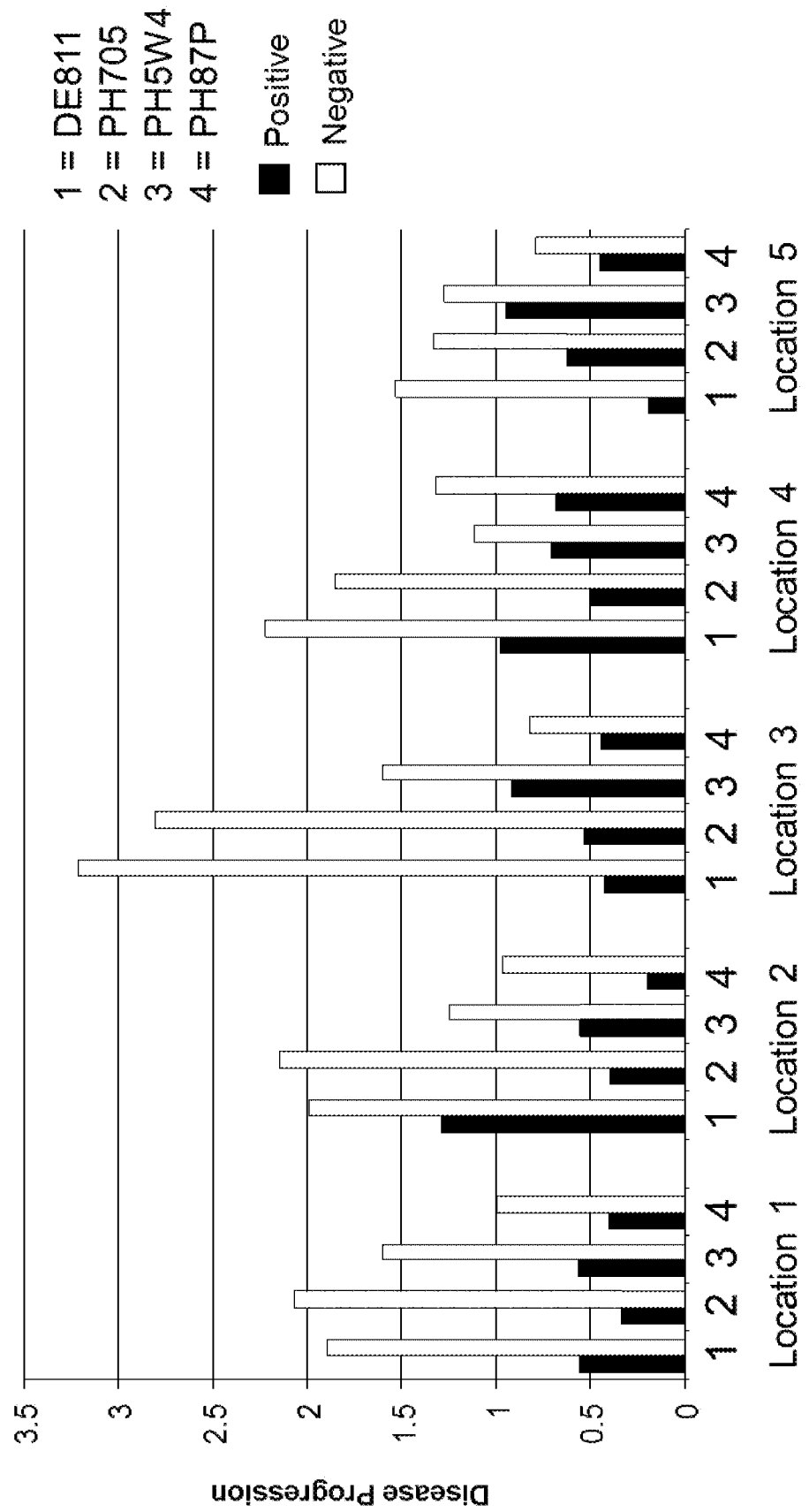
FIG. 14 shows the severity of disease at 5 different locations caused by Cg in stalks of inbred lines derived from DE811ASR(BC5) or MP305 four to five weeks after inoculation. Differences between the lines which were positive and negative for the Rcg1 gene are statistically significant at a P value of less than 0.05.
Figure 15:
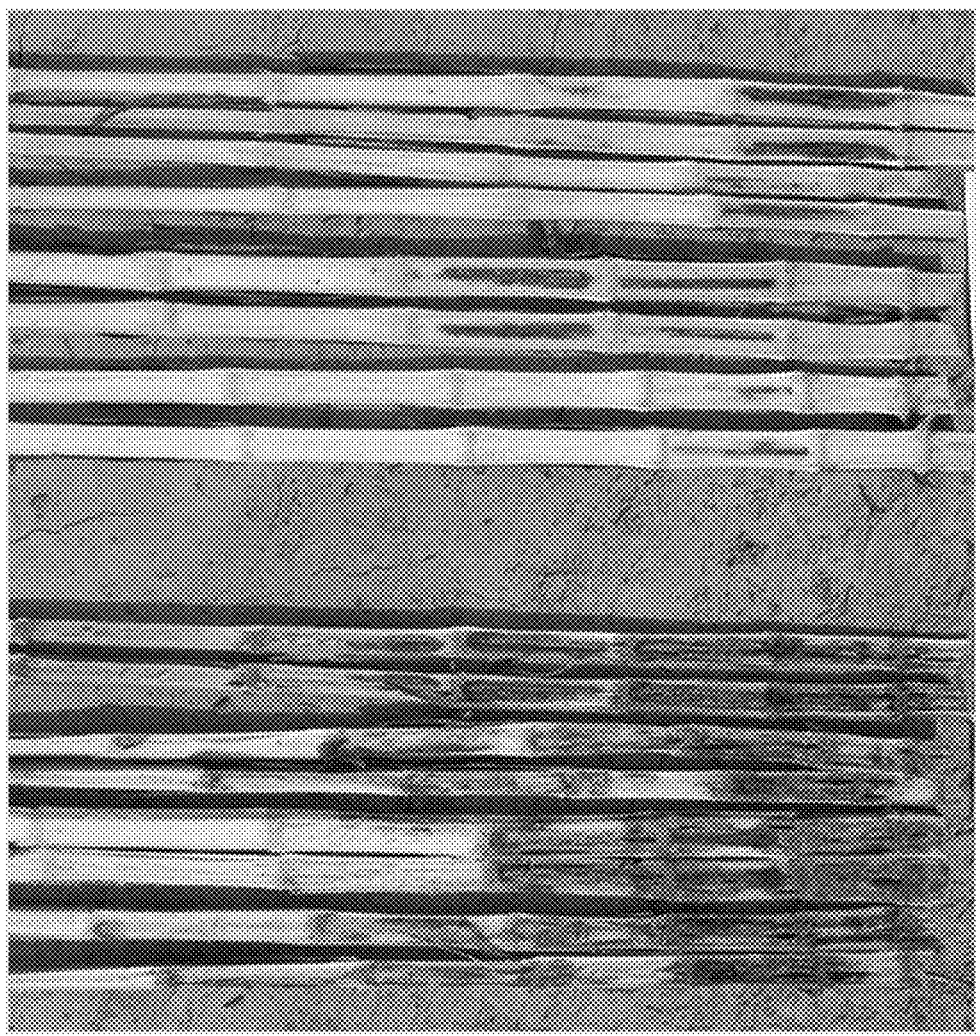
FIG. 15 shows disease progression in representative stalks from inbred PH705 lines which are positive and negative for Rcg1.
Figure 16:
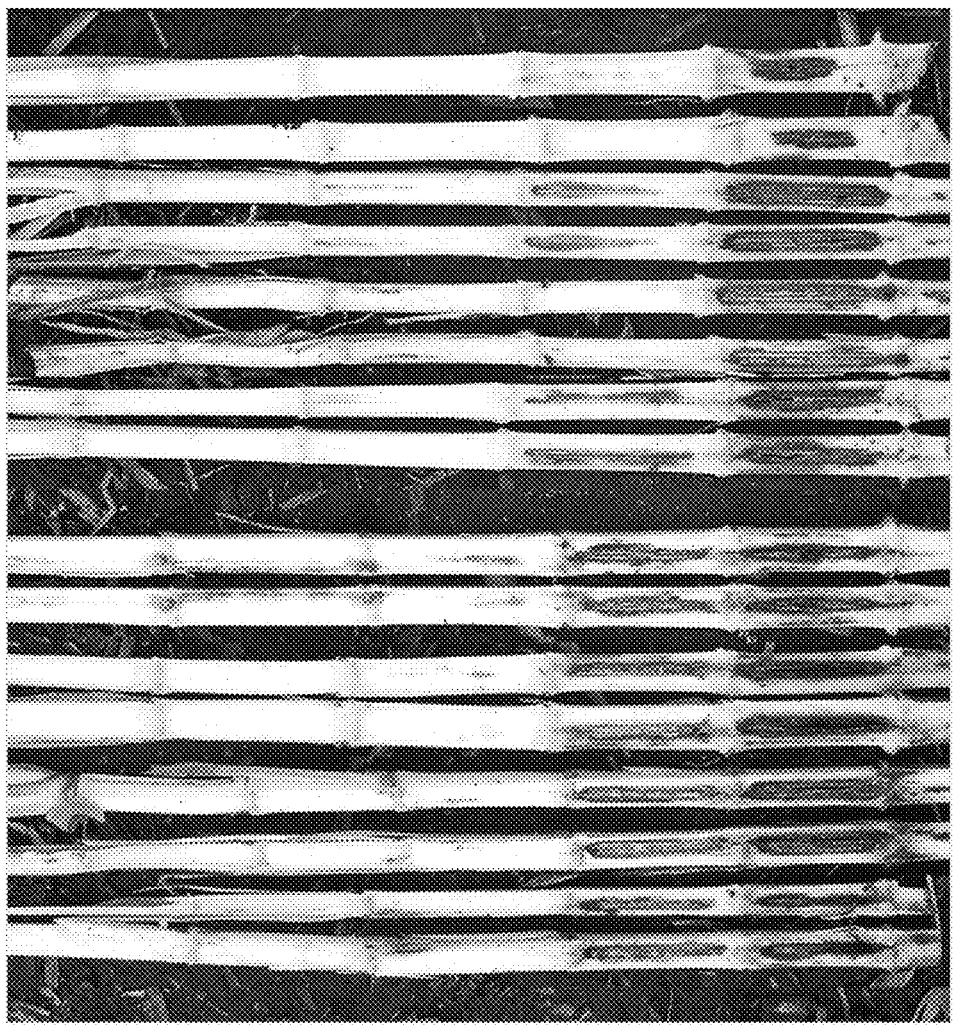
FIG. 16 shows disease progression in representative stalks from inbred PH87P lines which are positive and negative for Rcg1.

DE811ASR (BC5) has been deposited with the ATCC, and the methods described herein may be used to obtain a BAC clone comprising the Rcg1 locus. As shown in FIG. 9(*a*), the DE811ASR (BC5) chromosomal interval with the Rcg1 locus is non-colinear with the corresponding region of B73 and Mo17 (See FIGS. 9 and 22), as determined by the analysis of BAC libraries.

Figure 22:
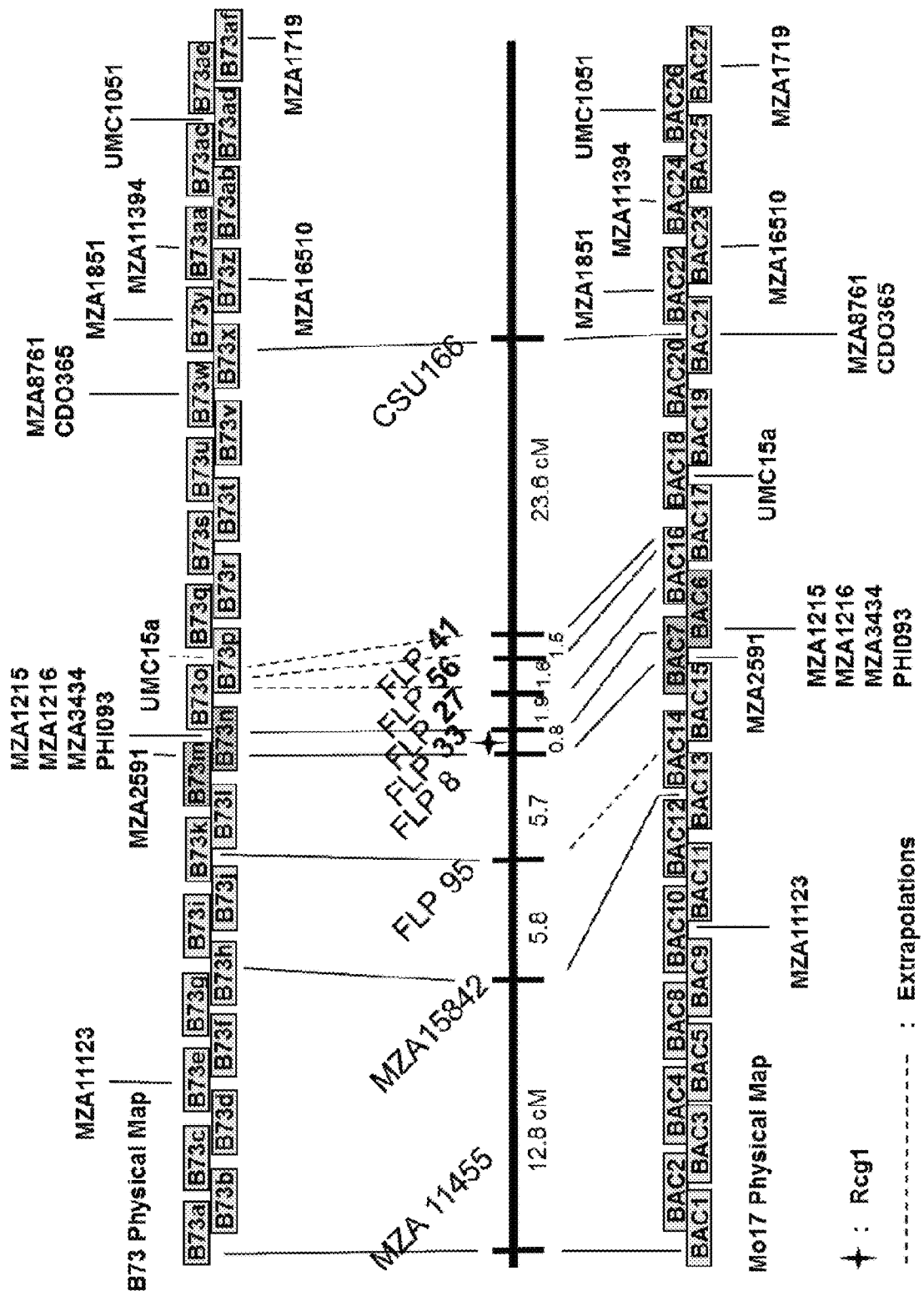
FIG. 22 shows the alignment of the genetic map containing MZA and public markers with the physical maps of Mo17 and B73. The genetic map distances were developed by using 1060 individuals from the BC7 mapping population. An analysis of a Mo17 BAC library also showed the Rcg1 locus to be non-colinear with the corresponding region of Mo17. The location of the markers shown by dotted lines to the B73 map are extrapolations from the Mo17 physical map location. The location of the markers shown by dotted lines to the Mo17 map are extrapolations from the B73 physical map location.

Using common sequence that hybridize to BACs in the Mo17 and the B73 BAC libraries, the corresponding BACs from both libraries were lined up in a tiling path as shown in FIG. 22. The B73 BACs in FIG. 22 were given shorter names for the purposes of the figure. Table 3, below, shows the BAC ID for each BAC designation indicated on FIG. 22. The public B73 BACs, c0113f01 and c0117e18 are directly north and south, respectively, of the Rcg1 locus indel region, with the deletion occurring in B73. Information about these two BACs can be viewed on several websites including the maize GDB website (maizegdb.org), the Gramene website (gramene.org) and the maize genome database of the Arizona Genomics Institute (genome.arizona.edu). The Arizona Genomics Institute website also provides the Maize Agarose FPC Map, version Jul. 19, 2005, which identifies BACs contiguous with c0113f01 and c0117e18. By searching on those databases, a multitude of BACs were identified that form a contig of the regions flanking the Rcg1 locus. Thus, the precise location of the Rcg1 locus and Rcg1 gene have now been identified on both the maize genetic and physical map. See FIGS. 7(a, b) and 22.

TABLE 3

BAC designations in FIG. 22, which were part of either the 187 contig (B73a through B73p) or 188 contig (B73q through B73af) of B73as shown on the Arizona Genomics Institute website mentioned above.

| B73 BAC designation in FIG. 22 | B73 BAC ID |
|---|---|
| B73a | c0100m06 |
| B73b | b0050k15 |
| B73c | c0127n01 |
| B73d | c0449o09 |
| B73e | c0046c06 |
| B73f | c0212g06 |
| B73g | c0153l14 |
| B73h | c0105c14 |
| B73i | b0502a04 |
| B73j | b0239l06 |
| B73k | b0171g07 |
| B73l | c0273k24 |
| B73m | c0113f01 |
| B73n | c0117e18 |
| B73o | c0119n15 |
| B73p | b0369n20 |
| B73q | b0031c17 |
| B73r | c0081g12 |
| B73s | c0303g03 |
| B73t | c0222i18 |
| B73u | c0428j12 |
| B73v | c0314e18 |
| B73w | c0150j16 |
| B73x | b0085n01 |

TABLE 3-continued

BAC designations in FIG. 22, which were part of either the 187 contig (B73a through B73p) or 188 contig (B73q through B73af) of B73as shown on the Arizona Genomics Institute website mentioned above.

| B73 BAC designation in FIG. 22 | B73 BAC ID |
|---|---|
| B73y | c0040c01 |
| B73z | c0018f13 |
| B73aa | c0091e23 |
| B73ab | b0100g11 |
| B73ac | c0177e03 |
| B73ad | b0264h08 |
| B73ae | c0410a17 |
| B73af | c0012f18 |

The complete sequence of the putative gene is set forth in SEQ ID NO: 1. The gene contains one intron, from nucleotide 950 to nucleotide 1452 of SEQ ID NO: 1. Reverse transcriptase-PCR using RNA prepared from DE811ASR (BC5) plants was used to determine the borders of the intron. The protein coding sequence of the gene is set forth in SEQ ID NO: 2, and the amino acid translation is set forth in SEQ ID NO 3. The predicted protein has a molecular weight of 110.76 kD.

The amino end from approximately amino acids 157 to 404 has homology to so-called nucleotide binding sites (NBS). There is a region with loose homology to LRR domains located approximately from amino acids 528 to 846. However, unlike previously studied NBS-LRR proteins, the leucine rich region lacks the systematic repetitive nature (Lxx) found in more classical LRR domains and in particular having no instances of the consensus sequences described by Wang et al. ((1999), *Plant J.* 19:55-64) or Bryan et al. ((2000), *Plant Cell* 12:2033-2045). The gene has loose homology with a family of rice genes and a barley gene as shown in FIG. 2 (a, b and c). Most of the homology is at the amino terminal end of the protein; the carboxyl end is quite distinct. This is demonstrated by the use of bold type, in FIG. 2 (a, b and c), which are amino acids identical to the gene of the embodiments, while those which are non-identical are not shown in bold type.

TABLE 4

Oligonucleotides annealed to synthesize overgo probes

| Associated Genetic marker | Forward oligo-nucleotide sequence | SEQ ID NO: | Reverse oligo-nucleotide sequence | SEQ ID NO: |
|---|---|---|---|---|
| FLP8 | cagggcctactt ggtttagtaata | 4 | gggtactacact agcctattacta | 5 |
| None | cggttacaaggt ctacccaatctg | 6 | gtcaaacagata gccgcagattgg | 7 |
| FLP33/ PHI93 | tacaaaactact gcaacgcctata | 8 | cctcaccccaag tatatataggcg | 9 |

TABLE 4-continued

Oligonucleotides annealed
to synthesize overgo probes

| Associated Genetic marker | Forward oligo-nucleotide sequence | SEQ ID NO: | Reverse oligo-nucleotide sequence | SEQ ID NO: |
|---|---|---|---|---|
| FLP27 | cattggacctct tccccactaaga | 10 | tccttgagtcca gtgctcttagtg | 11 |
| None | gaaactaggcgc gtcaggttttat | 12 | aaggcagccact gaaaataaaacc | 13 |

Example 3

Comparison of Genetic Structure in the Region of the Rcg1 Locus Between Resistant and Susceptible Lines and Expression Profiles of Candidate Genes Found in that Region Between Resistant and Susceptible Lines Having found a candidate gene in the region genetically defined to carry the locus responsible for the resistance to anthracnose phenotype, efforts were undertaken first to determine if there might be other genes present in the region and second to determine if the expression patterns of the candidate gene were consistent with its putative role. Fu and Dooner ((2002), Proc Natl Acad Sci 99:9573-9578) and Brunner et al. ((2005), Plant Cell 17:343-360) have demonstrated that different corn inbred lines may have significant rearrangements and lack of colinearity with respect to each other. Comparison of such genomes over larger regions can thus be complex. Such a comparison of the genomes of Mo17 (Missouri 17) and DE811ASR (BC5) revealed that in the region where the candidate gene is found in DE811ASR (BC5), a large insertion relative to Mo17 is present. Regions within and surrounding the insertion were sequenced and scanned for possible genes. A gene encoding a subunit of Ribulose bisphosphate carboxylase (Rubisco, a protein involved in carbon fixation after photosynthesis whose gene is present in multiple copies in the corn genome) was found in both the DE811ASR (BC5) and Mo17 genomes, just downstream of the position of the Rcg1 gene. A pseudogene (a gene rendered nonfunctional due to mutations disrupting the coding sequence) related to a vegetative storage protein was found, present only in the DE811ASR (BC5) genome some distance upstream of the Rcg1 gene. The only structurally intact gene likely to encode a protein with a function likely to be related to disease resistance was the Rcg1 gene isolated in the previous example. Other genes equally unlikely to be involved in disease resistance were located at a greater distance from the most likely position of the locus, as well as a large number of repetitive sequences.

In order to determine if and where the Rcg1 gene was transcribed, two techniques were used. First, the RNA profiles of resistant and susceptible plant materials were surveyed using Massively Parallel Signature Sequencing (MPSS™; Lynx Therapeutics, Berkeley, USA). Briefly, cDNA libraries were constructed and immobilized on microbeads as described (Brenner, S. et al. (2000) Nat. Biotechnol. 18(6): 630-634). The construction of the library on a solid support allows the library to be arrayed in a monolayer and thousands of clones to be subjected to nucleotide sequence analysis in parallel. The analysis results in a "signature" 17-mer sequence whose frequency of occurrence is proportional to the abundance of that transcript in the plant tissue. cDNA derived from RNA prepared from DE811ASR(BC5) and from DE811 (control line, susceptible to Cg) was subjected to MPSS™ analysis. Bioinformatic inspection of the resulting signatures showed that a signature sequence, referred to herein as Lynx19, (SEQ ID NO: 19) was present at 43 parts per million (ppm) in RNA samples from DE811ASR (BC5) uninfected stalks and at 65 ppm in infected, resistant stalks 9 days post inoculation (DPI) with Cg. This signature sequence was not detected in cDNA libraries of uninfected or Cg-infected stalks of the susceptible corn line DE811. An analysis of the sequence of Rcg1 indicates that the 17-mer tag is present at nucleotides 3945 to 3961 of SEQ ID NO: 1 in the putative 3' untranslated region of the gene.

Further proof that Rcg1 is exclusively expressed in corn lines that are derived from MP305 and resistant to anthracnose stalk rot was obtained by RT-PCR experiments. Total RNA was isolated from uninfected and Cg-infected stalks of resistant (DE811ASR1 (BC5)) and susceptible (DE811) corn lines using RNA STAT-60™ (Iso-Tex Diagnostics, Friendswood, Tex., USA). Total RNA (250 ng) from 0, 3, 6, 9, and 13 DPI resistant and susceptible samples was copied into cDNA and amplified using a GENEAMP® RNA-PCR kit (Applied Biosystems, Foster City, Calif., USA). The cDNA synthesis reaction was assembled according to the kit protocol using random hexamers as primers and incubated at 42° C. for 45 minutes. For PCR, KEB131 (SEQ ID NO: 20) and KEB138 (SEQ ID NO: 21), both designed from the putative 3' untranslated sequence of Rcg1, were used as the upstream and downstream primers, respectively. The cDNA was amplified for 30 cycles consisting of 1 minute at 94° C., 2 minutes at 50° C. and 3 minutes at 72° C. followed by a 7 minute extension at 72° C. As shown in FIG. 4, agarose gel electrophoresis of an aliquot of the RT-PCRs revealed the presence of a 260 bp band present in the samples derived from both infected and uninfected resistant plants but absent from susceptible samples. DNA sequence analysis confirmed that this fragment corresponded to nt 3625 to 3884 of the Rcg1 sequence consistent with the amplification product predicted from primers KEB131 and KEB138.

Example 4

Isolation of Lines Containing Mu Insertions in the Candidate Gene

One method to determine if a gene is responsible for a phenotype is to disrupt the gene genetically through the insertion of a transposition element (so-called transposon tagging) and then determine if the relevant phenotype of the plant is altered, in this case from resistant to Cg to susceptible to Cg. In corn this can be done using the mutator (Mu) element (Walbot, V. (1992) Annu. Rev. Plant Physiol. Plant Mol. Biol. 43:49-82). The basic strategy, outlined in FIG. 5, was to introduce active mutator elements into lines carrying the resistance gene, isolating plants homozygous for the resistance gene by assaying associated DNA markers as well as resistance to Cg by inoculation with Cg, then crossing those homozygous plants with a susceptible "tester" line. If the resistance gene is dominant, in principle all the resulting progeny would be resistant but heterozygous for the gene. However, if a Mu element inserted into the resistance gene in a way that disrupted its function, that individual would be susceptible to Cg. The disrupted gene can then be isolated and characterized.

MP305 was crossed with fifteen diverse mutator stocks (lines carrying active mutator elements). The resulting F1s were inter-mated (crossed with each other) in all possible combinations. To track the chromosomal region 4 L on which the resistance locus was known to reside (see Example 1) a variety of DNA markers known to be in the vicinity of the locus from the work described in Example 1 were selected and used on the Mu-tagged materials. About 1500 progeny plants from the inter-mating process were examined for resistance to Cg and for the presence of these markers. Analysis of the markers was done using either Southern blots (Botstein et al., (1980) *Am. J. Hum. Gen.* 32:314-331) for RFLP markers or by PCR for FLP markers as described in Example 1. Plants that were homozygous for all the markers tested and resistant to Cg were selected and test crossed with susceptible tester lines (A63, EH6WA and EF09B). About 16,000 test cross seeds generated from these homozygous and resistant plants were then planted and were used as female parents (meaning the pollen producing tassels were removed) and crossed with the susceptible tester lines used as males. All the female plants were screened for susceptibility to Cg. More than ten susceptible plants (putative knockout mutants) were identified. The open pollinated seed from each of these susceptible plants was harvested, along with eight resistant siblings as controls.

Figure 5:
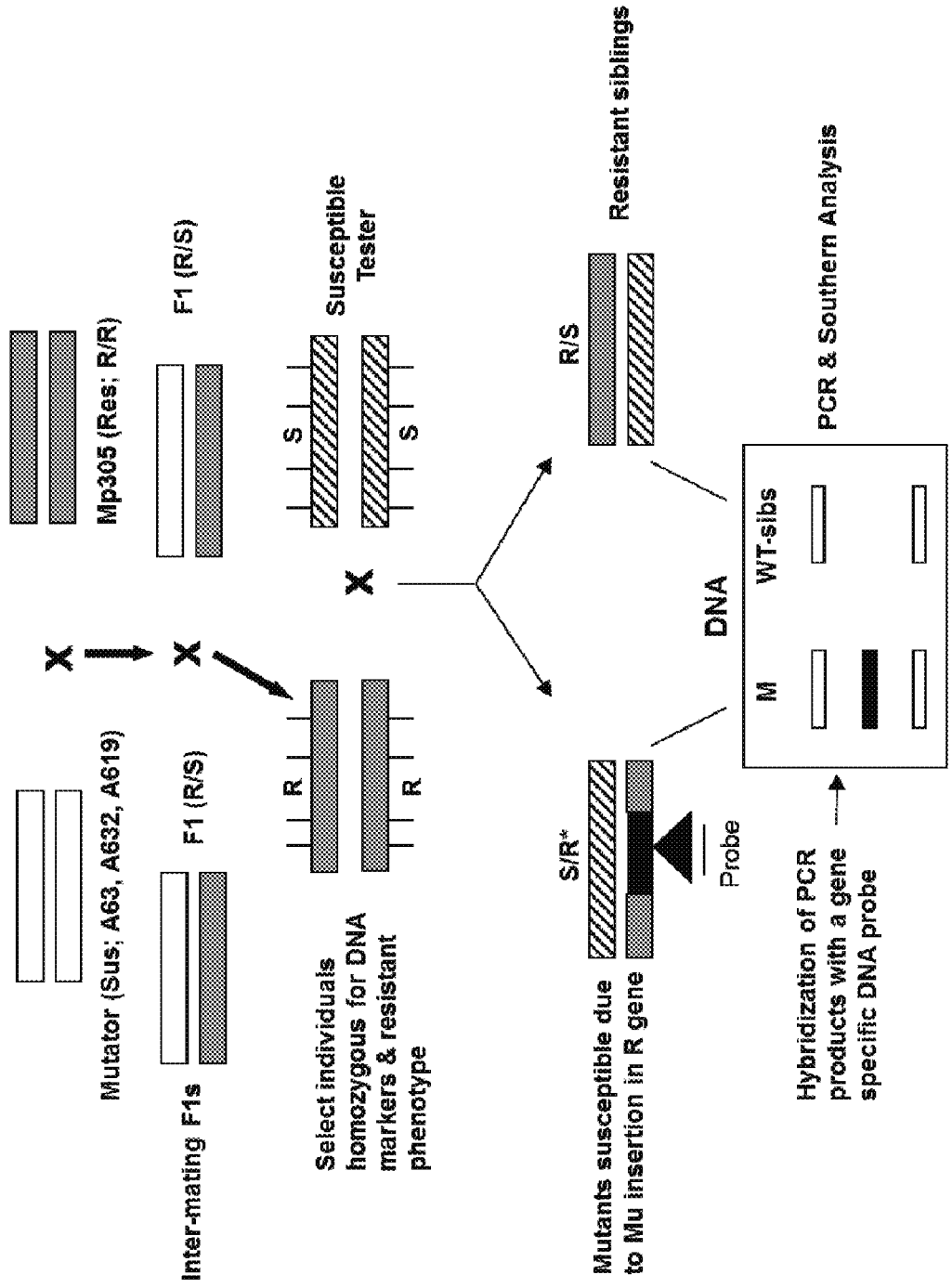
FIG. 5 is a schematic diagram of the Mu-tagging strategy used to validate the Rcg1 gene.
Figure 6:
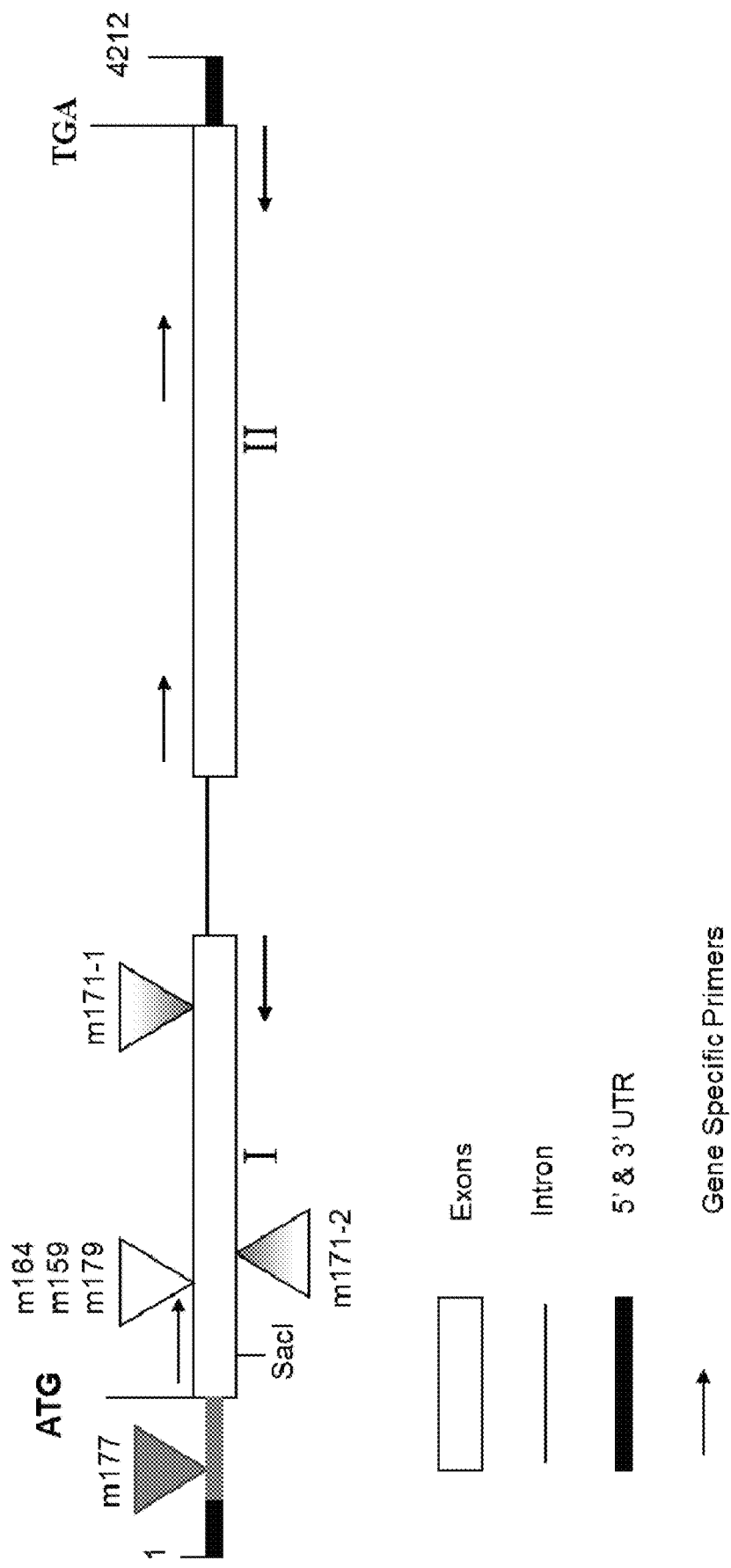
FIG. 6 is the gene structure of Rcg1 showing the location of four different mutator insertion sites.

DNA from a pool of 24 seedlings (grown in paper towels) from each of the putative knockouts and the control resistant siblings was extracted. This DNA was used as template for amplifying the flanking sequence from the site of Mu-insertion using gene-specific primers in combination with a consensus primer designed from the terminal inverted repeats (TIR) from the Mutator element sequence (SEQ ID NO: 125). In other words, PCR products would only be observed if a Mu element had inserted into the candidate gene isolated in Example 2. The primers FLP110F, FLP110R, FLP111F, FLP111R, FLP112F, FLP112R, FLP113F, and FLPA1R were used as the gene-specific primers (See Table 1). PCR amplified products were blotted onto nylon membranes and hybridized with a DNA probe from the candidate gene isolated in Example 2. PCR products that showed strong hybridization were excised from the gel, purified, cloned and sequenced. The resulting sequences were analyzed by aligning with sequences from the candidate gene and Mu-TIR. Mutator elements cause a direct 9 bp duplication at the site of insertion. Based on the flanking sequence information and a direct 9 bp duplication, four independent insertions were identified in exon 1 of the candidate gene (FIG. 5). One insertion (m177) was detected approximately 97 bp upstream of the initiation codon, in the 5' untranslated region of the gene. One common insertion event, 270 bp downstream of the initiation codon, was detected in three susceptible plants: m164, m159, and m179. The m171 susceptible plant was found to contain two Mu-insertions, 556 bp and 286 bp downstream of the initiation codon. When Southern blots were carried out using the exon1 region of the gene as a DNA probe, the modified hybridization pattern observed further confirmed these results.

This and the preceding examples may be summarized as follows. The earlier work cited in Example 1 showed that a previously observed locus conferring resistance to Cg was localized on the long arm of maize chromosome 4. The nature of this locus, its exact location or the gene(s) encoded by it were completely unknown. The work done in Example 1 demonstrates that the locus can be mapped to a very small region of the long arm of chromosome 4. Example 2 demonstrates that there is a gene to be found in this chromosomal region encoding a novel form of an NBS-LRR protein, a family of proteins known to be involved in resistance to pathogens but which vary widely in their sequence and specificity of resistance. Example 3 shows that this gene is present only in the resistant line, not the isogenic susceptible line, and that transcripts corresponding to this gene are found in the resistant line, indicating that the gene is expressed, and these transcripts are found only in the resistant line. Example 4 demonstrates that in four independently isolated Mu insertion events, when the gene is disrupted by insertion of a Mu element, the phenotype of these plants is changed from resistant to susceptible to Cg. Taken together, these data provide overwhelming evidence that the subject of the embodiments of this invention is a gene necessary in enhancing or conferring Cg resistance in corn plants.

Example 5

Backcrossing of the Rcg1 Locus into Susceptible Lines

An Rcg1 locus introgression of an inbred was made to confirm that the Rcg1 locus could be successfully backcrossed into inbreds, and that hybrids produced with the inbred line with the Rcg1 locus would have enhanced or conferred Cg resistance. DE811ASR (BC5) was also developed and used as an improved donor source for introgression of the Rcg1 locus. Next, several additional inbreds were utilized as recurrent parents in order to use the marker assisted breeding methods described herein to efficiently introgress the Rcg1 locus into a variety of inbred and hybrid genetic backgrounds, thereby enhancing or conferring resistance to Cg. Each of these examples are discussed in more detail below.

Proof of Concept (PH09B)

MP305 is a white kernel color inbred line with strong resistance to Cg, but its late flowering, poor yield and weak agronomic characteristics make it a poor donor parent in the absence of the use of the marker assisted breeding methods described herein. A molecular marker profile of MP305 is provided in Table 5b. Primers used for the SSRs reported in the table can be constructed from publicly available sequences found in the Maize GDB on the World Wide Web at maizegdb.org (sponsored by the USDA Agricultural Research Service), in Sharopova et al. (Plant Mol. Biol. 48(5-6):463-481), and/or in Lee et al. (Plant Mol. Biol. 48(5-6); 453-461). UMC15a is an RFLP marker, and the score reported is based on EcoR1 restriction.

To demonstrate the phenotypic value of the Rcg1 locus, the locus was first introgressed into line PH09B (U.S. Pat. No. 5,859,354) through to the BC3 stage as follows. The F1 population derived from the cross between MP305 and line PH09B was backcrossed once more to line PH09B, resulting in a BC1 population. Seedlings were planted out and backcrossed again to line PH09B to develop a BC2 population. DNA was prepared from leaf punches of BC2 families. To determine which BC2 families to plant for further backcrosses, genotyping was carried out on DNA from BC2 families using primers for markers flanking the region of interest, UMC2041, PHI093 and CSU166 (See Table 1). Seeds from BC2 families were planted and individual plants were genotyped again for the presence of the MP305 version of that region of the chromosome using the same three markers noted above. Positive plants were backcrossed to line PH09B once more to develop BC3 populations. Seed from these BC3 populations was planted and plants were selfed to obtain BC3S1 families segregating for the region of interest as well as BC3S1 families missing the region of interest. These families were used for phenotypic comparison (BC3S1 segregating versus BC3S1 without the region of interest).

In order to observe the performance of the Rcg1 gene in a heterozygous situation such as would be found in a commercial hybrid, appropriate testcrosses were made. Specifically, BC3S1 families segregating for the region of interest were planted and individual BC3S1 plants were genotyped. Plants homozygous for the Rcg1 gene as well as plants homozygous for the null allele (lacking the gene on both chromosomes) within each family were used to make testcrosses with inbreds PH2EJ (U.S. Pat. No. 6,333,453), PH2NO (U.S. Pat. No. 6,124,533), PH4CV (U.S. Pat. No. 6,897,363) and PH8CW (U.S. Pat. No. 6,784,349).

In the case of both the BC3S1 lines and the hybrids, the observed phenotypic differences indicated significant improvement for ASR resistance in lines and hybrids containing the region carrying Rcg1. The effect of the introgressed Rcg1 locus in the BC3S1 families and the derived testcross hybrids resulted in an improvement in terms of both the number of internodes infected and the number of internodes infected at more than 75%. The scores, using a visual scoring system commonly used by plant breeders, are shown in Table 5a below. The data clearly demonstrate that using crossing techniques to move the gene of the embodiments into other lines genetically competent to use the gene result in enhanced resistance to Cg.

TABLE 5a

Effect of the introgressed Rcg1 region on degree of resistance to anthracnose stalk rot in BC3S1 families and derived test crosses.

|  | Rcg1 | Number of internodes infected | Number of internodes > 75% infected |
|---|---|---|---|
| BC3S1 | Absent | 3.1 | 2.4 |
|  | Present | 2.3 | 1.5 |
|  | Difference | 0.8 | 0.9 |
| PH2EJ | Absent | 2.6 | 1.5 |
|  | Present | 2.1 | 0.9 |
|  | Difference | 0.5 | 0.6 |
| PH2NO | Absent | 3.0 | 2.1 |
|  | Present | 2.4 | 1.3 |
|  | Difference | 0.6 | 0.8 |
| PH4CV | Absent | 2.8 | 1.8 |
|  | Present | 2.2 | 1.0 |
|  | Difference | 0.6 | 0.8 |
| PH8CW | Absent | 2.9 | 1.7 |
|  | Present | 2.3 | 0.8 |
|  | Difference | 0.6 | 0.9 |

TABLE 5b

Molecular marker profile of MP305

| Marker Name | Base Pair Weight | Bin |
|---|---|---|
| phi295450 | 191.1 | 4.01 |
| phi213984 | 302.23 | 4.01 |
| phi096 | 235.07 | 4.04 |
| mmc0471 | 241.6 | 4.04 |
| umc1969 | 65.01 | 4.05 |
| umc1662 | 116.14 | 4.05 |
| umc2061 | 125.34 | 4.05 |
| phi079 | 185.76 | 4.05 |
| bnlg1937 | 235.87 | 4.05 |
| umc1382 | 153.7 | 4.05 |
| bnlg1217 | 194.36 | 4.05 |
| umc1390 | 133.46 | 4.05 |
| bnlg1265 | 221.83 | 4.05 |
| umc1303 | 127.2 | 4.05 |
| bnlg252 | 167.85 | 4.06 |
| umc1895 | 142 | 4.05 |
| umc1175 | 279.6 | 4.05 |
| umc1317 | 110.12 | 4.05 |
| umc1548 | 159.52 | 4.05 |
| umc1451 | 110.69 | 4.05 |
| umc1896 | 87.89 | 4.05 |
| umc1511 | 166.43 | 4.05 |
| umc1851 | 114.13 | 4.05 |
| umc1791 | 153.23 | 4.05 |
| bnlg1755 | 216.93 | 4.05 |
| umc1702 | 94.8 | 4.05 |
| umc1346 | 96.39 | 4.05 |
| umc1142 | 146.98 | 4.05 |
| mmc0371 | 230.82 | 4.06 |
| umc1945 | 113.52 | 4.06 |
| umc1093 | 222.7 | 4.06 |
| umc2027 | 111 | 4.06 |
| bnlg1621 | 184.11 | 4.06 |
| umc1299 | 144.46 | 4.06 |
| umc1869 | 154.39 | 4.06 |
| bnlg2291 | 201.5 | 4.06 |
| bnlg1784 | 237.23 | 4.07 |
| dupssr34 | 326.01 | 4.07 |
| umc1651 | 99.59 | 4.07 |
| umc2038 | 122.19 | 4.07 |
| umc1847 | 160.17 | 4.07 |
| umc1620 | 148.2 | 4.07 |
| umc1194 | 162.29 | 4.07 |
| umc1667 | 154.65 | 4.08 |
| phi438301 | 212.76 | 4.05 |
| umc1808 | 106.67 | 4.08 |
| umc1043 | 199.6 | 4.07 |
| umc1871 | 148.48 | 4.08 |
| dupssr28 | 100.64 | 4.08 |
| umc1466 | 110.91 | 4.08 |
| umc1418 | 153.12 | 4.08 |
| umc1899 | 111.81 | 4.08 |
| bnlg2162 | 144.98 | 4.08 |
| umc2041 | 165.17 | 4.08 |
| umc2285 | 156 | 4.08 |
| umc1086 | 95.57 | 4.08 |
| umc1612 | 108.54 | 4.08 |
| umc15a | approx 10 kb with EcoRI restriction | 4.08 |
| cdo365 | 411.5 | 4.08 |
| umc1051 | 125.9 | 4.08 |
| umc2187 | 84.94 | 4.08 |
| umc1371 | 120.6 | 4.08 |
| umc1132 | 132.14 | 4.08 |
| umc1856 | 156.88 | 4.08 |
| umc2153 | 131.97 | 4.08 |
| umc2200 | 151 | 4.08 |
| phi066 | 160 | 4.08 |
| umc1039 | 222.7 | 4.08 |
| umc2139 | 134.2 | 4.09 |
| umc1559 | 141.09 | 4.09 |
| umc1999 | 131.55 | 4.09 |
| umc1820 | 138.94 | 4.09 |
| umc1173 | 168.02 | 4.09 |
| umc1650 | 139.84 | 4.09 |
| umc1328 | 161.33 | 4.09 |
| umc1740 | 98.2 | 4.09 |
| umc1643 | 145.23 | 4.09 |
| umc1989 | 100.5 | 4.09 |
| umc1284 | 144.39 | 4.09 |
| umc1574 | 155.11 | 4.09 |
| umc2137 | 158.1 | 4.08 |
| umc1101 | 160.12 | 4.09 |
| umc2046 | 115.82 | 4.09 |

TABLE 5b-continued

Molecular marker profile of MP305

| Marker Name | Base Pair Weight | Bin |
| --- | --- | --- |
| phi314704 | 143.54 | 4.09 |
| bnlg1890 | 251.68 | 4.11 |
| phi076 | 158.05 | 4.11 |

DE811ASR(BC5) as Most Improved Donor for Use in Backcrossing

Figure 8A:
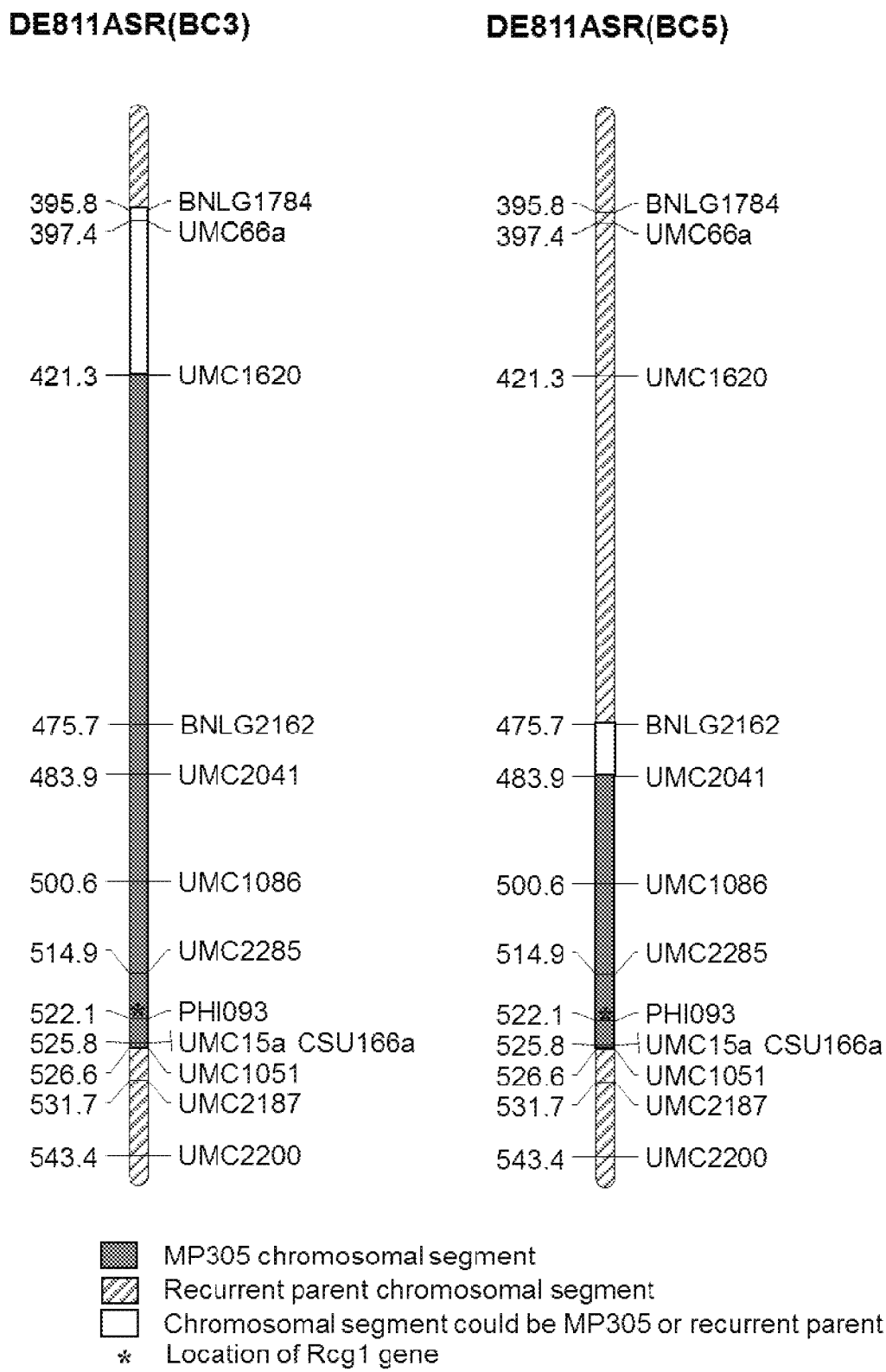
FIGS. 8a and 8b show a genetic map image showing the chromosomal interval with the Rcg1 locus in DE811ASR (BC3), the reduced size of the chromosomal interval with the Rcg1 locus obtained in DE811ASR (BC5) and the further reduced size of the chromosomal interval in inbreds obtained by initially using DE811ASR (BC5) as a donor source. For all markers, the map distances shown were reported on the IBM2 neighbors map publicly available on the Maize GDB, apart from for MZA15842, FLP27 and FLP56 for which map positions were extrapolated using regression analysis relative to the high resolution maps in FIG. 7(b), maps B and C, using the positions of UMC2285, PHI093 and CSU166a which were common to both maps.

Although MP305 was utilized in the above experiment, as is illustrated in FIG. 8(a), DE811ASR(BC5) retains a smaller MP305 chromosomal interval with the Rcg1 locus than DE811ASR(BC3) (and of course MP305 as well), and therefore is particularly useful as a donor source for the Rcg1 gene. The shortened chromosomal interval from the DE811ASR(BC5) source has been shown to be associated with an improved agronomic phenotype. Twenty two plants from the DE811ASR(BC3) derived line, 20 plants from the DE811ASR(BC5) derived line, five DE811 plants and five MP305 plants were grown in a greenhouse from November 2005 through March 2006 and data were taken for plant height and ear height; dates when 50% of the plants shed pollen (midshed); when 50% of the plants had visual ear shoots (midves) and when 50% of the plants had silks protruding from the earshoots (midslk); and kernel color was observed. On average, the DE811ASR(BC5) line was shorter than DE811ASR(BC3) (293 cm vs 345 cm) and the location of the ear was lower in the DE811ASR(BC5) than in the DE811ASR(BC3) (146 cm vs 183 cm), both of which are positive traits in terms of elite variety development. DE811ASR(BC5) was earlier for midshed, midves and midslk compared to DE811ASR(BC3). Midshed was approximately 1 day earlier, midves was approximately 6 days earlier and midslk was approximately 3 days earlier for DE811ASR(BC5) compared to DE811ASR(BC3). Kernels of DE811ASR(BC5) had a yellowish-brown (bronze) color whereas kernels of DE811ASR(BC3) had a pale yellow cap. Dates for midshed, midves and midslk were similar for DE811ASR(BC5) and DE811, whereas MP305 was approximately 11 days later for midshed and did not produce 50% visual ear shoots, nor 50% silks during the growing period. While these data are based on only a few plants for DE811 and MP305, and ears were not produced on those few lines, these greenhouse results resemble observations of these lines in the field. These data indicate that DE811ASR (BC5) resembles the DE811 recurrent parent much more closely than DE811ASR(BC3). Thus, DE811ASR(BC5) is an excellent initial donor source for the Rcg1 locus and the Rcg1 gene, both genotypically and phenotypically. In addition, DE811ASR(BC5) is particularly useful when introgressing the Rcg1 locus into germplasm with similar adaptation to DE811.

DE811 was developed by J. Hawk (Hawk, J. A. (1985). *Crop Science* Vol 25: p 716) and has been described as a yellow dent inbred line that originated from selfing and selection for six generations in a pedigree program out of a cross of B68 to an inbred derived from [B37 Htx (C103× Mp3204 double cross) sel]. DE811 silked 1 to 2 days later than B73 in tests in Delaware, but 4 days later than B73 at Missouri. Limited yield trials indicate that DE811 has satisfactory combining ability. It is a good silker (forms good silks, a component of the maize female flower important for fertility) and pollen shedder and can be crossed to earlier maturity germplasm for Northern US adaptation and to later maturity germplasm for Southern US adaptation. Thus, DE811ASR (BC5), in combination with the markers and breeding methods disclosed herein, is useful as an initial donor source for introgressing the Rcg1 gene into a wide variety of germplasm, including germplasm adapted to all of the regions in the US where Cg is present.

Creation of Inbred Rcg1 Locus Conversions

Following the tests for successful Rcg1 locus introgression in PH09B described above, additional Rcg1 locus conversions were carried out on other inbred lines. The first series had 5 backcrosses, with MP305 and DE811ASR (BC5) as donors. For the second series of backcrosses, molecular markers were used to reduce the chromosome interval in the BC5 conversions from the first series. These BC5 conversions were selected for crossovers below the Rcg1 gene. Those selected plants were then backcrossed to create the BC6 generation. Plants with crossovers above the gene were selected in the BC6 generation.

First Series of Backcrosses In the first series, DE811ASR (BC5) was used as the primary donor source, but parallel introgressions were also made to the same inbreds using MP305 as a donor source. These data, described in more detail below, show that while DE811ASR(BC5) is the preferred donor in many situations, MP305 can also be effectively used with the marker assisted breeding methods of the embodiments taught herein.

Elite inbred lines primarily adapted to North American growing conditions were selected for use as recurrent parents. The inbreds lines initially selected for use as recurrent parents were lines PHOR8 (U.S. Pat. No. 6,717,036), PH7CH (U.S. Pat. No. 6,730,835), PH705 (U.S. Pat. No. 6,903,250), PH5W4 (U.S. Pat. No. 6,717,040), PH51K (U.S. Pat. No. 6,881,881) and PH87P (U.S. Pat. No. 6,888, 051). Each of these lines was crossed with DE811ASR (BC5) as well as with MP305. The F1 generation derived from each of these crosses was backcrossed once more to the respective inbred line, resulting in a first backcross (the recurrent parent BC1) generation. Seedlings were planted out and DNA was prepared from leaf punches. PCR reactions were carried out using primers for markers flanking the region of interest; UMC1466, UMC1418, BNLG2162, UMC1086, UMC2041, UMC1612, CSU166, UMC1051, UMC2187, UMC1371, and UMC1856 were used in the early BC rounds (See Table 1) while in later BC rounds, UMC1418, BNLG2162, UMC1051, UMC2041, UMC2187, UMC1371 and UMC1856 were used. Seedlings whose PCR reactions gave a positive result (meaning that the MP305 derived Rcg1 locus was present) were then further backcrossed to the respective inbred lines to make a BC2. This procedure, called "genotyping", identifies the genetic composition of a plant at the site of a particular marker. These steps were repeated for the recurrent parent BC3, BC4 and BC5 development. Analysis shows that, after five backcrosses, these lines retained a significantly truncated chromosomal interval comprising the Rcg1 locus, and, based on visual observations, no indication of negative effects resulting from the presence of the Rcg1 locus was observed.

Recurrent parent selection was also carried out by selecting the plants most phenotypically like the recurrent parent. Using these genotypic and phenotypic methods, high quality conversions were selected with a high percentage of recurrent parent across the whole genome.

This example also illustrates that flanking markers are not used exclusively to select either for or away from the Rcg1 gene. Seedlings whose PCR reactions gave a positive result (meaning that the MP305 derived Rcg1 locus was present) were then further backcrossed to the respective inbred lines to make the final backcross (the recurrent parent BC5 generation) in this first series. Where the closest flanking polymorphic markers determined that the gene was present, the next set of double flanking polymorphic markers more distal to the gene were used for recurrent parent selection. Thus, the use of markers flanking the Rcg1 gene or Rcg1 locus serves to illuminate the recombination occurring in the region.

Second Series of Backcrossing

The inbred Rcg1 locus conversions made using the SSRs flanking the Rcg1 locus in the first series of backcrossing were then used as donors in a successive round of backcrossing. For this series of backcrossing, SNP markers were developed for the Rcg1 gene that enabled marker assisted selection in a high throughput manner, as described in Example 15, to select for the Rcg1 gene. SNP markers were also designed in the region around the Rcg1 locus, allowing flanking markers to be used to select away from the MP305 chromosomal interval surrounding the Rcg1 locus, and to select for the recurrent parent genotype, thereby greatly reducing linkage drag. It is only through physically mapping and cloning the gene that such precise marker-assisted recurrent parent selection is possible.

Figure 7B:
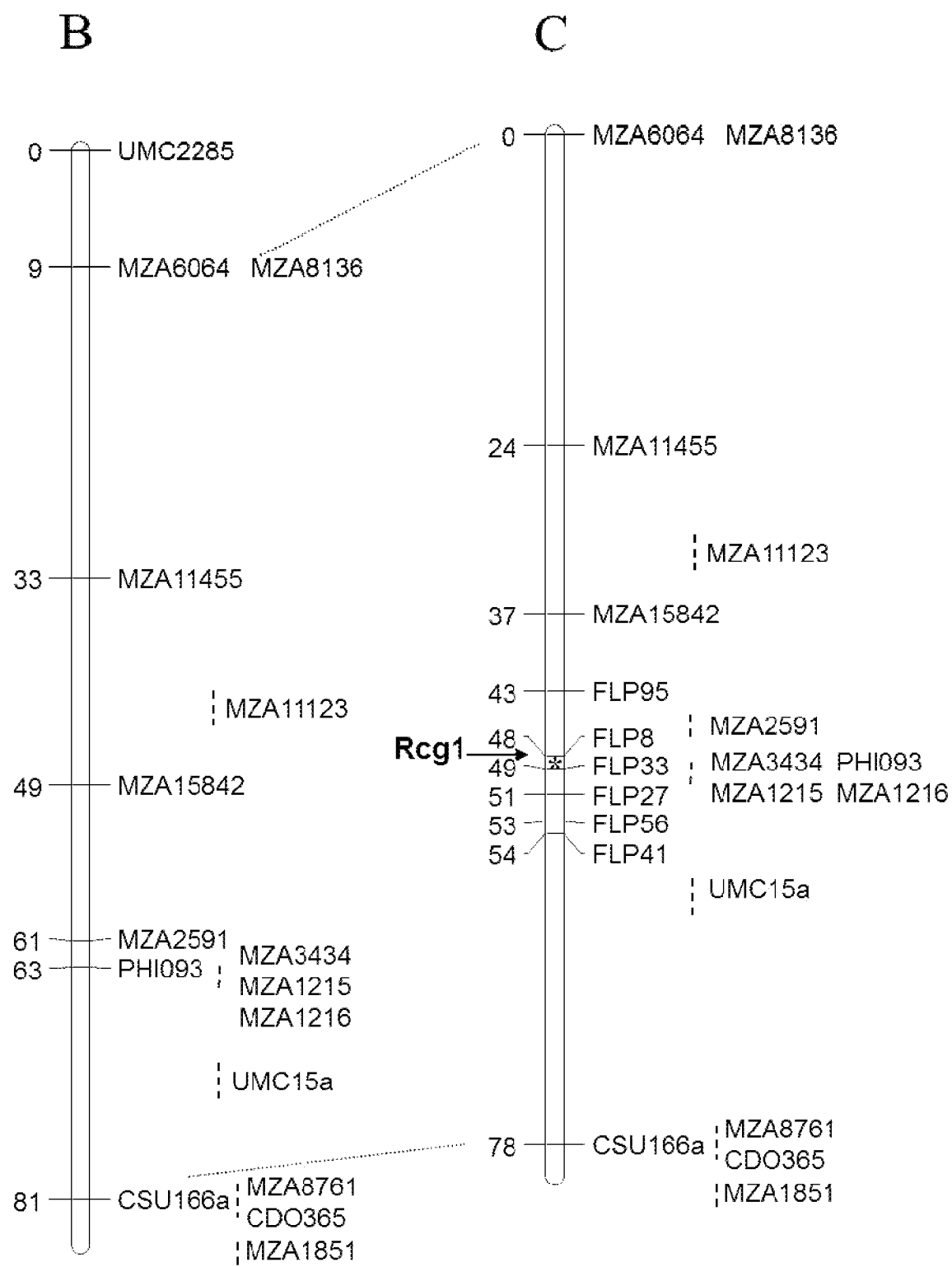
Figure 8B:
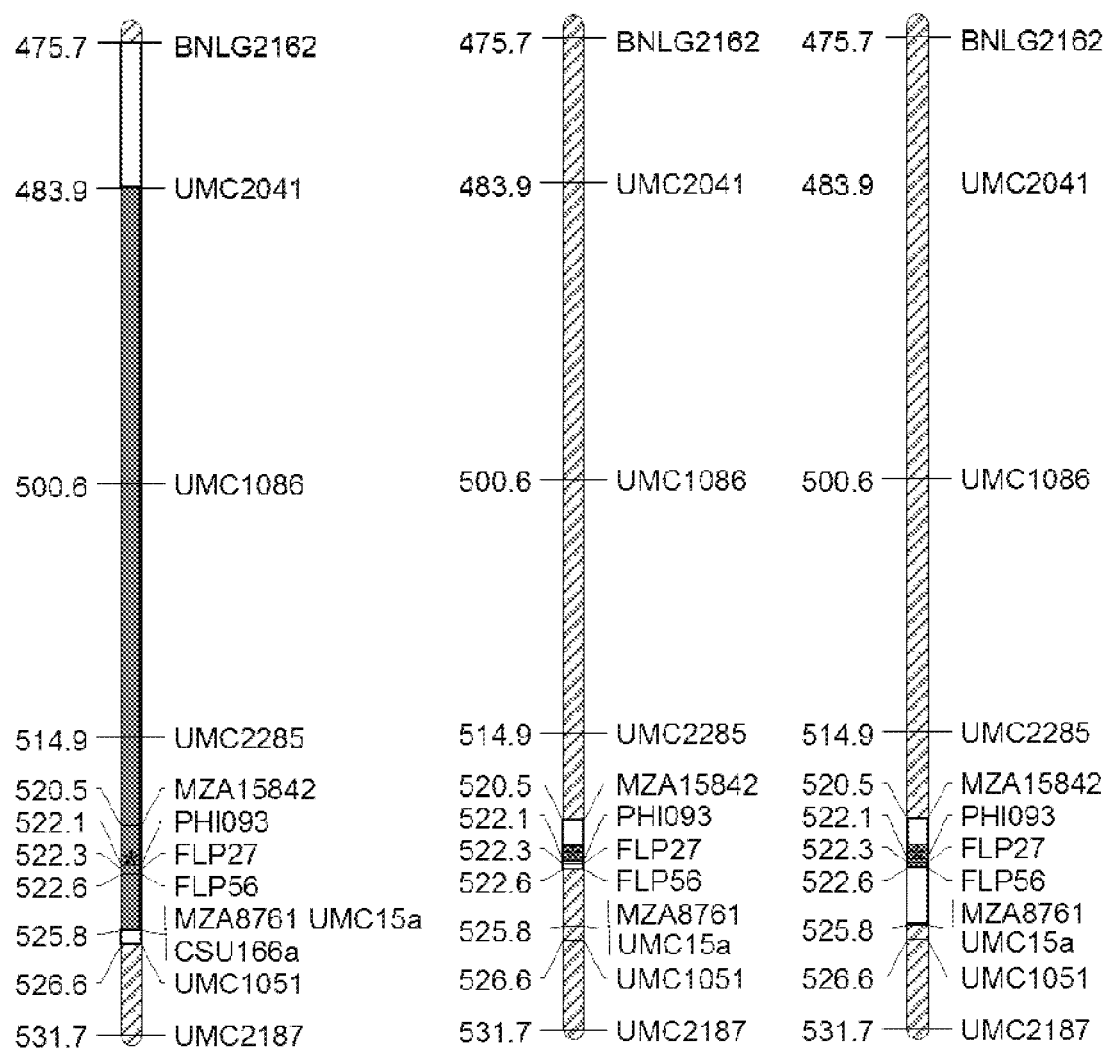

First, the recurrent parent BC5 plants resulting from the first series of backcrossing were re-screened with the more precise marker set, and recombination was selected for south of the Rcg1 gene. Flanking markers tightly linked to the Rcg1 gene (MZA8761, MZA1851, UMC1051, and UMC2187) were used to select for recurrent parent to the south of the gene in small population sizes of approximately 40 progeny. (See FIG. 8(a-b)). These progeny were then analyzed using the FLP markers disclosed herein, to more precisely determine the point of recombination. This data showed that some progeny were selected with recurrent parent genome less than 1 cM (based on IBM2 Neighbors genetic map distances) south of the Rcg1 gene, as shown in FIG. 8(b). Other progeny had recurrent parent genome less than 4 cM south of the Rcg1 gene. These marker-selected BC5 conversions were then used as donors, and crossed to near-isogenic counterparts of PH705, PH5W4, PH51K and PH87P as the recurrent parents to give a BC6 population. Markers in the Rcg1 gene were again used to select for Rcg1, with flanking markers to the north of Rcg1 this time being used to select for recurrent parent. In this round of selections, recombinations were detected in each population between Rcg1 and the marker MZA15842. The position of MZA15842 on the IBM2 Neighbors genetic map can be extrapolated from its position on the high resolution map shown in FIG. 7(b), map B, using regression relative to the flanking markers UMC2285 and PHI093. This placed MZA15842 at 520.5 cM on the IBM2 Neighbors genetic map. Therefore, as shown in FIG. 8(b), in two rounds of backcrossing, the donor genome was reduced to a segment of less than 6 cM in each population, or less than 0.8% of chromosome 4, based on the IBM2 Neighbors genetic map distances, and in some progeny the segment was less than 2.1 cM, or less than 0.25% of chromosome 4. For comparison, the MP305 chromosomal interval with the Rcg1 locus in DE811ASR (BC3) was 131 cM, or approximately 16% of chromosome 4, based on the IBM2 Neighbors genetic map distances. It is only through physically mapping and cloning the gene that such precise and efficient marker-assisted recurrent parent selection is possible.

Further Analysis

Figure 7A:
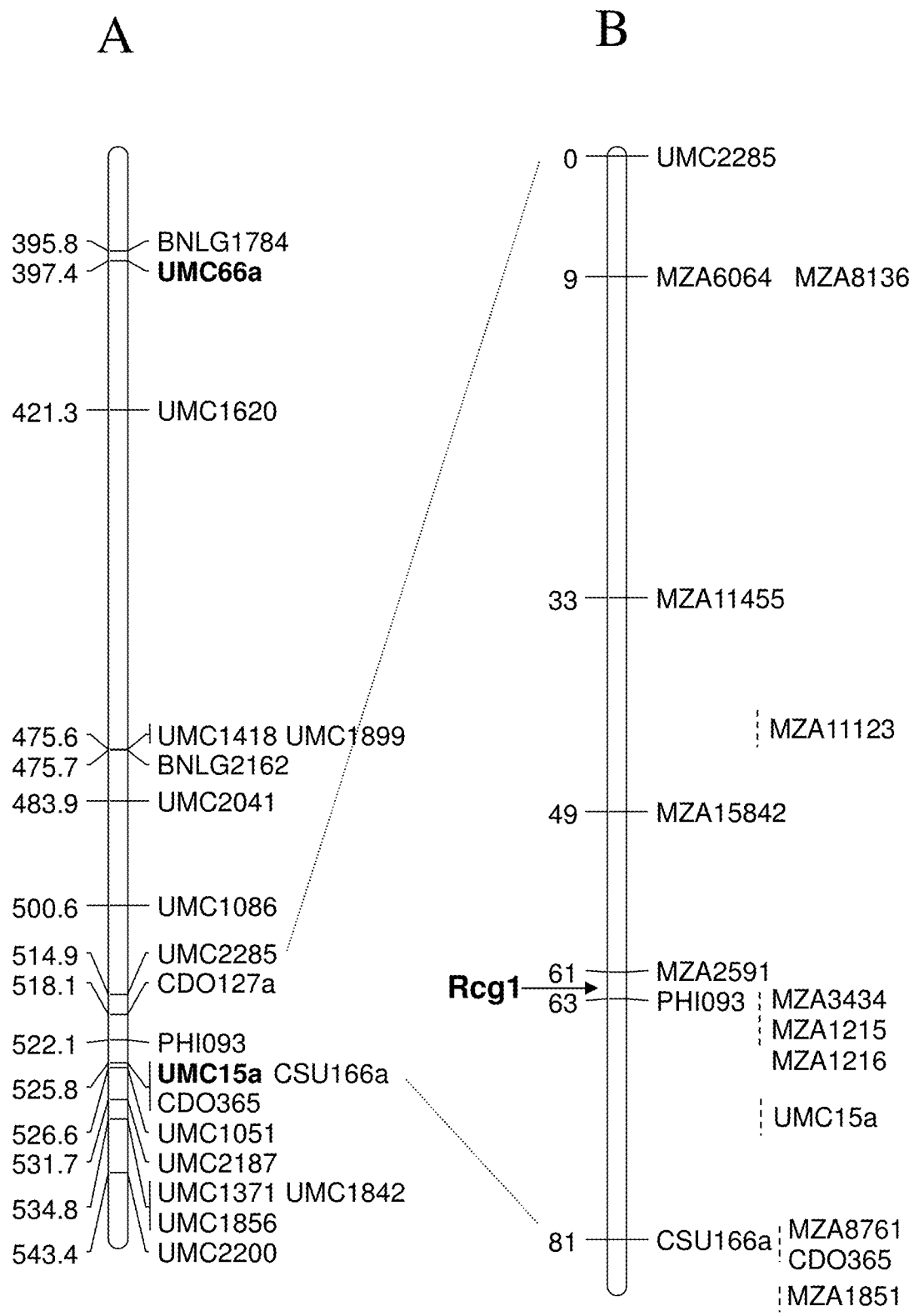
FIGS. 7a and 7b show a series of genetic map images with increasing resolution of the map of the region near the Rcg1 locus. Map distances for 7(a) for the map labelled "A" are in cM and in relation to the IBM2 Neighbors 4 genetic map. Map distances for 7(b) for the map labelled "B" were developed using 184 individuals from the BC7 population, and map distances for 7(b) for the map labelled "C" were developed using 1060 individuals from the BC7 population. Genetic mapping in the BC7 population increased the map resolution greater than 10-fold, when compared with the published map. The location of the markers shown to the right of each map is based on extrapolation of their location on the physical map.

Therefore, as a result of fine mapping the location of the Rcg1 gene, one may utilize any two flanking markers that are genetically linked with the Rcg1 gene to select for a small chromosomal region with crossovers both north and south of the Rcg1 gene. This has the benefit of reducing linkage drag, which can be a confounding factor when trying to introgress a specific gene from non-adapted germplasm, such as MP305, into elite germplasm, such as the inbred lines noted above. FIGS. 7 and 22, and Table 16 show many combinations of markers flanking the Rcg1 gene and locus that may be used for this purpose. Some specific flanking markers that may be used for selecting truncated chromosomal intervals that include the Rcg1 gene or locus are UMC2285 and UMC15a, UMC2285 and UMC2187, UMC1086 and UMC2200, UMC2041 and UMC2200, UMC2041 and PHI093, MZA11455 and UMC15a, MZA11455 and MZA3434, MZA15842 and MZA3434, and FLP8 and FLP33. Optionally, on or within each of these chromosomal intervals, one could utilize at least 1, 2, 3, 4, 5, 6, 7, 8, 9, 10, 11, 12, 13, 14, 15, 16 or more markers in order to locate the recombination event and select for the Rcg1 gene or Rcg1 locus with the maximum amount of recurrent parent genotype. Further, one may have at least 2, 3, 4, 5, 6, 7, 8, 9, 10, 11, 12, 13, 14, 15, or more markers between the north end of such chromosomal interval and the top of the Rcg1 gene and/or between the south end of such chromosomal interval and the bottom of the Rcg1 gene.

It is advantageous to have closely linked flanking markers for selection of a gene, and highly advantageous to have markers within the gene itself. This is an improvement over the use of a single marker or distant flanking markers, since with a single marker or with distant flanking markers the linkage associated with Rcg1 may be broken, and by selecting for such markers one is more likely to inadvertently select for plants without the Rcg1 gene. Since marker assisted selection is often used instead of phenotypic selection once the marker-trait association has been confirmed, the unfortunate result of such a mistake would be to select plants that are not resistant to Cg and to discard plants that are resistant to Cg. In this regard, markers within the Rcg1 gene are particularly useful, since they will, by definition, remain linked with resistance to Cg as enhanced or conferred by the gene. Further, markers within the Rcg1 locus are just as useful for a similar reason. Due to their very close proximity to the Rcg1 gene they are highly likely to remain linked with the Rcg1 gene. Once introgressed with the Rcg1 gene, such elite inbreds may be used both for hybrid seed production and as a donor source for further introgression of the Rcg1 gene into other inbred lines.

Thus, the data clearly shows that inbred progeny converted by using DE811ASR(BC5) as a donor source retain the truncated MP305 chromosomal interval. The inbreds comprising the truncated MP305 chromosomal interval are very useful as donor sources themselves, and there is no need to revert to DE811ASR(BC5) as a donor source. By using marker assisted breeding as described herein, the truncated MP305 chromosomal interval can be further reduced in size as necessary without concern for losing the linkage between the markers and the Rcg1 gene. Phenotypically, a reduced chromosomal interval is associated with improved agronomic performance, as was demonstrated for DE811ASR(BC5) versus DE811ASR(BC3) described above.

Example 6

Constructs for the Transgenic Expression of Rcg1

The Rcg1 gene was expressed as a transgene to determine if this gene alone was sufficient, as well as necessary, for the phenotype conferred by the Rcg1 locus. This was done using two different constructs, differing chiefly in the promoter used.

Example 6a

In this example, the Rcg1 gene was expressed using its own promoter. The upstream region of the Rcg1 gene was sequenced using the same BACs that in Example 2 provided the sequences of the protein-coding section of the gene. The sequence of 1684 bp 5' to the ATG is set forth in SEQ ID NO: 24.

In order to transform the complete Rcg1 gene, including the promoter and protein encoding region, a 5910 bp fragment extending from position 41268 through position 47176 in SEQ ID NO: 137 was amplified by PCR using a BAC clone as template DNA. To enable cloning using the GATEWAY® cloning system (Invitrogen, Carlsbad, USA), attB sites were incorporated into the PCR primers, and the amplified product was cloned into pDONR221 vector by GATEWAY® BP recombination reaction. The resulting fragment, flanked by attL sites, was moved by the GATEWAY® LR recombination reaction into a binary vector. The construct DNA was then used for corn transformation as described in Example 7.

Example 6b

In order to express the Rcg1 gene throughout the plant at a high level, the coding region of the gene and its terminator were placed behind the promoter, 5' untranslated region and an intron of a maize ubiquitin gene (Christensen et al. (1989) *Plant Mol. Biol.* 12:619-632; Christensen et al. (1992) *Plant Mol. Biol.* 18:675-689). One of skill in the art would be able to select a different promoter to express the Rcg1 gene based on the desired expression pattern. To enable cloning using the GATEWAY® cloning system, attB sites were incorporated into PCR primers that were used to amplify the Rcg1 gene starting at 142 bp upstream of the initiation codon and terminating 624 bp downstream of the stop codon. The amplified product was cloned into pDONR221 (Invitrogen, Carlsbad, USA) using a GATEWAY® BP recombination reaction. After cloning, the resulting Rcg1 gene was flanked by attL sites. In the final step, the Rcg1 clone was moved by GATEWAY® LR recombination reaction into a vector which contained the maize ubiquitin promoter, 5' untranslated region and first intron of the ubiquitin gene as described by Christensen et al. (supra) followed by GATEWAY® ATTR1 and R2 sites for insertion of the Rcg1 gene, behind the ubiquitin expression cassette. The vector also contained a marker gene suitable for corn transformation, so the resulting plasmid, carrying the chimeric gene (maize ubiquitin promoter-ubiquitin 5' untranslated region-ubiquitin intron 1-Rcg1), was suitable for corn transformation as described in Example 7.

Example 7

*Agrobacterium*-Mediated Transformation of Maize and Regeneration of Transgenic Plants The recombinant DNA constructs prepared in Example 6a and 6b were used to prepare transgenic maize plants as follows.

Maize was transformed with selected polynucleotide constructs described in Example 6a and 6b using the method of Zhao (U.S. Pat. No. 5,981,840, and PCT patent publication WO98/32326). Briefly, immature embryos were isolated from maize and the embryos contacted with a suspension of *Agrobacterium*, where the bacteria were capable of transferring the polynucleotide construct to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent, and growing transformed callus was recovered (step 4: the selection step). The callus was then regenerated into plants (step 5: the regeneration step), and calli grown on selective medium were cultured on solid medium to regenerate the plants.

Example 8: The Rcg1 Gene is Necessary but not Sufficient to Confer the Phenotype Associated with the Rcg1 Locus Transgenic plants were made as described in Example 7 using the constructs described in Examples 6a and 6b, respectively. For both the native Rcg1 gene and the ubiquitin Rcg1 gene constructs, 30 independent events and 10 control events transformed with the binary vector only, lacking the constructs of Example 6a or 6b, were generated.

Leaf discs of each native gene transgenic event were harvested for total RNA isolation. RT-PCR was performed using the gene specific primers FLP111F and FLP111R set forth in SEQ ID NOS: 37 and 38. In 29 out of 30 transgenic events, the expected 637 bp RT-PCR band was present indicating expression of the native gene construct. Disease assays were performed in the greenhouse on the same 30 native Rcg1 transgenic events to determine if the plants were resistant to Cg. To accomplish this, leaf blight assays were first carried out on 5 sibling plants of each event using the procedures described in Example 12. A single event was found to show a statistically significant reduction in disease score relative to control plants lacking the native Rcg1 gene construct. Plants that had been subjected to the leaf blight assay were allowed to develop two weeks post anthesis and were then further tested by Cg inoculation into the first elongated stalk internode. These stalk infection assays showed a single transgenic event expressing the native Rcg1 transgene to be more resistant to infection by Cg when compared to control plants. However, this event differed from the positive event identified via the leaf infection assays.

Plants transformed with the ubiquitin Rcg1 construct described in Example 6b were analyzed in a similar fashion. RT-PCR analysis showed that 27 out of 30 transgenic events contained the expected 637 bp band, indicating expression of the ubiquitin Rcg1 construct. When leaf infection assays were performed on 5 plants from each of the 30 events, a single event was identified that showed a statistically significant reduction in disease compared to control plants. The transgenic plants were further analyzed by stalk infection assays. Two events were found to exhibit increased resistance to stalk rot when compared to control plants lacking the ubiquitin Rcg1 gene. These transgenic events did not include the former positive event identified in the leaf blight assays. One ubiquitin Rcg1 event showed a statistically significant increase in susceptibility to anthracnose stalk rot relative to control plants.

The results of these experiments suggest a lack of efficacy with either the native or ubiquitin Rcg1 construct in leaf blight or stalk infection assays. Although by RT-PCR, each construct was found to be expressed at levels comparable to or greater than the level of Rcg1 found in DE811ASR(BC5), only a limited number of events were found to show a statistically significant improvement in disease score relative to control plants: 2 native Rcg1 T0 events and 2 ubiquitin Rcg1 T0 events. These events were separately identified by the leaf blight and stalk infection assays. However, positive events showing increased disease resistance by the leaf blight assay failed to correlate with those identified by the stalk infection assay. This is in contrast to the DE811ASR(BC5) positive control which shows a clear increase in resistance relative to DE811 in both leaf blight and stalk infection assays. In addition, no correlation was observed between measured disease scores and level of transgene expression. Indeed, one of the positive ubiquitin Rcg1 events failed to produce a detectable RT-PCR band upon reverse transcription of total RNA and amplification of cDNA with FLP111F and FLP111R. The lack of correlation between the different assays for the very small number of events that appeared to show resistance, the much larger number of events that showed no resistance and the very different results obtained with DE811(BC5) led to the hypothesis that while the Rcg1 gene is necessary for the phenotype conferred by the Rcg1 locus, it alone is not sufficient. The small amount of apparent resistance observed is due to normal experimental variation.

In order to test the hypothesis noted above and to exclude the possibility that errors inherent in the Rcg1 coding region of both constructs give rise to production of a non-functional protein that is not competent in resistance expression, an experiment was designed that tested the ability of the transgenes to complement a transposon knockout in Rcg1. The insertion line m164, identified in the MP305 Mu-tagged population and described in Example 4, contains a transposable element in Exon 1 of the Rcg1 gene and exhibits an anthracnose-susceptible phenotype upon infection with Cg. This line therefore has all the components of the Rcg1 locus, but the Rcg1 gene is not functional due to the transposon insertion. Two native and two ubiquitin Rcg1 T1 lines (i.e., two each of the lines carrying the constructs of Example 6a and 6b respectively) were crossed with the Rcg1 mutant line m164. Progeny from that cross were screened by leaf painting with glufosinate to identify those plants containing the selectable marker gene that co-segregates with the Rcg1 transgenes. Plants carrying the Mu-tagged Rcg1 gene were identified by PCR analysis of extracted DNA using an Rcg1 gene specific primer defined in SEQ ID NO: 259 and the Mu-TIR primer of SEQ ID NO: 233. Leaf sheaths of V7-9 plants were inoculated with 5 µl of a 5×10$^6$/mL suspension of C. graminicola conidia following wounding of tissue. Inoculated leaf sheaths were sealed in plastic wrap for 5 days to retain high moisture levels. At that time, the uppermost infected sheath was excised for quantitation of lesion size by LemnaTec (LemnaTec, Würselen, Germany) image analysis.

Figure 27:
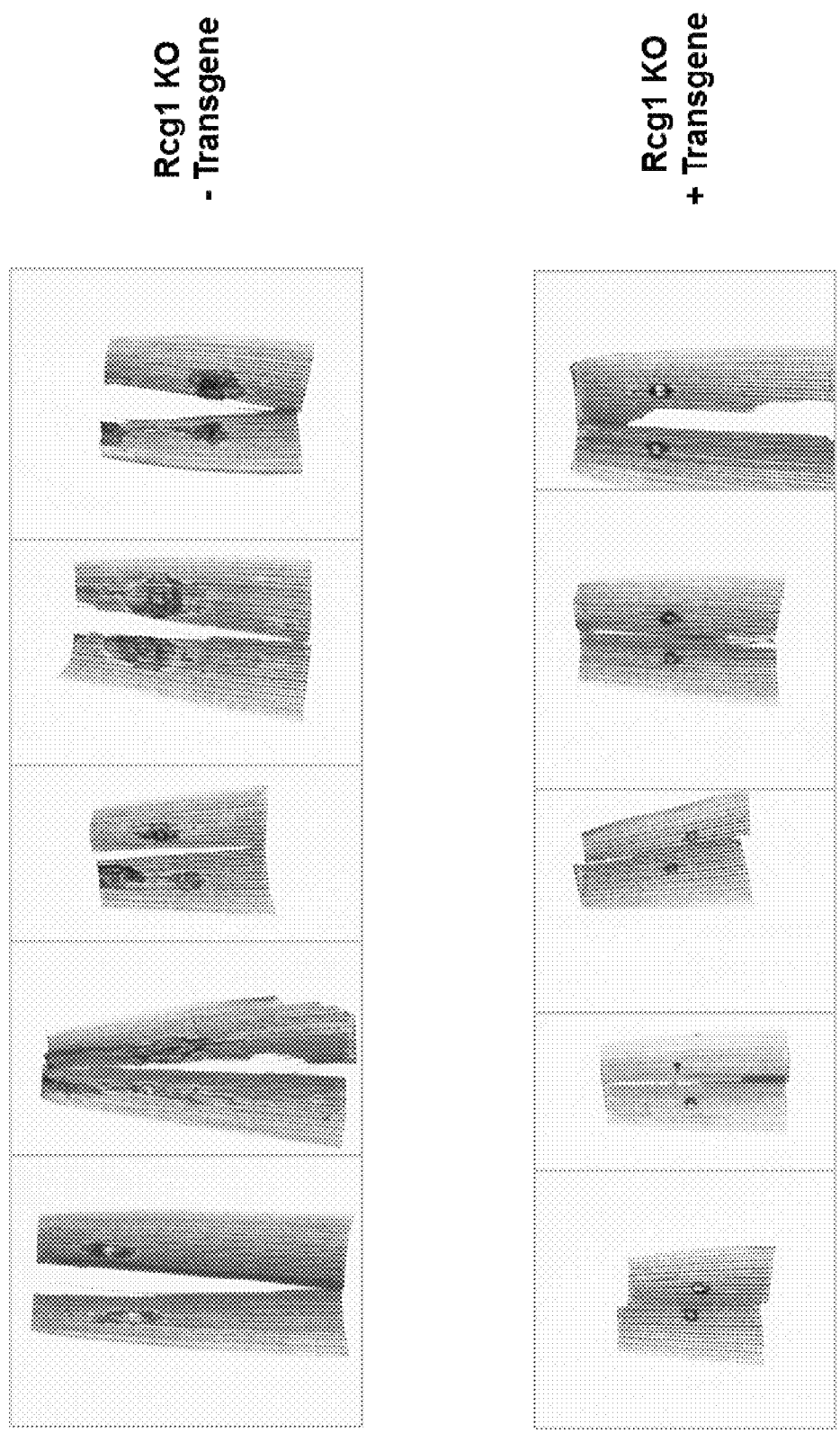
FIG. 27 shows a series of leaf sheaths of V7-9 maize plants which were inoculated with a suspension of Cg conidia following wounding of tissue. These results are further discussed in Example 8. In the absence of the Rcg1 transgene (top row), leaf sheaths of plants containing the Rcg1 gene display large, expanding necrotic lesions. In contrast, when the Rcg1 transgene (in this case driven by its own promoter) is present (bottom row), an ASR resistant phenotype is restored and necrosis is confined/restricted to the site of wounding and fungal inoculation.
Figure 33:
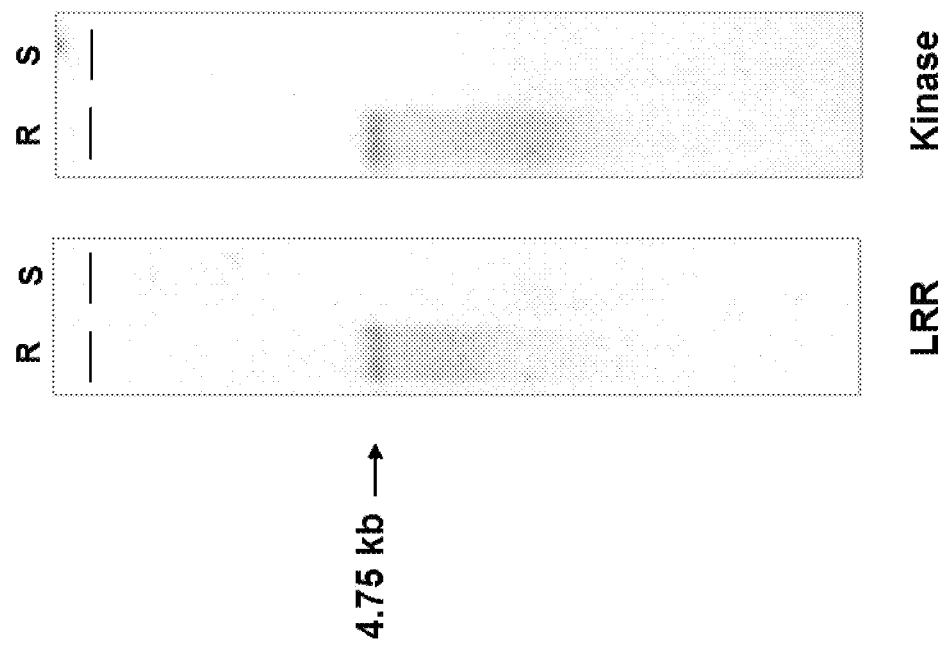
FIG. 33 summarizes the leaf sheath infection data for Rcg1 KO plants in the absence and in the presence of the native Rcg1 transgene, as discussed in Example 8.

The data from the leaf sheath infection assays are summarized in FIG. 33, and a typical result for one experiment is shown in FIG. 27. In the absence of the native Rcg1 transgene, leaf sheaths of plants containing the Mu-tagged Rcg1 gene display large, expanding necrotic lesions that typify the reaction of this ASR susceptible plant. In contrast, when the native Rcg1 transgene is present, an ASR resistant phenotype is restored and necrosis is confined or restricted to the site of wounding and fungal inoculation. The data in FIG. 33 show that the necrotic area decreases from a mean of 0.76 cm$^2$ in the absence to 0.14 cm$^2$ in the presence of the native Rcg1 transgene. Similarly, lesion size in plants containing the transposon-tagged Rcg1 gene decreases from a mean value of 0.89 cm$^2$ in the absence of the ubiquitin Rcg1 transgene to 0.11 cm$^2$ in the presence of the ubiquitin Rcg1 transgene. Thus, both the native and the ubiquitin Rcg1 transgenes are able to complement the knockout mutation in Rcg1 and to restore an ASR resistant phenotype, indicating that both constructs are functional. The fact that neither transgenic construct alone is able to provide resistance indicates that the Rcg1 gene is not sufficient for stalk rot resistance. The Rcg1 locus therefore contains an additional component that is required for resistance to Cg. The Rcg1 gene is therefore necessary but not sufficient.

Example 9

Analysis of DE811ASR BAC Clone Sequences to Identify Additional ASR Resistance Pathway Components The BAC clones from Example 2 covering the Rcg1 introgressed region of DE811 ASR were examined to search for potential candidate genes that may be required in addition to the Rcg1 gene for stalk rot resistance. The sequences of four overlapping BAC clones were inspected to identify predicted genes with homology to putative disease response-related proteins. A 79 kb supercontig (a 79 kb stretch of ordered, nearly continuous sequence, designated supercontig H) in BAC clone 191 was found to contain sequences encoding a protein showing homology to several NBS-LRR proteins from barley and rice. The alignment is shown in FIGS. 31*a* through 31*g*. This segment of the BAC contig covered 4101 bp, contained 2 predicted exons, one intron and encoded an 1164 amino acid ORF (open reading frame). Comparison of the sequence against a database of protein signatures revealed the presence of a typical LRR domain, a NB domain with subdomains and a short, protein kinase-like sequence in the last 37 amino acids of the ORF. In order to determine whether the NBS-LRR sequence was encoded by a functional gene that was expressed in DE811ASR plants, RT-PCR was performed. Total RNA (750 ng) from uninoculated and Cg inoculated (3,6,9,13 DPI) DE811 and DE811ASR samples was copied in cDNA using SUPERSCRIPT® III Reverse Transcriptase (Invitrogen, Carlsbad, Calif., USA) and amplified using PLATINUM® Taq DNA Polymerase (Invitrogen, Carlsbad, Calif., USA). The cDNA synthesis reaction was assembled according to the protocol supplied by the manufacturer using random hexamers as primers and incubated at 50° C. for 50 minutes. The reaction was then terminated by heating at 85° C. for 5 minutes and the RNA template was removed by digestion with RNaseH at 37° C. for 20 minutes. Primer pairs were selected to amplify 3 different fragments from the NBS-LRR cDNA template.

Figure 28:
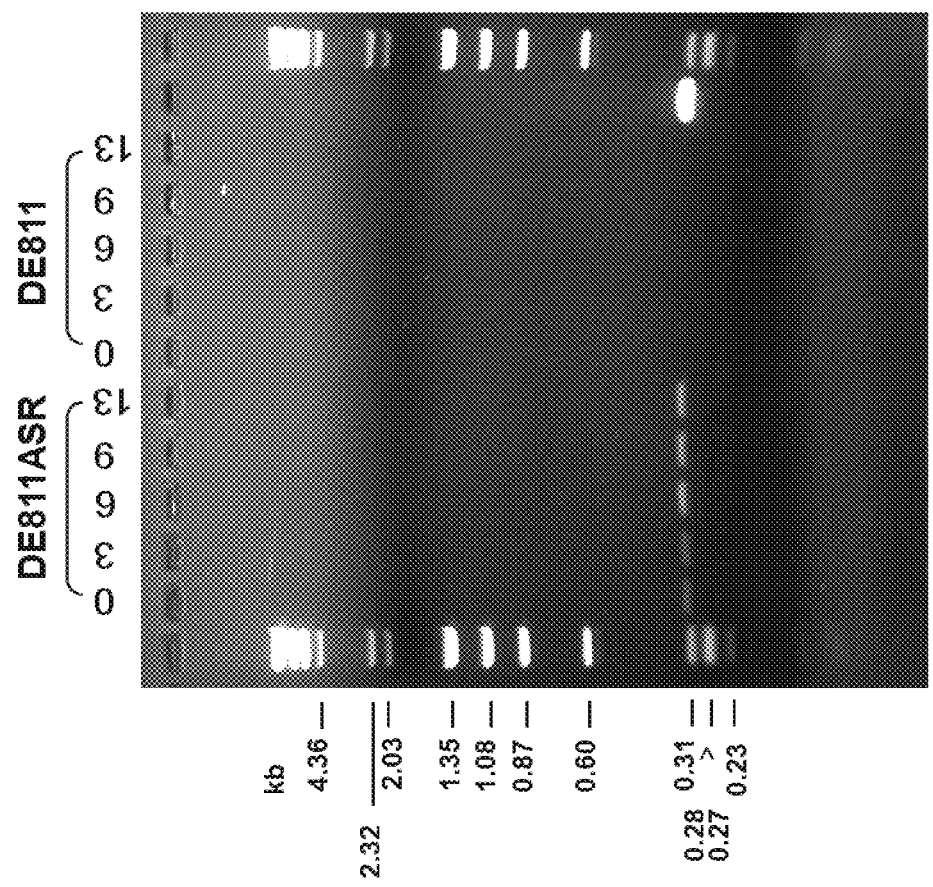
FIG. 28 shows the results of RT-PCR performed with the ETJ115-ETJ116 primer pair. This data clearly shows that the NBS-LRR gene of BAC clone 191 supercontig H is expressed exclusively in DE811ASR plants that contain the MP305 introgressed region, as discussed in Example 9.

These PCR primer pairs consisted of ETJ111 (SEQ ID NO: 234) and ETJ112 (SEQ ID NO: 235); ETJ113 (SEQ ID NO: 236) and ETJ114 (SEQ ID NO: 237); ETJ115 (SEQ ID NO: 238) and ETJ116 (SEQ ID NO: 239). The cDNA (1 µL of the reverse transcriptase reaction) was amplified for 30 cycles consisting of 30 seconds at 94° C., 30 seconds at 50° C. and 1 minute at 72° C. followed by a 7 minute extension at 72° C. FIG. 28 shows the results of RT-PCR performed with the ETJ115-ETJ116 primer pair. This data clearly shows that the NBS-LRR gene of BAC clone 191 supercontig H is expressed exclusively in DE811ASR plants that contain the MP305 introgressed region. Similar results were obtained when cDNA amplification was carried out using the ETJ111-112 and the ETJ113-114 primer pairs. DNA sequence analyses verified that all three RT-PCR products were derived from the NBS-LRR sequence of BAC191 supercontig H.

The NBS-LRR sequence obtained from the BAC clone did not contain an obvious stop codon and thus was only partial in nature. In order to define the end of the coding region and to obtain a complete sequence of the transcript, a 3' RACE experiment was carried out. Total RNA from DE811ASR uninoculated and Cg inoculated (6 DPI) plants was copied into cDNA using SUPERSCRIPT® III RT and an oligodT primer using standard conditions. The cDNA was then subjected to two rounds of amplification with PLATINUM® Taq DNA Polymerase using the nested gene specific primers oETJ118 (SEQ ID NO: 241) and oETJ119 (SEQ ID NO: 242) and an oligodT adaptor primer, oETJ117 (SEQ ID NO: 240). The results of this procedure provided an additional 976 bp of sequence. Combination of the sequences from BAC clone 191 and the 3' RACE product leads to the prediction of an approximate 4.5 kb transcript encoding a 1428 amino acid polypeptide. In order to confirm this composite sequence, a full length cDNA was isolated by RT-PCR using SUPERSCRIPT® III RT in combination with PHUSION™ Hot Start High Fidelity DNA Polymerase (New England Biolabs, Ipswich, Mass., USA). cDNA synthesis was primed by oligodT using total RNA from DE811ASR (0, 13 DPI) plants. Amplification with PHUSION™ polymerase employed the gene specific primers oETJ 120 (SEQ ID NO: 243) and oETJ121 (SEQ ID NO: 244) which were positioned to amplify a fragment extending from the translational start site to 31 bp beyond the stop codon. Sequence analysis of the resultant 4318 bp fragment showed perfect agreement between the cDNA sequence and the composite BAC clone plus RACE product sequence.

Figure 29:
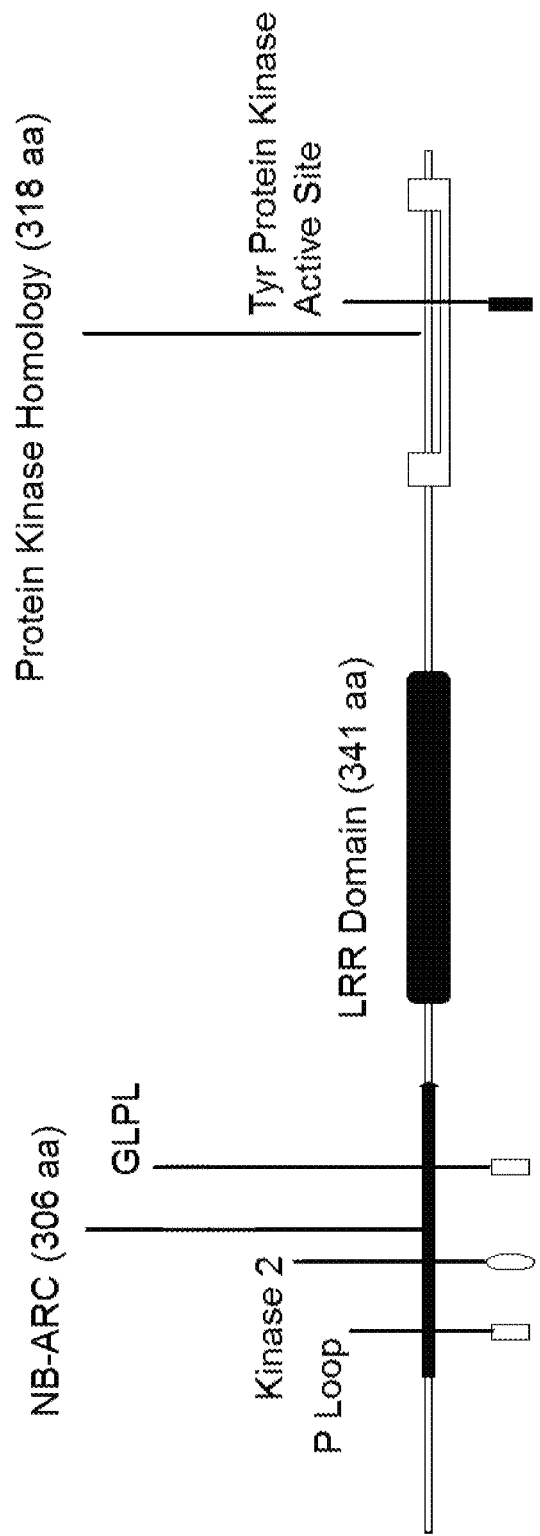
FIG. 29 shows the predicted domain structure of the Rcg1b gene, as discussed in Example 9.

The sequence of the 4318 bp cDNA fragment is given in SEQ ID NO: 245. The deduced 1428 amino acid sequence of the 4287 bp ORF is set forth in SEQ ID NO: 246. The gene was designated Rcg1b. A BLAST® P homology search performed with the 1428 aa sequence revealed good homology to NBS-LRR sequences over the first ~900 amino acids of the sequence (FIGS. 31*a* through 31*g*). In addition, good homology was found between amino acids 1036-1399 of the sequence (set forth in SEQ ID NO: 256) and several putative protein kinases (FIGS. 32*a* and 32*b*). When the protein sequence is queried against a database of protein families, domains and sites, a tripartite structure consisting of an NB-ARC, LRR and protein kinase domain is obtained. The domain structure of the Rcg1b polypeptide is diagrammed in FIG. 29. The inclusion of these three domains within a single polypeptide is not commonly found. However, a barley NBS-LRR-PK gene, Rpg5, proposed to function in resistance to *Puccinia graminis* has been identified (Brueggeman et al., (2005) Abstracts of Plant and Animal Genomes XIII Conference, Poster 320 [online], [retrieved on 2007 Jun. 8]. Retrieved from the Internet:<URL: http://www.intl-pag.org/13/abstracts/PAG13_P320.html>

Comparison of the cDNA sequence with the genomic BAC clone sequence indicates that the Rcg1b gene is divided into 9 exons and 8 introns and covers greater than 44 kb. Introns 2-8 are concentrated in the protein kinase portion of the gene. Two of these introns are extremely long: intron 2 is 16.7 kb and intron 5 is 20.6 kb. The initial genomic sequence that was obtained for the Rcg1b gene and its flanking regions is provided in SEQ ID NOs:255-258. Due to the highly repetitive nature of some of the sequence elements between the two genes, some areas of the genomic DNA presented significant sequencing difficulties. After initial sequencing, there were three gaps of sequence located in intron 5 of the Rcg1b genomic sequence. The segment of the genomic sequence corresponding to the first 5 exons and the first 4 full introns, as well as the start of the 5th intron (prior to the first sequence gap) is set forth in SEQ ID NO: 255. This segment includes the start codon (ATG), the TATA box, and a CAAT element. The second and third segments of the genomic sequence of Rcg1b correspond to two portions of the 5th intron, between which the second sequence gap exists, and are set forth in SEQ ID NOs: 256 and 257. The fourth and final segment of the genomic sequence of Rcg1b corresponds to the remainder of the 5th intron, after the third sequence gap, through the remaining 3 full introns and 4 full exons. This segment is set forth in SEQ ID NO: 258, and includes the stop codon of the Rcg1b sequence, as well as the 3' UTR and 3' flanking genomic sequences. Further sequencing efforts were able to eliminate the gaps in intron 5 of the genomic sequence for Rcg1b. The complete genomic sequence for the Rcg1b gene is therefore set forth in SEQ ID NO: 266, with the positions of all exons and introns indicated in the sequence listing accompanying this application. There is a small region within SEQ ID NO: 266 represented by a stretch of 21 "n" residues that is not a gap, but rather is a result of poor sequence quality in which the 21 positions have yet to be positively confirmed. At present, the complete DNA sequence of the genomic interval between Rcg1 and Rcg1b is not known because there is one remaining small gap in the genomic DNA sequence, located between the two genes, which has proven difficult to sequence because of repetitive elements.

Figure 30:
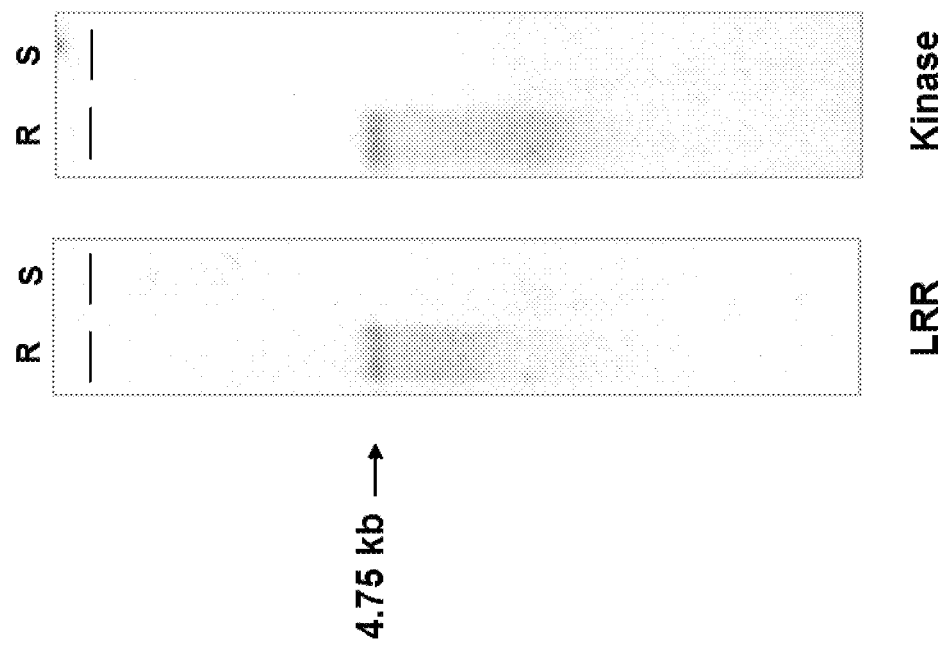
FIG. 30 shows the result of a northern blot analysis which allowed an independent confirmation of Rcg1b expression and provided an estimate of transcript size. Northern blots of polyA+ RNA (0.7 mg) from resistant and susceptible plants (0, 6, 13 DPI) showed the presence of a 4.75 kb transcript band, present only in the resistant samples that hybridized specifically with probes prepared from the LRR and the kinase region of the gene, as discussed in Example 9.

Northern blot analysis allowed an independent confirmation of Rcg1b expression and provided an estimate of transcript size. Northern blots of polyA+ RNA (0.7 µg) from resistant and susceptible plants (0, 6, 13 DPI) showed the presence of a 4.75 kb transcript band, present only in the resistant samples that hybridized specifically with probes prepared from the LRR and the kinase region of the gene. (FIG. 30). The observed transcript size agrees well with the size calculated from cDNA and RACE products (4.68 kb). An MPSS® tag predicted from the Rcg1b cDNA sequence is found to be present at a low level (≤144 ppm) only in DE811ASR libraries. This finding is consistent with RT-PCR and Northern blot results and confirms the exclusive presence of this low abundance transcript in ASR resistant plants.

Example 10

Dual Expression of Rcg1 and Rcg1b as Transgenes: Both Rcg1 and Rcg1b Transgenes are Required for Resistance to *Colletotrichum graminicola*

The Rcg1 and Rcg1 b genes can be expressed as transgenes, allowing modulation of their expression in different circumstances. The following disclosure shows how the two genes could be expressed in different ways to combat different diseases or to protect different portions of the plant, or simply to move the two genes into different corn lines as transgenes, as an alternative to moving the entire Rcg1 locus through crossing as described in Example 5.

For assembly of an Rcg1b gene driven by its native promoter, 3 Rcg1b fragments were joined together in a GATEWAY® entry vector containing attL3 and attL4 recombination sites, separated by a multiple cloning site region. A 2.4 kb BamHI-KpnI fragment containing 1967 bp of upstream sequence and 432 bp of the Rcg1b coding region, a 3.7 kb KpnI-BsaI fragment of the Rcg1b cDNA, and a 1.1 kb BsaI-SmaI fragment containing 146 bp of the Rcg1b cDNA plus 939 bp of 3' flanking DNA were joined in a 4-way ligation to BamHI-SmaI digested L3/L4 entry vector to give Construct A. The native promoter driven Rcg1b construct was then transferred by recombination, along with the native Rcg1 construct of Example 6a into a destination vector containing attL1/attL2 and attL3/attL4 sites to give a stacked Rcg1 promoter-Rcg1/Rcg1b promoter-Rcg1b construct (Construct B).

For high level constitutive expression, a ubiquitin promoter-driven Rcg1b construct was generated. For this construct, an Rcg1b fragment spanning nucleotides 1 through 4318 of the cDNA sequence was amplified as a BamHI-SnaBI fragment by RT-PCR and inserted into a GATEWAY® entry vector containing the ubiquitin promoter, 5'UTR, intron and the PinII terminator flanked by attL3 and attL4 sites to produce Construct C. An analogous construct was generated for Rcg1 (Construct D), in this case in a GATEWAY® entry vector where the ubiquitin promoter and PinII terminator are flanked by attL1 and attL2 sites. Both the Rcg1b and Rcg1 ubiquitin driven genes were transferred by an LR recombination reaction into the destination vector noted before this time to yield a stacked Ubi-Rcg1/Ubi-Rcg1b construct (Construct E). One of skill in the art would be able to select a different promoter to express the Rcg1 and Rcg1 b genes, or two different promoters, each one expressing one of the two genes.

The above-described constructs were transformed into corn using the method of Example 7. Two separate experiments were performed involving transformation of the construct from Example 6a, Construct A and Construct B in one experiment and Construct C, Construct D and Construct E in the other. For the first experiment, a total of 15, 10 and 30 events were generated from transformation of corn with the construct from Example 6a, Construct A and Construct B, respectively. To confirm expression of the DNA constructs, molecular analyses were performed. Leaf discs of each native gene transgenic event were harvested for total RNA isolation. RT-PCR was performed using the Rcg1-specific primers Alex1F and Alex1R set forth in SEQ ID NOs: 260 and 42, respectively, and the Rcg1b-specific primers ETJ144 and EJT145 set forth in SEQ ID NOs: 261 and 262, respectively. Upon RT-PCR, all 10 of the Construct A events contained the expected 491 bp Rcg1b band and all 15 of the events transformed with the construct from Example 6a contained the expected 420 bp Rcg1 band. Of the 30 events generated from transformation with the stacked Rcg1 and Rcg1b native genes (Construct B), 29 expressed both transgenes while a single event was found to express one transgene (Rcg1) but not the other (Rcg1b). Disease assays were performed in the greenhouse on the same transgenic events in order to determine whether the plants were resistant to Cg. Leaf sheath assays were first carried out on 3 sibling plants of each event using the procedure described in Example 8. Infected plants were scored 5 days after inoculation with Cg by quantitation of lesion size through LemnaTec (LemnaTec, Würselen, Germany) image analysis. No significant difference in lesion size was found between transgenic plants containing any one of the 3 different constructs (Table 6a). Mean lesion size for plants containing the construct from Example 6a was 1.286 cm$^2$, while that for Construct A and Construct B were 1.070 and 1.174 cm$^2$, respectively.

Thus, while RT-PCR data indicated that all three constructs showed good expression in transgenic plants, no effect on resistance to Cg could be demonstrated for either the Rcg1 or Rcg1b native gene construct alone or for the stacked construct containing both genes in combination. Similar results were obtained when the same transgenic events were subjected to stalk inoculation with Cg.

TABLE 6a

Transgenic Plant Results: Lesion Size

| DNA | # of Plants | Mean Lesion Size (cm$^2$) | Std Deviation |
| --- | --- | --- | --- |
| Construct from Example 6a | 34 | 1.286 | 0.683 |
| Construct A | 25 | 1.070 | 0.567 |
| Construct B | 78 | 1.174 | 0.530 |

Figure 34:
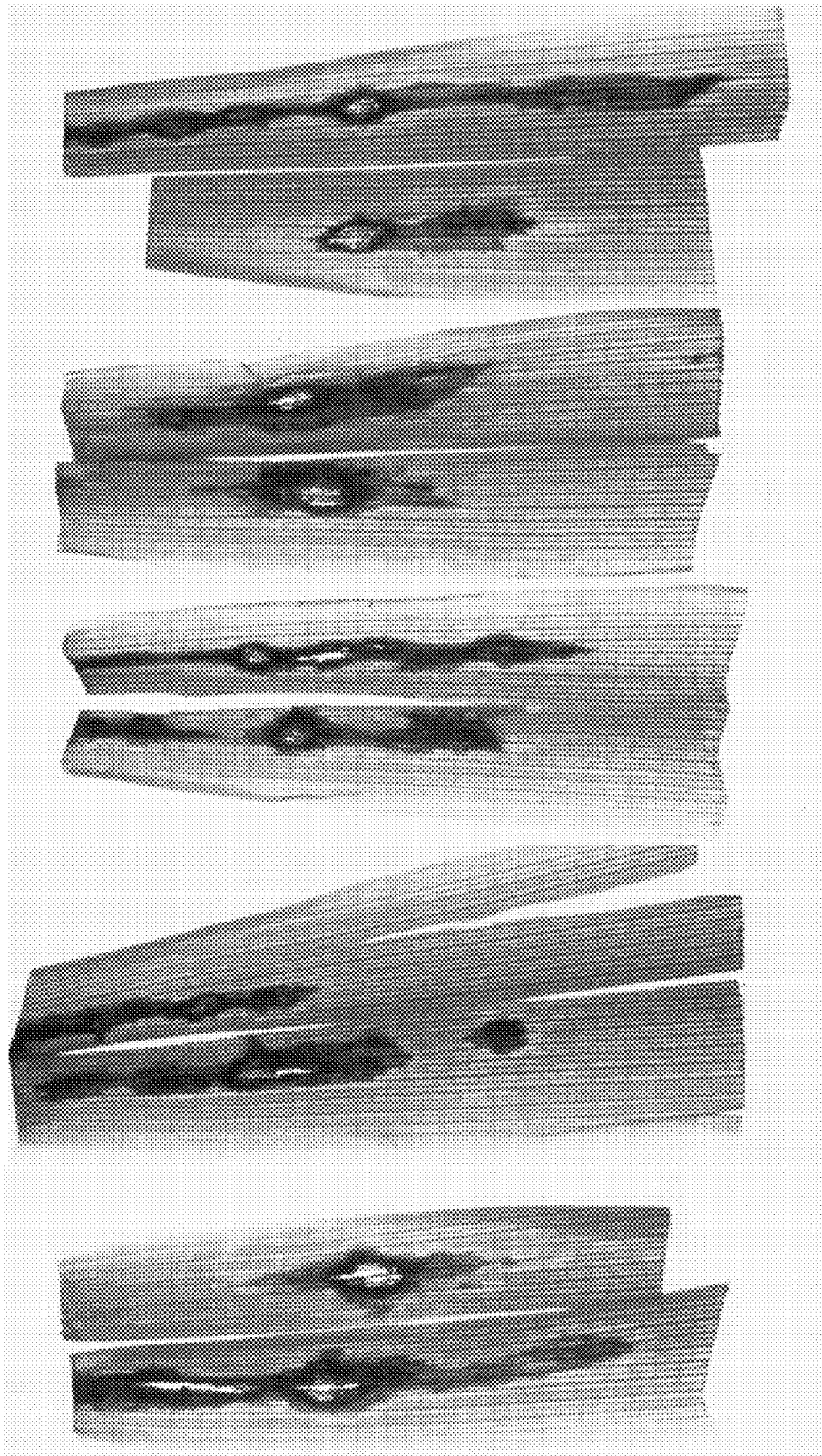
FIG. 34 shows the results of leaf sheath assays from plants transformed with Construct E as described in Example 10. A clear pattern of Cg infection is visible.
Figure 35:
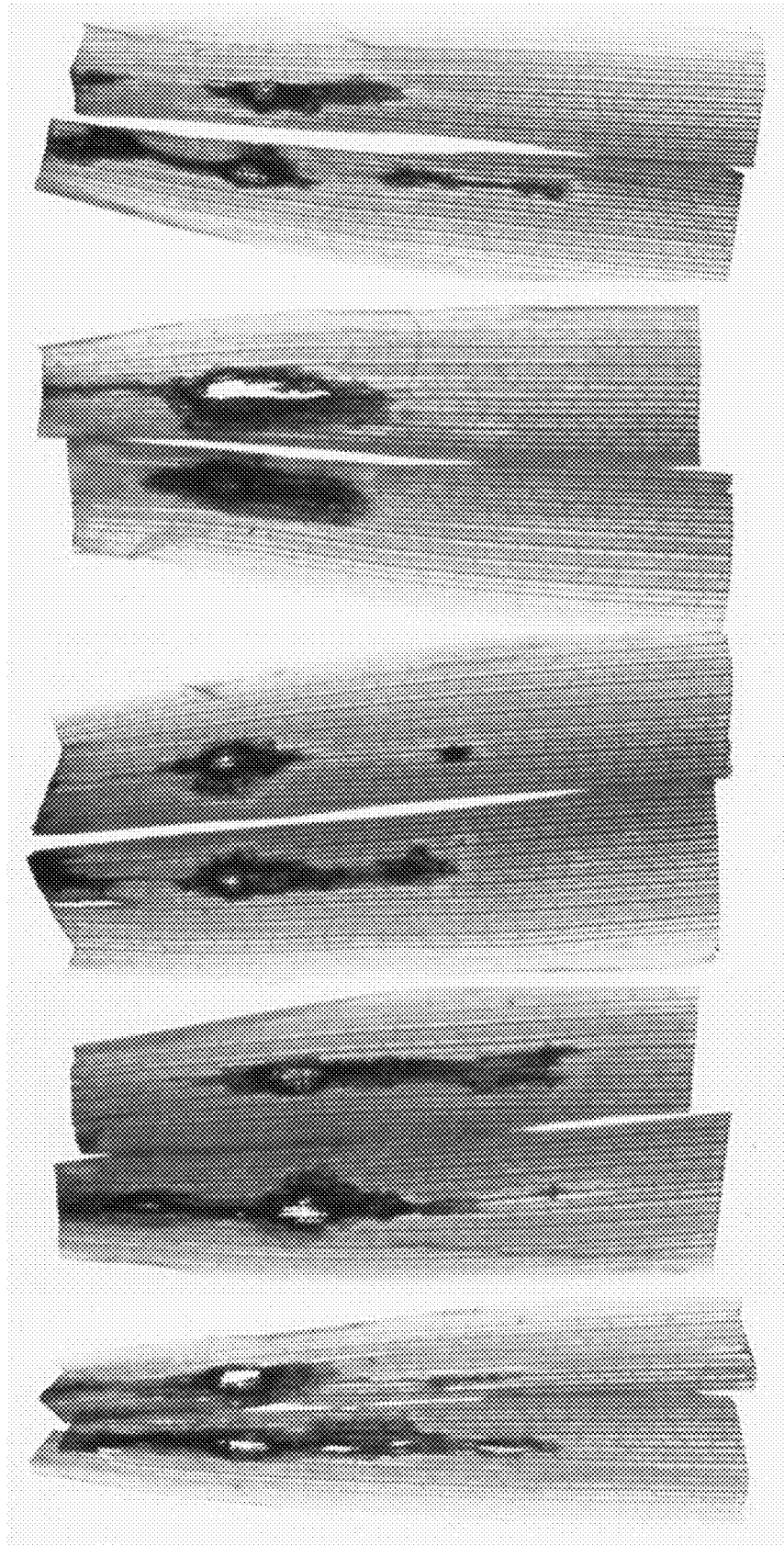
FIG. 35 shows the results of leaf sheath assays from plants transformed with Construct C as described in Example 10. A clear pattern of Cg infection is visible.
Figure 36:
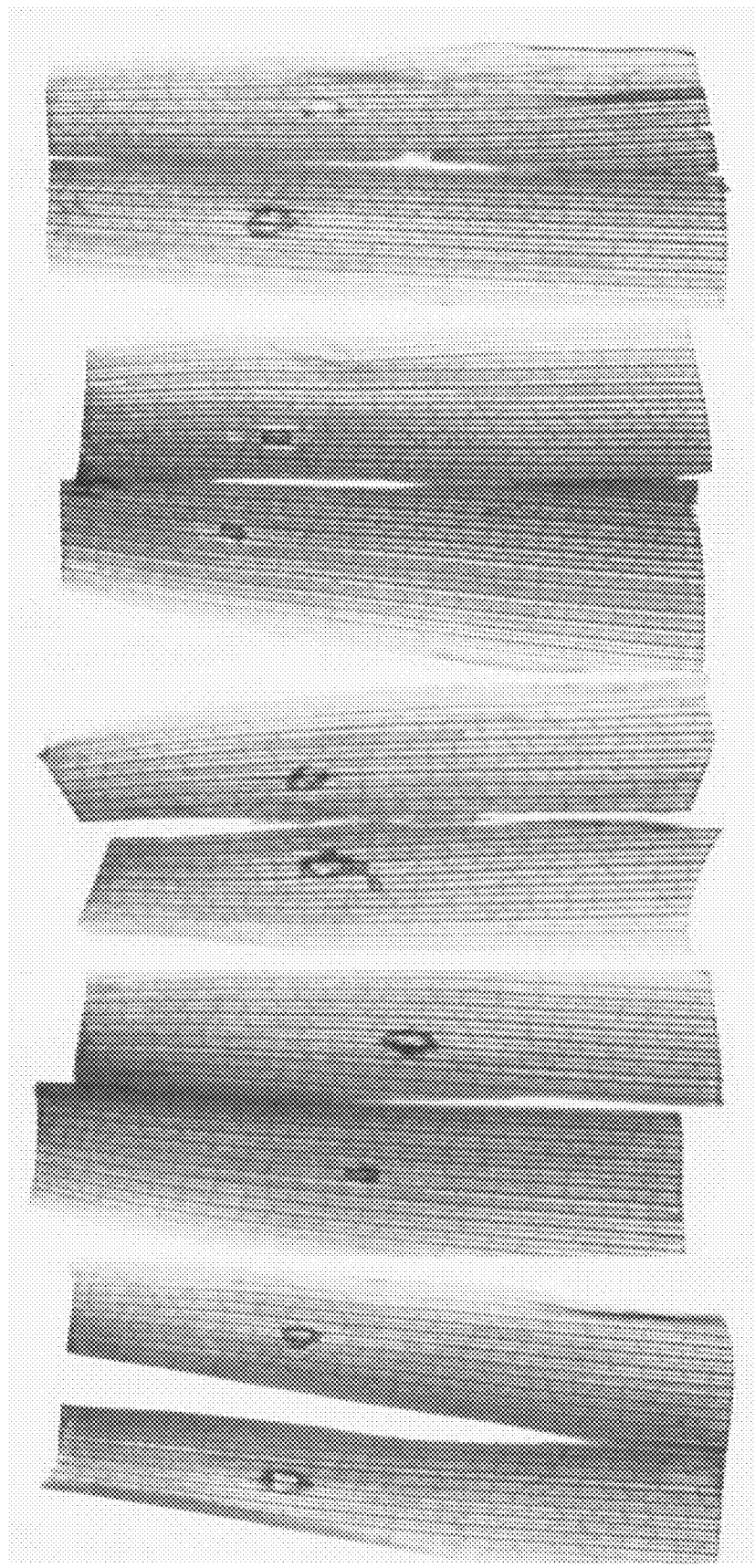
FIG. 36 shows the results of leaf sheath assays from plants transformed with Construct D as described in Example 10. The leaves clearly show inhibition of Cg infection as a result of the simultaneous presence and expression of both the Rcg1 and Rcg1b genes.

In contrast to the results with the native gene constructs, significant differences in Cg resistance were found for transgenic plants containing the constructs driven by the maize ubiquitin promoter. As shown in Table 6b, mean lesion size for plants containing the single gene Construct C (Ubi-Rcg1b) and Construct E (Ubi-Rcg1) were 1.879 and 1.897 cm$^2$, respectively. However, plants containing the stacked Ubiquitin-gene construct (Construct D) showed a significant reduction in lesion area with the mean lesion size corresponding to 0.345 cm$^2$. These results are shown in FIGS. 34 through 36. RT-PCR analysis confirmed expression of the Rcg1b transgene in 15/15 Construct C events and the Rcg1 transgene in 13/15 Construct E events. Good expression of both Ubiquitin-promoter driven transgenes was found in 27/30 Construct D events. Two events lacked detectable expression of both transgenes; one event showed strong expression of Rcg1b, but no apparent expression of Rcg1. The leaf sheath infection assay data indicate that neither Rcg1 nor Rcg1b alone confer resistance to Cg and instead that both Rcg1 and Rcg1b are required for expression of the resistance phenotype.

TABLE 6b

Transgenic Plant Results: Lesion Size

| DNA | # of Plants | Mean Lesion Size (cm$^2$) | Std Deviation |
| --- | --- | --- | --- |
| ASR | 8 | 0.480 | 0.259 |
| DE811 | 8 | 4.538 | 0.970 |
| Construct C | 38 | 1.879 | 1.097 |
| Construct E | 37 | 1.897 | 1.030 |
| Construct D | 78 | 0.345 | 0.650 |

An interesting and unexpected observation noted above is that the Rcg1 and Rcg1b transgenes, driven by the ubiquitin promoter, together provide resistance to infection by Cg while the transgenes driven by their endogenous promoter do not. It is known that the ubiquitin promoter (in combination with maize ubiquitin intron I) is able to generate high level constitutive expression of marker and trait genes in assorted tissues under assorted developmental and environmental conditions. Detailed characterization of the Rcg1 or Rcg1b promoter fragments used in the constructs of the present invention has not been carried out. The Rcg1 native gene in the construct from Example 6a was shown in Example 8 to complement a Mu-insertion knockout in the gene, indicating that the construct and thus the included promoter fragment is functional. Since no detailed studies of the Rcg1b promoter fragment of Construct A and Construct B have been carried out, it appears that not all of the necessary information required for accurate regulation of the gene is encoded in this 5' fragment. The infection data indicate that when the 1835 bp promoter fragment is used to drive expression, Rcg1b is not correctly expressed. Although the functional Rcg1b promoter has not yet been defined, the Ubi-Rcg1b results demonstrate that any functional promoter may be used to drive expression of the gene and this may be combined with Rcg1 expression to produce resistance to infection by Cg.

Example 11

Analysis of Rcg1 Gene Distribution Across Germplasm and Identification of Rcg1 Sequence Variants Following the identification, sequencing and fine mapping of Rcg1, other lines were screened for the Rcg1 gene. To determine the presence of the Rcg1 gene in other maize germplasm, gene specific primers combinations FLP111F and FLP111R as well as FLP113F and FLPA1R were used to amplify genomic DNA from a diverse panel of maize inbred lines, including those lines listed on Table 18 and F2834T, by polymerase chain reaction. In only 14 (including MP305) out of the panel of maize inbred lines an amplification product was detected, indicating that the Rcg1 gene is only present in a very small percentage of the inbred lines that were screened. Thus, in addition to using MP305 or DE811ASR (BC5) as the donor source, other sources containing the Rcg1 gene can also be used as a donor source. For example the public inbred lines TX601 (available under ID 'Ames 22763' from National Plant Germplasm System (NPGS)) and F2834T (available under ID 'Ames 27112' from NPGS) which contain the Rcg1 gene can be used as donor sources in crosses with other maize inbred lines not containing the Rcg1 gene, and selecting for the Rcg1 gene by using markers as described herein.

Variants of the Rcg1 gene were also identified and analyzed for single nucleotide polymorphisms (SNPs). SNPs were identified at positions on Sequence ID number 1 corresponding to one or more of position 413, 958, 971, 1099, 1154, 1235, 1250, 1308, 1607, 2001, 2598 and 3342. (See Table 7). Not all of the allelic variants of the Rcg1 gene indicated a resistant phenotype. Therefore, these SNPs can be used as markers to precisely identify and track the Rcg1 sequence in a plant breeding program, and to distinguish between resistant and susceptible allelic variants. Further, these SNPs indicate that there are variant sequences that show a resistant phenotype and can be used in the methods and products disclosed herein. Four other lines have also been found to contain an Rcg1 allele: BYD10, 7F11, CML261 and CML277. Testing of 10 plants did not provide sufficient data to conclusively determine whether line 7F11 is resistant. No data are available on the resistance of the BYD10, CML261 and CML277 lines.

TABLE 7

SNPs identified in allelic variants of the Rcg1 gene

| | | | Consensus position | | | | | | | | | | | |
|---|---|---|---|---|---|---|---|---|---|---|---|---|---|---|
| | Phenotype | # Plants Tested | 413 | 958 | 971 | 1099 | 1154 | 1235 | 1250 | 1308 | 1607 | 2001 | 2598 | 3342 |
| SEQ ID NO: 1 from DE811ASR (BC5) | Resistant | Over 500 plants over 4-5 years | A | A | G | C | C | A | A | C | A | A | G | C |
| PHBTB | Resistant | 150-210, over 3 years | A | A | G | C | C | A | A | : | A | A | G | C |
| PH26T | Resistant | 50, over 1 year | A | A | G | C | C | A | A | : | A | A | G | C |
| TX601 | Insufficient data | 10, over 1 year | A | A | G | C | C | ? | A | : | A | A | G | C |
| F2834T | No data | — | A | A | G | C | C | A | A | : | G | G | A | A |
| B54 | No data | — | C | C | C | T | A | A | T | : | G | G | A | A |
| PH0RC | Insufficient data | 19, over 1 year | C | C | C | T | A | A | T | : | G | G | A | A |
| PH277 | Insufficient data | 17, over 1 year | C | C | C | T | A | A | T | : | G | G | A | A |
| PHDGP | Susceptible | 150-210, over 3 years | C | C | C | T | A | A | T | : | G | G | A | A |
| PHDH7 | No data | — | C | C | C | T | A | A | T | : | G | G | A | A |
| MP305 (public) | Resistant | 50 | A | A | G | C | C | A | A | C | A | A | G | C |

Length of Consensus = 4212 nucleotides. SEQ ID NO: 1 is the Rcg1 sequence. For the remaining lines, the sequence available spanned from the "atg" start codon in the first exon to the "tga" stop codon in the second exon. The consensus position is based on SEQ ID NO: 1.

Example 12

Figure 17:
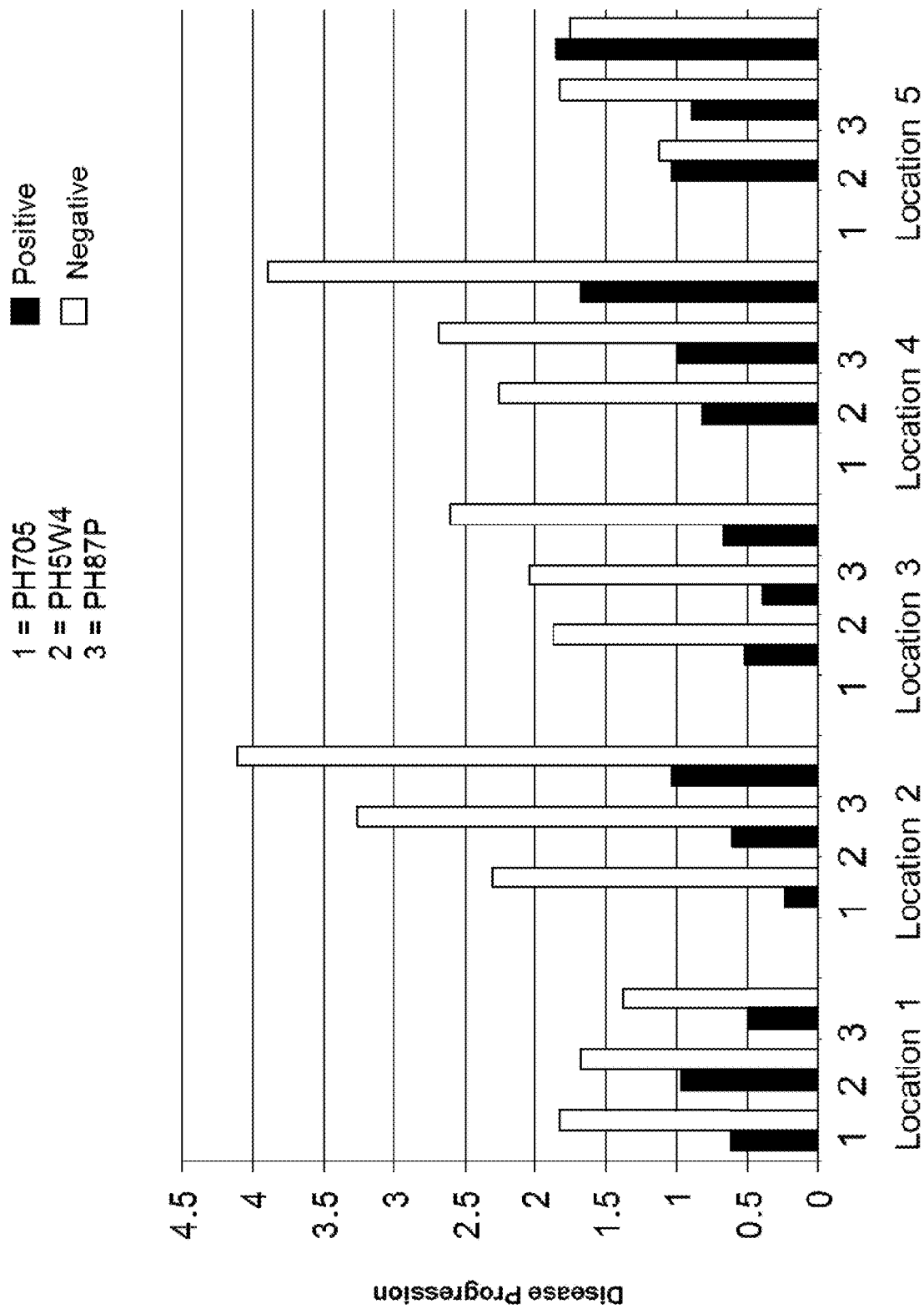
FIG. 17 shows the severity of disease four to five weeks after inoculation at 5 different locations caused by Cg in stalks of hybrids derived from crossing DE811ASR(BC5) to the line indicated. Differences between the lines which were positive and negative for the Rcg1 gene are statistically significant at a P value of less than 0.05, except for location 5.
Figure 18:
FIG. 18 shows disease progression in representative stalks from hybrids created from PH4CV and PH705 lines which are positive and negative for Rcg1.
Figure 19:
FIG. 19 shows disease progression in representative stalks from hybrids created from PH705 and PH87P lines which are positive and negative for Rcg1.
Figure 20:
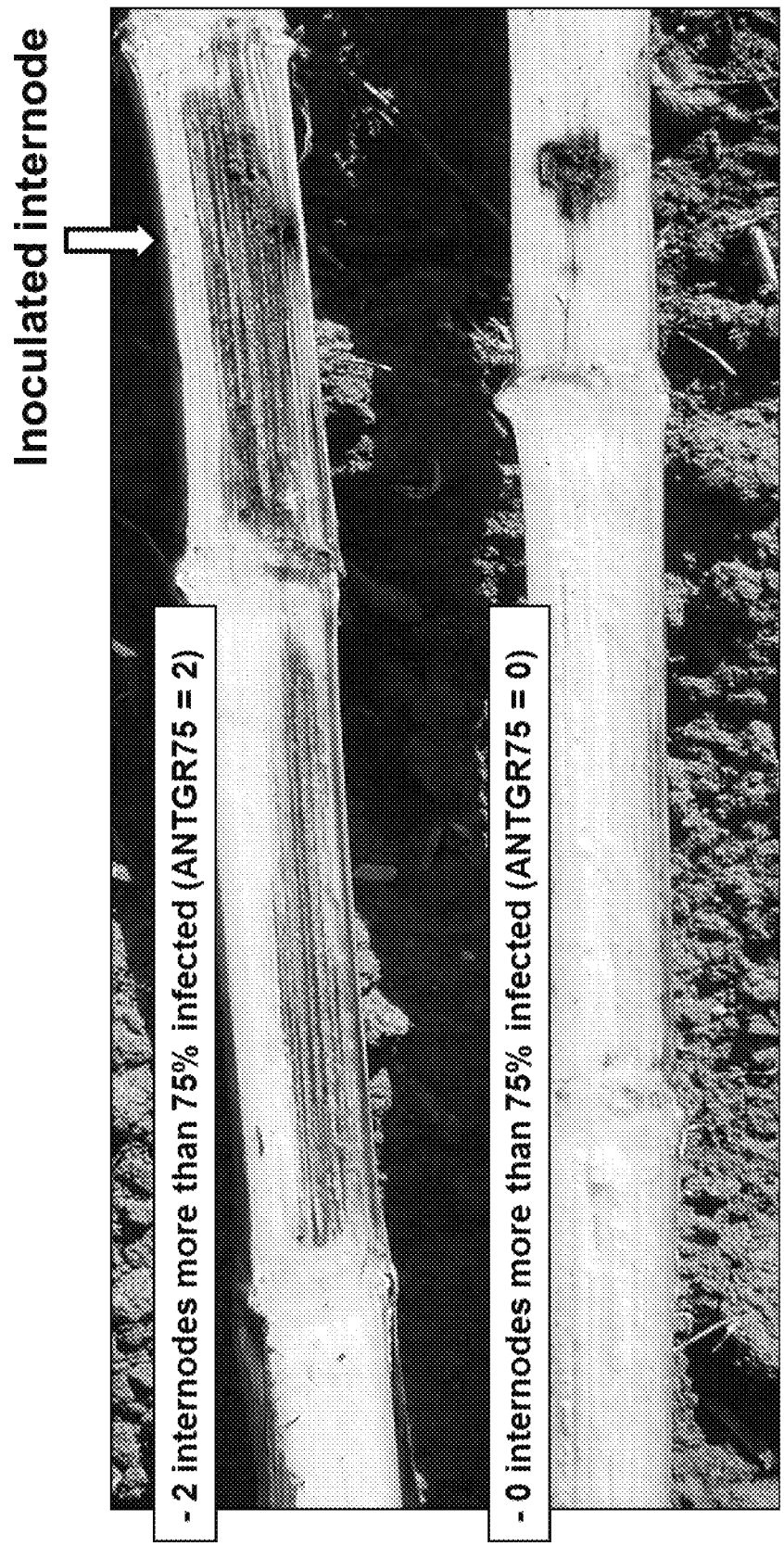
FIG. 20 shows the method of scoring for disease severity in corn stalks. The stalks are given a score, designated antgr75, which represents the number of internodes (up to 5, including the inoculated internode) that are more than 75% discolored. This results in a score ranging from 0 to 5, with 0 indicating less than 75% discoloration in the inoculated internode, and 5 indicating 75% or more discoloration of the first five internodes, including the inoculated internode.

Lines Containing the Rcg1 Locus are Resistant to Anthracnose-Induced Leaf Blight The near isogenic lines DE811 and DE811ASR described in Example 1 were tested for differences in resistance to leaf blight caused by Cg using the following procedure. Four common household sewing needles were glued to a metal support such that the holes for the thread extended out from the piece of metal, with all four needles extending an equal distance. This apparatus was dipped in a suspension of Cg spores at $5\times10^6$ spores/mL and then pushed through the surface of a young corn leaf such that the leaf was wounded and the wounds simultaneously inoculated with the spores. A wet cotton swab was placed on the midrib near the inoculation site and the entire area covered with plastic film and, over that, reflective cloth, both attached with tape, to keep it moist and shaded. The plants were left in this state for 50-54 hours in a standard greenhouse, after which the tape, cloth and plastic film were removed. At 7 and 15 days after inoculation the size of the lesion was measured and recorded in units of square centimeters.

FIG. 10 (*a-b*) shows the distribution of lesion sizes 15 days after inoculation across all the individual leaves. Lesion sizes vary in each data set, but virtually all of the DE811 leaves (FIG. 10*b*) had lesion sizes significantly larger than the largest lesions to be found on the DE811ASR(BC5) leaves (FIG. 10*a*). The data are summarized for both the 7 day and 15 day post-inoculation data sets in FIG. 11. At both 7 and 15 days, the average lesion size was smaller on the leaves carrying the Rcg1 gene. The difference becomes larger over time as the fungus has time to grow and cause further damage, so that while the difference is approximately two fold at 7 days, by 15 days it is more than four fold and in fact the fungus has made only minor progress on the DE811ASR(BC5) leaves. These results clearly demonstrate that the presence of the locus containing the Rcg1 gene confers resistance to anthracnose leaf blight.

Example 13

Hybrid Lines Derived from DE811ASR(BC5) have Higher Yield than Hybrids Derived from DE811 when Infected with *Colletotrichum graminicola*

In order to demonstrate that corn hybrids containing the Rcg1 locus have higher yield potential when infected with Cg than hybrid lines without Rcg1, DE811ASR (BC5) and DE811, the isogenic lines described in Example 1, were each crossed to inbred lines B73Ht and Mo17Ht, which are both susceptible to Cg.

The hybrid lines were grown and evaluated for response to Cg in 2005 at six locations in five different states of the USA. For each hybrid line, three replications of four rows were planted at approximately 74,000 plants per hectare. Plants were inoculated with Cg at the base of the stalk approximately 10 days after flowering. The first row of each four-row plot was evaluated to determine if the inoculations had been successful by determining the response to Cg four to five weeks after inoculation. The stalks were split and the progression of the disease was scored by observation of the characteristic black color of the fungus as it grows up the stalk. Disease ratings were conducted as described by Jung et al. (1994) *Theoretical and Applied Genetics,* 89:413-418). The total number of internodes discolored greater than 75% (antgr75) was recorded on the first five internodes (See FIG. 20). This provided a disease score ranging from 0 to 5, with zero indicating no internodes more than 75% discolored and 5 indicating complete discoloration of the first five internodes. The center two plots were harvested via combine at physiological maturity and grain yield in kg/ha was determined.

The results summarized over all locations are shown in FIG. 12 for disease severity and in FIG. 13 for yield. The data show that hybrids containing Rcg1 (DE811ASR(BC5)/B73Ht and DE811ASR(BC5)/Mo17Ht) have much less disease progression than hybrids without Rcg1 (DE811/B73Ht and DE811/Mo17Ht). The high scores for disease progression in the susceptible hybrids (lacking Rcg1) show the successful infection of the experiment with Cg. Furthermore, the data show that when infected with Cg, hybrids containing the Rcg1 locus have a higher yield than hybrids lacking Rcg1. Differences of the individual pairwise comparisons are significant at $P<0.05$.

These results clearly demonstrate that by using the methods of the embodiments one can create hybrids that yield more kg of grain per hectare when infected with Cg.

Example 14

Inbred and Hybrid Rcg1 Locus Conversions Derived from DE811ASR (BC5) or MP305 are Resistant to *Colletotrichum graminicola* Induced Stalk Rot In order to demonstrate that commercial corn lines can be made resistant to Cg-induced stalk rot, MP305 and DE811ASR (BC5) were crossed with PH87P, PH5W4, and PH705. The resulting progeny were crossed again to the same three lines (i.e., the lines were used as recurrent parents in a backcrossing program) three more times, each time selecting for the presence of the Rcg1 locus using molecular markers as described in Example 5 above. As controls, selected backcross lines which lacked the Rcg1 locus were also collected from the same backcrossing program. After three backcrosses were completed, several versions were selected and selfed to obtain BC3S1 families. Individual BC3S1 plants were genotyped and plants homozygous positive and homozygous negative for Rcg1 were selfed to obtain BC3S2 families, which were then phenotyped. BC3S2 versions containing Rcg1 and, as controls, selected versions without the gene, were planted in single row plots containing approximately 25 plants per row. The experiment was planted in five different locations in five different states of the United States, designated Locations 1, 2, 3, 4, and 5. At approximately two weeks after flowering, plants were inoculated with Cg at the base of the stalk. Four to five weeks later the stalks were split and progression of the disease evaluated by visually estimating the amount of disease in the stalk. A visual score was assigned to each stalk based on the degree of infection of each internode for the inoculated internode and the four internodes above the inoculation internode. A low score thus indicates resistance to the disease. The compiled results for all rows and locations are summarized in FIG. 14. Representative pictures of two lines are shown in FIGS. 15 and 16. The data show that at all locations, each of the elite inbred lines was made more resistant to the disease by the presence of the Rcg1 locus.

Corn seed sold to farmers is “hybrid,” meaning that it is most commonly the result of a cross of two inbred parents, referred to as a single cross hybrid. Many years of breeding and production experience have shown that the use of single cross hybrids result in higher yields. It is thus important for commercial applications that the Rcg1 gene function in the hybrid plants (those in the farmer's production field) even when it is present in only one of the two parents used to make single cross hybrid seed. One of the inbred lines into which the Rcg1 line had been crossed, PH705, was thus used to create hybrid seed by crossing with PH4CV, an elite inbred that does not carry the Rcg1 locus. The resulting hybrid seeds were used in experiments identical to those described for the inbred lines as discussed above and scored in the same way at all five locations. The data are summarized for all locations in FIG. 17, which also shows the performance of the inbred PH705, and representative pictures shown in FIGS. 18 and 19. As can be seen, a clear difference in disease progression was observed in all locations for hybrid PH705×PH5W4 and in four of the five locations for PH705×PH87P. In the fifth location, environmental conditions were very stressful for plant growth, resulting in plants that were in poor condition. Under these conditions, measurements of plant disease resistance are often not reliable.

The results with both inbred lines and hybrid combinations containing Rcg1 clearly demonstrate that using the methods of the embodiments one can create commercially useful lines that are resistant to Cg-induced stalk rot.

Example 15

Markers within the Rcg1 Coding Sequence, Marker Locations and Designs within the Rcg1 Locus, and Haplotypes for the Flanking Chromosomal Region Three levels of marker locations may be utilized as a result of the fine mapping and cloning of the Rcg1 and Rcg1b genes: markers designed within the Rcg1 or Rcg1b coding sequences, markers designed within the non-colinear region that identify the Rcg1 locus (but outside of the Rcg1 and Rcg1b coding sequences), and markers designed within the flanking colinear region.

Following the identification and fine mapping of the Rcg1 gene, hybridization markers were designed that will function on SNP platforms. Since the Rcg1 gene occurs in a non-colinear region of the maize genome, the hybridization marker will be present in lines comprising the Rcg1 gene and absent on lines that do not comprise the Rcg1 gene. These markers identify polynucleotide sequences specific to the Rcg1 coding sequence listed on SEQ ID NO: 1. As noted in Table 7, there are other corn lines with variants of the Rcg1 coding sequence set forth in SEQ ID NO: 1, and these markers were also designed to also identify these Rcg1 coding sequence variants.

To accomplish this, a consensus map of variant Rcg1 coding sequence from different sources was created, as shown on Table 7. This consensus map aligned 4209 bases of the Rcg1 coding sequence isolated from MP305 with 3451 bases from PHBTB and 3457 bases from PH26T. The Rcg1 gene in both PHBTB and PH26T show resistance to anthracnose. Next, segments of the Rcg1 coding sequence were compared using BLAST® against several databases including NT (Public DNA from NCBI) and the highest homology hits were aligned with the Rcg1 consensus sequence to determine the segments that shared high homology and had common segments with other resistance genes in the NBS-LRR family. Regions unique to the Rcg1 coding sequence and common across the different sources of Rcg1 were selected for marker design. Specifically, since FLP111F and FLP111R primers produced a single amplicon that reliably diagnosed the presence of Rcg1 from different sources, the regions where FLP111F and FLP111R hybridized were therefore targeted for development of a SNP marker design.

Figure 23:
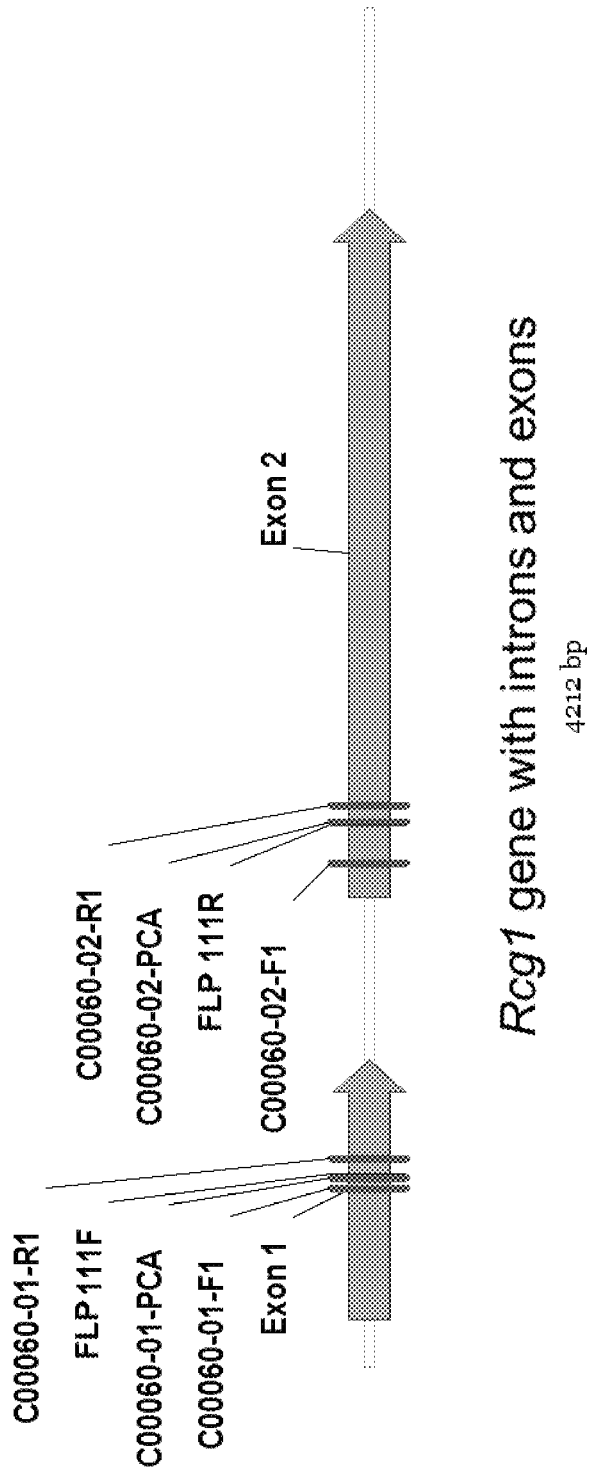
FIG. 23 shows the oligos for the Rcg1 hybridization markers designed for use with INVADER™ detection system reactions.
Figure 24:
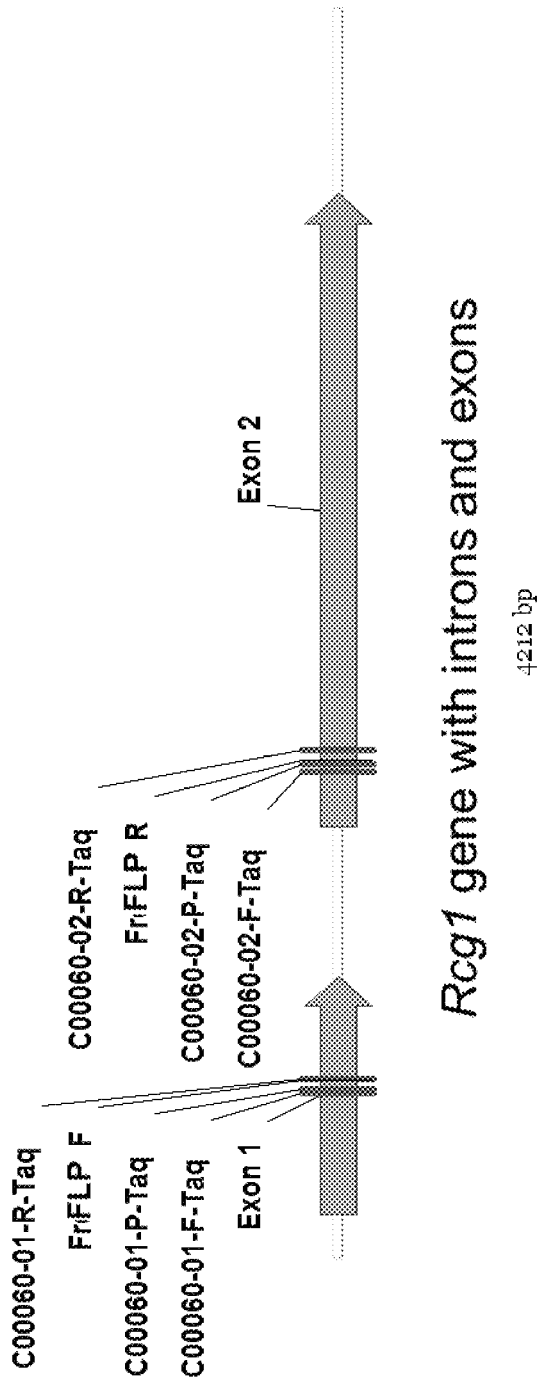
FIG. 24 shows the oligos for the Rcg1 hybridization markers designed for use with TAQMAN® detection system reactions.
Figure 25:
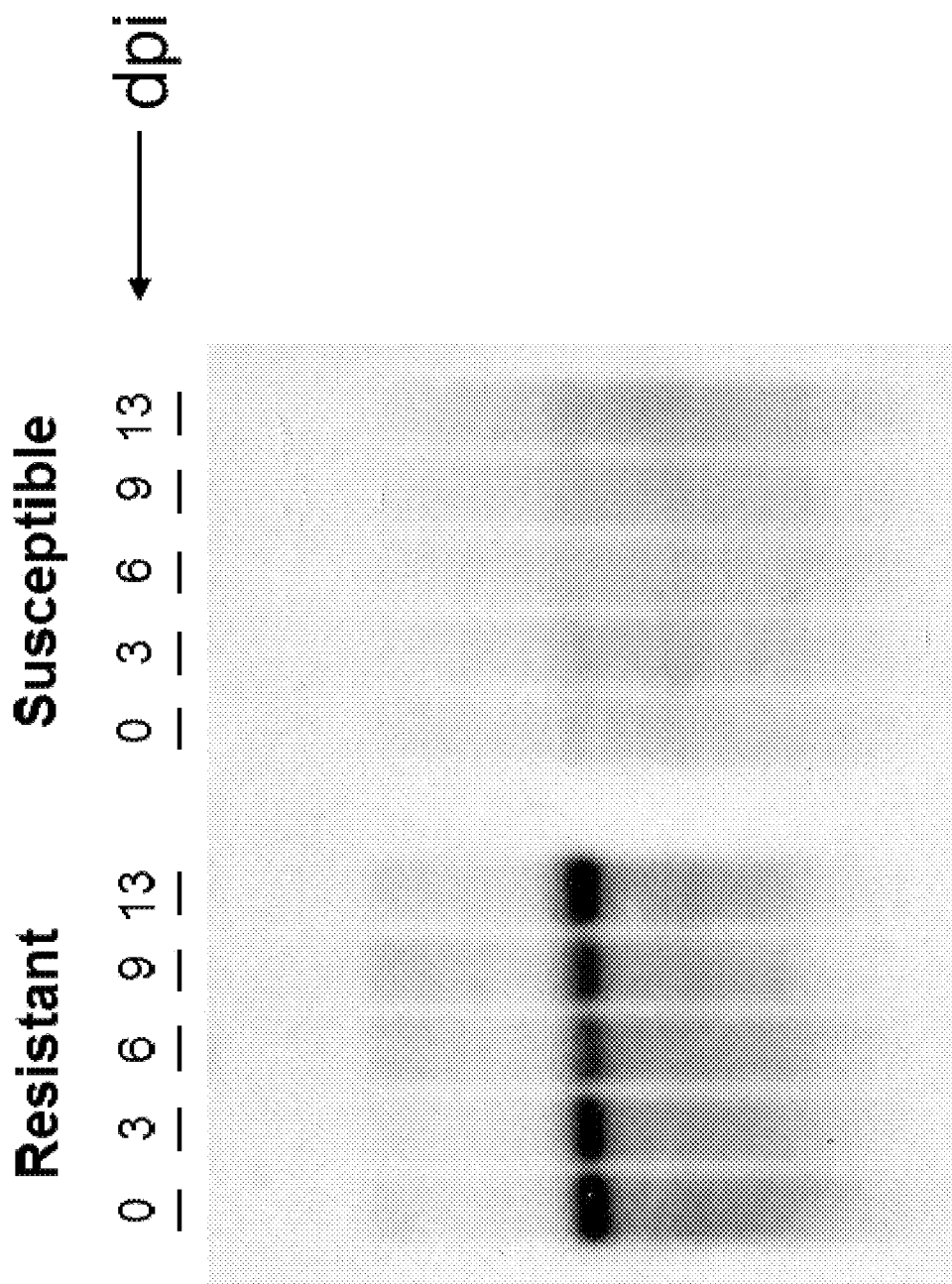
FIG. 25 shows the results of a northern blot obtained from approximately 1.5 mg of polyA-enriched RNA isolated from resistant and susceptible plants 0, 3, 6, 9, and 13 days post inoculation (dpi). The membrane was probed with a random primer labeled 420 bp Rcg1 fragment. Resistant tissue is from DE811ASR(BC5) and susceptible tissue is from DE811.
Figure 26:
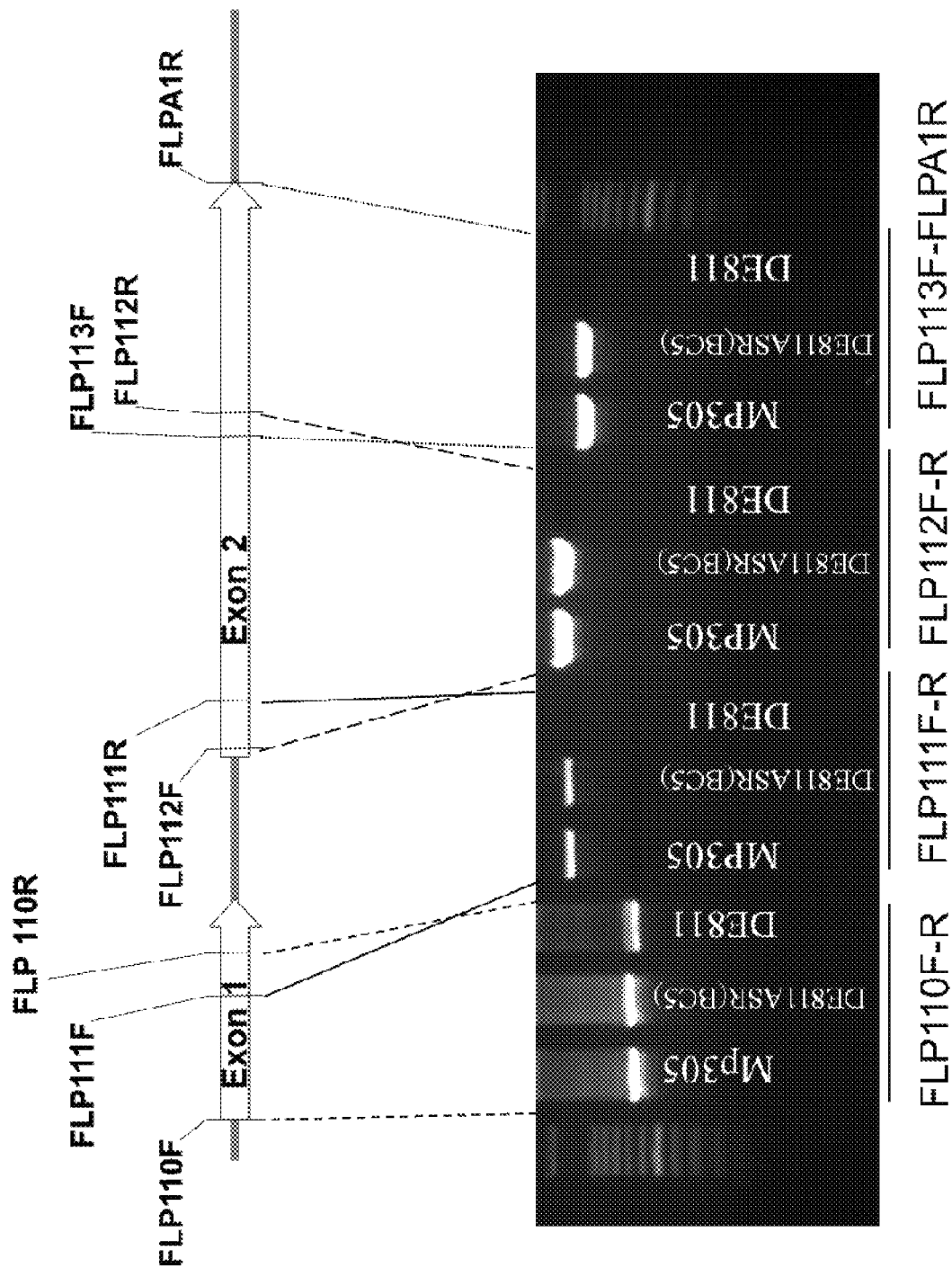
FIG. 26 shows that PCR amplification using Rcg1 specific primer pairs only amplifies in the resistant line DE811ASR (BC5) and donor parent MP305, but not in susceptible line DE811, with the exception of FLP110F-R, which amplifies the coiled coil-nucleotide binding site region, which is highly conserved, and thus amplifies a region elsewhere in the genome that is not Rcg1 in the DE811 line. A 100 bp ladder was used for fragment sizing.

An INVADER™ detection system marker was designed using a 1413 bp segment from the consensus sequence that contained both primer sites, with the primer regions themselves being targeted for probe and INVADER™ oligo hybridization. Primers were designed around each probe site to give an amplicon size below 150 bp. This marker indicated the presence of the Rcg1 coding sequence with fluorescence due to hybridization, with the absence of the Rcg1 coding sequence resulting in no fluorescence. A control fluorescence signal can also be generated by designing a marker that hybridizes to a second highly conserved maize gene, so that the presence of the Rcg1 coding sequence results in fluorescence of two dyes (Rcg1 and the conserved gene) and the absence of Rcg1 results in fluorescence due to the conserved gene only. This 'control' florescence may be used to reduce lab error by distinguishing between the situations where the Rcg1 is in fact absent and the situation where a false negative has occurred because of a failed reaction. Such markers are not limited to a specific marker detection platform. TAQMAN® markers were also designed to the same location (primer pairs FLP111F and FLP111R), that were used as for the INVADER™ detection system markers. The markers are shown on Table 15 and FIGS. 23 and 24.

The marker designs C00060-01-A and C00060-02-A were tested across a wide variety of sources and were highly successful at identifying plants that contained the Rcg1 locus and the Rcg1 gene, regardless of the source of the Rcg1 locus or Rcg1 gene. These markers were also used against a control set of nearly 100 diverse inbred lines known not to carry the gene, and no fluorescence was detected in the control set. Plants in which one or both of marker designs C00060-01-A and C00060-02-A confirmed as having Rcg1 include those shown in Table 7.

Therefore, this example shows that, based on the teaching provided herein, markers can be constructed that identify the Rcg1 coding sequence in a variety of sources.

Markers within the Rcg1 Locus

Markers may be designed to the Rcg1 locus in addition to or instead of using markers within the Rcg1 or Rcg1b coding sequences themselves. The close physical distance between the Rcg1 coding sequence and the non-colinear region makes it unlikely that the linkage between markers within the non-colinear region but outside of the Rcg1 coding sequence would be lost through recombination. As with markers for the Rcg1 coding sequence, a marker showing as present or absent would be sufficient to identify the Rcg1 locus.

To design markers for this region, a 64,460 bp segment of non-colinear region including the Rcg1 gene and the region directly north of the Rcg1 gene (therefore between Rcg1 and Rcg1b) was initially sequenced. BACs in this sequence were broken up into sub-clones of approximately 800 nucleotides in length and sequenced. These sequences were then assembled to construct the BAC sequence, and genic and repetitive regions were identified. Repetitive regions were identified in order to avoid placing markers in repetitive regions. Similarly, sequences with high homology with known maize sequences were easily avoided by a simple BLAST search. Potential sequences were avoided that contained SSRs, runs of As, Ts or Gs, or that would result in the generation of probes low in GC content which can cause problems within the INVADER™ detection system platform. See FIG. 9(*b*) and Table 17.

Selected segments were then put into INVADER CREATOR™ software, which generates oligos for an INVADER™ reaction. This produced a sense and an antisense design for all SNPs. The sense designs with the best scores and no penalties were selected. Although these markers have been designed, they have not yet been tested.

Primers were designed using Primer3 (Steve Rozen and Helen J. Skaletsky (2000). Primer3 is available on the world wide web for general users and for biologist programmers. See, Krawetz S, Misener S (eds) *Bioinformatics Methods and Protocols: Methods in Molecular Biology*. Humana Press, Totowa, N.J., pp 365-386. Primers were selected outside of the INVADER™ components, and preferred primers close to or below 150 bp long were selected. Primer temperature and length was adjusted to be most useful for the INVADER™ detection system platform, although if using other detection platforms primers would be optimized for use with such platforms.

Markers in the Colinear Region and Associated Haplotypes

Closely linked markers flanking the Rcg1 locus may be effectively used to select for a progeny plant that has inherited the Rcg1 locus from a parent that comprises the Rcg1 locus. The markers described herein, such as those listed on Table 16, as well as other markers genetically or physically mapped to the same chromosomal segment, may be used to select for a truncated chromosomal segment comprising the Rcg1 locus. Typically, a set of these markers will be used, (e.g., 2 or more, 3 or more, 4 or more, 5 or more) in the flanking region above the gene and a similar set in the flanking region below the gene. Optionally, as described above, a marker within the Rcg1 gene, the Rcg1b gene and/or Rcg1 locus may also be used. The parents and their progeny are screened for these sets of markers, and the markers that are polymorphic between the two parents are used for selection. The most proximal polymorphic markers to the Rcg1 gene, the Rcg1b gene or Rcg1 locus are used to select for the gene or locus, and the more distal polymorphic markers are used to select against the gene or locus. In an introgression program, this allows for selection of the Rcg1 gene, the Rcg1b gene or Rcg1 locus genotype at the more proximal polymorphic markers, and selection for the recurrent parent genotype at the more distal polymorphic markers. As described in more detail in Example 5 above, this process allowed for the efficient selection of a truncated chromosomal segment comprising the Rcg1 locus.

The process described above requires knowledge of the parental genotypes used in the cross. Optionally, haplotypes may be used so that the Rcg1 gene, the Rcg1b gene or Rcg1 locus can be selected for without first genotyping the specific parents used in the cross. This is a highly efficient way to select for the Rcg1 locus, especially in the absence of using markers within the Rcg1 gene, the Rcg1b gene or the Rcg1 locus.

All plants to be used in the breeding program, such as a gene introgression program, are screened with markers. The markers disclosed herein or equivalent markers on the same chromosomal segment may be used. The plant haplotypes (a series of SNP or other markers in linkage disequilibrium) are noted. The haplotype of the resistant plant around the Rcg1 locus is compared with the haplotype of the other plants to be used that do not comprise the Rcg1 locus. A haplotype unique to the resistant plant around the Rcg1 locus is then used for selection, and this haplotype will specifically identify the chromosomal segment from the resistant plant with the Rcg1 locus.

Based on an analysis of MP305 and a diverse set of several hundred corn lines, including 50 public corn lines shown in Table 18, a unique SNP haplotype for the MP305 chromosomal segment with the Rcg1 locus was identified. This SNP haplotype uniquely identifies the MP305 chromosomal segment that extends across MZA3434, MZA2591 and MZA11123. See FIG. 22, SEQ ID NO: 140, 141 and 142, and Tables 8, 9 and 10.

First, the primer pairs described in Table 2 for these three MZA's were used to identify haplotypes. The primer pairs MZA3434 E forward and reverse were used to amplify the genomic DNA of the set of corn lines. The PCR fragments were further purified by amplification with MZA3434 I forward and reverse primer pairs. This process was repeated for MZA2591 and MZA11123. The resulting PCR fragments were sequenced in the forward and reverse direction and the sequences were aligned to give a consensus sequence (see the sequences set forth in SEQ ID NOs: 140, 141 and 142). SNPs and indels within these consensus sequences are shown in Tables 8, 9 and 10. These series of SNPs and indels were compared across the set of genotypes.

For MZA3434, haplotype 8 was a rare haplotype allele, and was unique to MP305 and only one other corn line. This process was repeated for MZA2591, and MP305 was found to have haplotype 2 at MZA2591, which was shared by only two other corn lines. MP305 was the only corn line to have both haplotype 8 at MZA3434 and haplotype 2 at MZA2591, and therefore, the combination of these two haplotypes, 8 at MZA3434 and 2 at MZA2591, uniquely identifies the MP305 chromosomal region comprising the Rcg1 locus. MP305 also had an informative haplotype at MZA11123. MP305 was found to have haplotype 7, which was shared by 66 other corn lines, but none of these corn lines had haplotype 8 at MZA3434, or haplotype 2 at MZA2591. Therefore, any combination of 2 haplotypes at MZA3434, MZA2591 or MZA11123 could be used to uniquely identify MP305 among these genotypes. The haplotypes can then be interrogated by sequencing the fragment or by designing markers to each SNP or indel within a fragment.

Polymorphisms within haplotypes can be used to tag the haplotype. So called 'Tag-SNPs', or 'haplotype-tags' can be very useful in plant breeding, as more information than the polymorphism itself can be determined via extrapolation to the haplotype. A haplotype can also be defined as a series of polymorphisms across sequences, and these may be termed 'long-range haplotypes'.

Rare polymorphisms were observed within haplotypes that could be used as 'haplotype tags'. For example, either the SNPs MZA2591.32 (allele c) or MZA2591.35 (allele t) could be used to tag the haplotype 2 at MZA2591, and like haplotype 2, both were unique to MP305 and two other corn lines. The combination of SNPs MZA2591.32 (allele c) and MZA2591.35 (allele t) combined with MZA3434.17 (allele c) gave a 'long-range' haplotype that could be used to distinguish MP305 from all of the other genotypes in the study.

In addition, other markers, MZA15842, MZA11455, MZA8761 and MZA1851 also showed polymorphism with MP305. For MZA15842, only 18 of the other corn lines shared the same haplotype as MP305; for MZA11455, only 43 of the other corn lines shared the same haplotype as MP305; for MZA8761, only about half of the other corn lines shared the same haplotype as MP305; and for MZA1851, only about half of the other corn lines shared the same haplotype as MP305. Consensus sequences were developed for these markers, and are set forth in SEQ ID NOs: 143-146. SNPs and indels within these consensus sequences are shown in Tables 11-14. Four examples of unique haplotypes using the MZA markers are:
MZA11123 (haplotype 7)
MZA15842 (haplotype 3)
MZA8761 (haplotype 1)
and
MZA11123 (haplotype 7)
MZA15842 (haplotype 3)
MZA1851 (haplotype 1)
And
MZA11455 (haplotype 6)
MZA11123 (haplotype 7)
MZA15842 (haplotype 3)
MZA16510 (haplotype 4)
and
MZA11455 (haplotype 6)
MZA11123 (haplotype 7)
MZA15842 (haplotype 3)
MZA11394 (haplotype 6).

Multiple combinations within all of the markers disclosed herein, or other markers within the region, also will contain unique haplotypes that identify the Rcg1 locus.

TABLE 8

MZA3434 Polymorphisms

|  | MZA3434.3 | MZA3434.4 | MZA3434.6 | MZA3434.17 | MZA3434.2 | MZA3434.5 |
|---|---|---|---|---|---|---|
| Nucleotide position on SEQ ID NO: 140 | 282 | 283 | 327 | 343 | 377 | 387 |
| Type | DEL | DEL | DEL | SNP | DEL | DEL |
| Size of indel | 6 | 1 | 4 |  | 2 | 2 |
| MP305 | W | M | W | C | W | M |
| Counter allele | M | W | M | T | M | W |

M = "Mutant': differs to consensus
W = 'wild type': same as consensus,

TABLE 9

MZA2591 Polymorphisms

|  | MZA2591.43 | MZA2591.20 | MZA2591.21 | MZA2591.8 | MZA2591.12 | MZA2591.4 | MZA2591.31 |
|---|---|---|---|---|---|---|---|
| Nucleotide position on SEQ ID NO: 141 | 101 | 114 | 124 | 131 | 160 | 176 | 213 |
| Type | INS | SNP | SNP | DEL | DEL | INS | SNP |
| Size of indel | 3 |  |  | 2 | 3 |  |  |
| MP305 | W | T | C | W | W | W | T |
| Counter allele | M | A | T | M | M | M | C |

|  | MZA2591.32 | MZA2591.1 | MZA2591.33 | MZA2591.35 | MZA2591.36 |
|---|---|---|---|---|---|
| Nucleotide position on SEQ ID NO: 141 | 223 | 238 | 250 | 257 | 264 |
| Type | SNP | DEL | SNP | SNP | SNP |
| Size of indel |  | 2 |  |  |  |
| MP305 | C | M | C | T | C |
| Counter allele | T | W | G | A | G |

M = "Mutant': differs to consensus
W = 'wild type': same as consensus,

TABLE 9 (cont.)

MZA2591 Polymorphisms

|  | MZA2591.37 | MZA2591.38 | MZA2591.10 | MZA2591.39 | MZA2591.3 |
|---|---|---|---|---|---|
| Nucleotide position on SEQ ID NO: 141 | 271 | 282 | 290 | 310 | 313 |
| Type | SNP | SNP | DEL | SNP | DEL |
| Size of indel |  |  | 4 |  | 2 |
| MP305 | G | C | M | T | M |
| Counter Allele | A | T | W | C | W |

|  | MZA2591.40 | MZA2591.41 | MZA2591.6 | MZA2591.7 | MZA2591.9 |
|---|---|---|---|---|---|
| Nucleotide position on SEQ ID NO: 141 | 325 | 332 | 332 | 371 | 404 |
| Type | SNP | SNP | DEL | DEL | DEL |
| Size of indel |  |  |  |  | 1 |
| MP305 | T | C | W | W | W |
| Counter Allele | C | T | M | M | M |

M = "Mutant': differs to consensus
W = 'wild type': same as consensus,

TABLE 10

MZA11123 Polymorphisms

| | MZA11123.5 | MZA11123.18 | MZA11123.2 | MZA11123.13 | MZA11123.34 |
|---|---|---|---|---|---|
| Nucleotide position on SEQ ID NO: 142 | 631 | 641 | 650 | 671 | 703 |
| Type | DEL | INS | INS | INS | SNP |
| Size of indel | 1 | 1 | 1 | 10 | |
| MP305 | W | W | W | W | G |
| Counter allele | M | M | M | M | A |

| | MZA11123.37 | MZA11123.40 | MZA11123.41 | MZA11123.45 | MZA11123.48 |
|---|---|---|---|---|---|
| Nucleotide position on SEQ ID NO: 142 | 727 | 744 | 786 | 807 | 864 |
| Type | SNP | SNP | SNP | SNP | SNP |
| Size of indel | | | | | |
| MP305 | T | C | A | C | T |
| Counter allele | C | A | G | A | A |

| | MZA11123.9 | MZA11123.19 | MZA11123.59 | MZA11123.17 | MZA11123.16 |
|---|---|---|---|---|---|
| Nucleotide position on SEQ ID NO: 142 | 915 | 934 | 956 | 991 | 1010 |
| Type | INS | DEL | SNP | DEL | DEL |
| Size of indel | 18 | 1 | | 3 | 3 |
| MP305 | W | W | C | M | W |
| Counter allele | M | M | T | W | M |

M = "Mutant': differs to consensus
W = 'wild type': same as consensus,

TABLE 11

MZA15842 Polymorphisms

| | MZA15842.3 | MZA15842.4 | MZA15842.5 | MZA15842.7 | MZA15842.8 |
|---|---|---|---|---|---|
| Nucleotide position on SEQ ID NO: 143 | 287 | 295 | 313 | 337 | 353 |
| Type | SNP | SNP | SNP | SNP | SNP |
| MP305 | T | A | T | C | T |
| Counter Allele | C | G | A | T | C |

| | MZA15842.9 | MZA15842.10 | MZA15842.11 | MZA15842.12 | MZA15842.3 |
|---|---|---|---|---|---|
| Nucleotide position on SEQ ID NO: 143 | 366 | 436 | 439 | 463 | 287 |
| Type | SNP | SNP | SNP | SNP | SNP |
| MP305 | T | G | A | A | T |
| Counter Allele | C | A | G | G | C |

M = "Mutant': differs to consensus
W = 'wild type': same as consensus,

TABLE 12

MZA8761 Polymorphisms

| | MZA8761.3 | MZA8761.6 | MZA8761.7 | MZA8761.8 | MZA8761.9 | MZA8761.10 | MZA8761.11 | MZA8761.4 |
|---|---|---|---|---|---|---|---|---|
| Nucleotide position on SEQ ID NO: 145 | 595 | 633 | 671 | 681 | 687 | 696 | 702 | 710 |
| Type | DEL | SNP | SNP | SNP | SNP | SNP | SNP | DEL |
| Size of indel | 7 | | | | | | | 1 |
| MP305 | W | G | T | G | T | G | C | W |
| Counter allele | M | A | C | C | C | T | A | M |

TABLE 12-continued

| MZA8761 Polymorphisms | | | | | | |
|---|---|---|---|---|---|---|
| | MZA8761.2 | MZA8761.1 | MZA8761.5 | MZA8761.12 | MZA8761.13 | MZA8761.14 |
| Nucleotide position on SEQ ID NO: 145 | 710 | 710 | 722 | 779 | 882 | 901 |
| Type | DEL | INS | DEL | SNP | SNP | SNP |
| Size of indel | 1 | 1 | 1 | | | |
| MP305 | W | W | W | T | C | T |
| Counter allele | M | M | M | G | T | C |

M = "Mutant": differs to consensus
W = 'wild type': same as consensus,

TABLE 13

| MZA1851 Polymorphisms | | | | | | |
|---|---|---|---|---|---|---|
| | MZA1851.24 | MZA1851.41 | MZA1851.32 | MZA1851.49 | MZA1851.51 | MZA1851.52 |
| Nucleotide position on SEQ ID NO: 144 | 1213 | 1236 | 1271 | 1465 | 1615 | 1617 |
| Type | INS | SNP | INS | SNP | SNP | SNP |
| Size of indel | 19 | | 34 | | | |
| MP305 | W | G | W | A | C | A |
| Counter Allele | M | A | M | G | A | C |

| | MZA1851.53 | MZA1851.54 | MZA1851.55 | MZA1851.56 | MZA1851.35 |
|---|---|---|---|---|---|
| Nucleotide position on SEQ ID NO: 144 | 1686 | 1697 | 1698 | 1701 | 1717 |
| Type | SNP | SNP | SNP | SNP | DEL |
| Size of indel | | | | | 6 |
| MP305 | T | A | G | T | W |
| Counter Allele | C | C | C | C | M |

M = "Mutant": differs to consensus
W = 'wild type': same as consensus,

TABLE 14

| MZA11455 Polymorphisms | | | | | | |
|---|---|---|---|---|---|---|
| | MZA11455.3 | MZA11455.5 | MZA11455.2 | MZA11455.7 | MZA11455.8 | MZA11455.10 |
| Nucleotide position on SEQ ID NO: 146 | 373 | 392 | 402 | 425 | 426 | 432 |
| Type | DEL | SNP | DEL | SNP | SNP | SNP |
| Size of indel | 1 | | 10 | | | |
| MP305 | M | G | M | G | C | C |
| Counter allele | W | C | W | A | G | G |

| | MZA11455.11 | MZA11455.12 | MZA11455.4 | MZA11455.13 | MZA11455.14 | MZA11455.15 |
|---|---|---|---|---|---|---|
| Nucleotide position on SEQ ID NO: 146 | 435 | 491 | 526 | 552 | 581 | 599 |
| Type | SNP | SNP | DEL | SNP | SNP | SNP |
| Size of indel | | | 1 | | | |
| MP305 | A | T | M | A | G | G |
| Counter allele | G | A | W | G | A | C |

| | MZA11455.1 | MZA11455.17 | MZA11455.18 | MZA11455.19 |
|---|---|---|---|---|
| Nucleotide position on SEQ ID NO: 146 | 610 | 611 | 628 | 634 |
| Type | DEL | SNP | SNP | SNP |
| Size of indel | 3 | | | |
| MP305 | W | G | C | A |
| Counter allele | M | A | G | C |

M = "Mutant": differs to consensus
W = 'wild type': same as consensus,

TABLE 15

| | Markers within the Rcg1 Coding Sequence | | | | |
|---|---|---|---|---|---|
| SNP Platform | INVADER™ | INVADER™ | TAQMAN® | TAQMAN® | PCR |
| Marker Name | C00060-01-A | C00060-02-A | C00060-01 | C00060-02 | FLP111 |
| Forward Primer Name | C00060-01-F1 | C00060-02-F1 | C00060-01-F-Taq | C00060-02-F-Taq | FLP111F |
| Position on SEQ ID NO: 1 | 550-567 | 1562-1586 | 552-568 | 1634-1659 | 595-619 |
| Forward Primer Sequence | SEQ ID NO: 145 | SEQ ID NO: 146 | SEQ ID NO: 147 | SEQ ID NO: 148 | SEQ ID NO: 37 |
| Reverse Primer Name | C00060-01-R1 | C00060-02-R1 | C00060-01-R-Taq | C00060-02-R-Taq | FLP111RB |
| Position on SEQ ID NO: 1 | 641-658 | 1739-1767 | 599-620 | 1707-1730 | 1676-1700 |
| Reverse Primer Sequence | SEQ ID NO: 149 | SEQ ID NO: 150 | SEQ ID NO: 151 | SEQ ID NO: 152 | SEQ ID NO: 153 |
| Probe Name | C00060-01-PCA | C00060-02-PCA | C00060-01-P-Taq | C00060-02-P-Taq | |
| Position on SEQ ID NO: 1 | 586-603 | 1685-1701 | 570-595 | 1662-1693 | |
| Probe Sequence | SEQ ID NO: 154 | SEQ ID NO: 155 | SEQ ID NO: 156 | SEQ ID NO: 157 | |

TABLE 16

Markers contained within defined chromosomal intervals that can be used to select for Rcg1.
The public markers are taken from the IBM2 neighbors 4 map, while the relative
locations of the Pioneer markers (prefix 'MZA') were determined by mapping
to the same genetic map, and by location on the physical map.

| Interval (and position on IBM2 neighbors 4 map in cM) | Position relative to Rcg1 or Rcg1b | Markers that could be used for selection of Rcg1 |
|---|---|---|
| UMC2041 (483.93)- UMC2200 (543.44) | Above the Rcg1b gene UMC2041 - Rcg1b | UMC2041, AY112127, UMC1086, AY110631, UMC2285, MZA8136, MZA6064, NPI270, NPI300C, PHP20071, CDO127a, RGPI102, UAZ122, BNL17.05, MZA11455, MZA15842, MZA11123, MZA2591 |
| | Below the Rcg1 gene Rcg1 - UMC2200 | PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187, NPI410, PSR109B, UMC1371, UMC1842, UMC1856, AY109980, UMC1132, NFD106, AY105971, AY110989, ENSI002A, RZ596B, BNL23A, BNL29, UMC2200 |
| UMC1086 (500.59)- UMC2200 (543.44) | Above the Rcg1b gene UMC1086 - Rcg1b | UMC1086, AY110631, UMC2285, MZA8136, MZA6064, NPI270, NPI300C, PHP20071, CDO127a, RGPI102, UAZ122, BNL17.05, MZA11455, MZA15842, MZA11123, MZA2591 |
| | Below the Rcg1 gene Rcg1 - UMC2200 | PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187, NPI410, PSR109B, UMC1371, UMC1842, UMC1856, AY109980, UMC1132, NFD106, AY105971, AY110989, ENSI002A, RZ596B, BNL23A, BNL29, UMC2200 |
| UMC2285 (514.9)- UMC2187 (531.7) | Above the Rcg1b gene UMC2285 - Rcg1b | UMC2285, MZA8136, MZA6064, NPI270, NPI300C, PHP20071, CDO127a, RGPI102, UAZ122, BNL17.05, MZA11455, MZA15842, MZA11123, MZA2591 |
| | Below the Rcg1 gene Rcg1 - UMC2187 | PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187 |
| Within UMC2285 (514.9)- UMC15a (525.8) | Above the Rcg1b gene, within UMC2285 - Rcg1b | MZA8136, MZA6064, NPI270, NPI300C, PHP20071, CDO127a, RGPI102, UAZ122, BNL17.05, MZA11455, MZA15842, MZA11123, MZA2591 |

TABLE 16-continued

Markers contained within defined chromosomal intervals that can be used to select for Rcg1. The public markers are taken from the IBM2 neighbors 4 map, while the relative locations of the Pioneer markers (prefix 'MZA') were determined by mapping to the same genetic map, and by location on the physical map.

| Interval (and position on IBM2 neighbors 4 map in cM) | Position relative to Rcg1 or Rcg1b | Markers that could be used for selection of Rcg1 |
|---|---|---|
| | Below the Rcg1 gene, within Rcg1 - UMC15a | PHI093, MZA1215, MZA1216, MZA3434, CL12681_1, NPI444 |

TABLE 17

Markers Within the Rcg1 Locus

| Marker Name | SNP sequence position on SEQ ID NO: 137 | SNP Sequence | INVADER ™ Oligo | INVADER ™ Probe | Forward Primer | Reverse Primer |
|---|---|---|---|---|---|---|
| PHD0001-01 | 12-270 | SEQ ID NO: 158 | SEQ ID NO: 159 | SEQ ID NO: 160 | SEQ ID NO: 161 | SEQ ID NO: 162 |
| PHD0002-01 | 272-530 | SEQ ID NO: 163 | SEQ ID NO: 164 | SEQ ID NO: 165 | SEQ ID NO: 166 | SEQ ID NO: 167 |
| PHD0003-01 | 7232-7500 | SEQ ID NO: 168 | SEQ ID NO: 169 | SEQ ID NO: 170 | SEQ ID NO: 171 | SEQ ID NO: 172 |
| PHD0004-01 | 11302-11580 | SEQ ID NO: 173 | SEQ ID NO: 174 | SEQ ID NO: 175 | SEQ ID NO: 176 | SEQ ID NO: 177 |
| PHD0005-01 | 11581-11880 | SEQ ID NO: 178 | SEQ ID NO: 179 | SEQ ID NO: 180 | SEQ ID NO: 181 | SEQ ID NO: 182 |
| PHD0006-01 | 11881-12170 | SEQ ID NO: 183 | SEQ ID NO: 184 | SEQ ID NO: 185 | SEQ ID NO: 186 | SEQ ID NO: 187 |
| PHD0007-01 | 12171-12470 | SEQ ID NO: 188 | SEQ ID NO: 189 | SEQ ID NO: 190 | SEQ ID NO: 191 | SEQ ID NO: 192 |
| PHD0008-01 | 25417-25690 | SEQ ID NO: 193 | SEQ ID NO: 194 | SEQ ID NO: 195 | SEQ ID NO: 196 | SEQ ID NO: 197 |
| PHD0009-01 | 25692-25950 | SEQ ID NO: 198 | SEQ ID NO: 199 | SEQ ID NO: 200 | SEQ ID NO: 201 | SEQ ID NO: 202 |
| PHD0010-01 | 25951-26200 | SEQ ID NO: 203 | SEQ ID NO: 204 | SEQ ID NO: 205 | SEQ ID NO: 206 | SEQ ID NO: 207 |
| PHD0011-01 | 26602-26860 | SEQ ID NO: 208 | SEQ ID NO: 209 | SEQ ID NO: 210 | SEQ ID NO: 211 | SEQ ID NO: 212 |
| PHD0012-01 | 26932-27200 | SEQ ID NO: 213 | SEQ ID NO: 214 | SEQ ID NO: 215 | SEQ ID NO: 216 | SEQ ID NO: 217 |
| PHD0013-01 | 27322-27580 | SEQ ID NO: 218 | SEQ ID NO: 219 | SEQ ID NO: 220 | SEQ ID NO: 221 | SEQ ID NO: 222 |
| PHD0014-01 | 28472-28740 | SEQ ID NO: 223 | SEQ ID NO: 224 | SEQ ID NO: 225 | SEQ ID NO: 226 | SEQ ID NO: 227 |
| PHD0015-01 | 28791-29002 | SEQ ID NO: 228 | SEQ ID NO: 229 | SEQ ID NO: 230 | SEQ ID NO: 231 | SEQ ID NO: 232 |

TABLE 18

List of Public Lines use in Haplotype Analysis 38-11
A165
A188
A509
A556
A619
A632
B
B14
B37
B42
B64
B73
B84
B89
B94
C103
C106
CI66
CM49
CO109
D02
D146
F2
F252
F257
F283
F7
GT119
H84
H99
HATO4
HY
Indiana H60
K187-11217
K55
L1546
L317
Minn49
MO13
MP305
N28
OH07
OH40B
OH43
OH45
OS420
OS426
PA91
R159
SC213R
SD105
SRS303
T232
TR9-1-1-6
TX601
V3
W153R
WF9

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10731225B2). An electronic copy of the "Sequence Listing" will also be available from the USPTO upon request and payment of the fee set forth in 37 CFR 1.19(b)(3).

What is claimed is:

1. A modified plant comprising a first heterologous polynucleotide encoding a Rcg1 polypeptide having at least 90% sequence identity to SEQ ID NO: 3 and a second heterologous polynucleotide encoding a Rcg1b polypeptide having at least 90% sequence identity to SEQ ID NO: 246, and wherein the modified plant has enahanced resistance to *Colletotrichum*.

2. The modified plant of claim 1, wherein the first heterologous polynucleotide comprises SEQ ID NO: 2.

3. The modified plant of claim 1, wherein the second heterologous polynucleotide comprises SEQ ID NO: 245.

4. The modified plant of claim 1, wherein the modified plant is a maize plant.

* * * * *